US008641704B2

(12) United States Patent
Werneth et al.

(10) Patent No.: US 8,641,704 B2
(45) Date of Patent: Feb. 4, 2014

(54) ABLATION THERAPY SYSTEM AND METHOD FOR TREATING CONTINUOUS ATRIAL FIBRILLATION

(75) Inventors: Randell L. Werneth, San Diego, CA (US); Christopher G. Kunis, San Diego, CA (US); Hakan Oral, Ann Arbor, MI (US); Fred Morady, Ann Arbor, MI (US); J. Christopher Flaherty, Topsfield, MA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 1431 days.

(21) Appl. No.: 12/116,753

(22) Filed: May 7, 2008

(65) Prior Publication Data

US 2008/0281312 A1 Nov. 13, 2008

Related U.S. Application Data

(60) Provisional application No. 60/928,788, filed on May 11, 2007.

(51) Int. Cl.
*A61B 18/14* (2006.01)

(52) U.S. Cl.
USPC .............................. 606/32; 606/41

(58) Field of Classification Search
USPC .............................. 606/32, 34, 41
See application file for complete search history.

(56) References Cited

U.S. PATENT DOCUMENTS

| 3,516,412 A | 6/1970 | Ackerman |
| 3,951,136 A | 4/1976 | Wall |
| 4,017,903 A | 4/1977 | Chu |
| 4,112,952 A | 9/1978 | Thomas et al. |
| 4,411,266 A | 10/1983 | Cosman |
| 4,432,377 A | 2/1984 | Dickhudt |

(Continued)

FOREIGN PATENT DOCUMENTS

| AU | 5200671 | 10/2005 |
| CA | 2327322 | 11/1999 |

(Continued)

OTHER PUBLICATIONS

Oral et al., "Catheter ablation for paroxysmal atrial fibrillation: segmental pulmonary vein ostial ablation versus left atrial ablation," Circulation, vol. 108, pp. 2355-2360, 2003.

(Continued)

*Primary Examiner* — Michael Peffley
*Assistant Examiner* — Daniel Fowler
(74) *Attorney, Agent, or Firm* — Christopher & Weisberg, P.A.

(57) ABSTRACT

An ablation therapy system and systematic method is provided for treating continuous atrial fibrillation. The therapy system includes a Multi-Channel RF Ablation Generator, an ECG interface, an assembly of at least three ablation catheters, and an ECG interface operably coupling and interfacing the catheters to both an ECG unit and the RF Ablation Generator. The systematic method includes transseptally accessing the Left Atrium (LA) through the septum of the patient's heart, and performing an endocardial pulmonary vein ablation procedure on the pulmonary vein ostial tissue surrounding one or more pulmonary veins in a manner treating aberrant conductive pathways therethrough. After performing the pulmonary vein ablation, the method further includes performing an endocardial atrial septum ablation procedure on the septal tissue in a manner treating aberrant conductive pathways therethrough.

80 Claims, 17 Drawing Sheets

(56) References Cited

U.S. PATENT DOCUMENTS

| | | |
|---|---|---|
| 4,660,571 A | 4/1987 | Hess et al. |
| 4,699,147 A | 10/1987 | Chilson et al. |
| 4,785,815 A | 11/1988 | Cohen |
| 4,860,769 A | 8/1989 | Fogarty et al. |
| 4,869,248 A | 9/1989 | Narula |
| 4,882,777 A | 11/1989 | Narula |
| 4,896,671 A | 1/1990 | Cunningham et al. |
| 4,907,589 A | 3/1990 | Cosman |
| 4,920,980 A | 5/1990 | Jackowski |
| 4,940,064 A | 7/1990 | Desai |
| 4,966,597 A | 10/1990 | Cosman |
| 5,010,894 A | 4/1991 | Edhag |
| 5,016,808 A | 5/1991 | Heil, Jr. et al. |
| 5,083,565 A | 1/1992 | Parins |
| 5,100,423 A | 3/1992 | Fearnot |
| 5,156,151 A | 10/1992 | Imran |
| 5,184,621 A | 2/1993 | Vogel et al. |
| 5,215,103 A | 6/1993 | Desai |
| 5,228,442 A | 7/1993 | Imran |
| 5,230,349 A | 7/1993 | Langberg |
| 5,231,987 A | 8/1993 | Robson |
| 5,231,995 A | 8/1993 | Desai |
| 5,234,004 A | 8/1993 | Hascoet et al. |
| 5,239,999 A | 8/1993 | Imran |
| 5,255,679 A | 10/1993 | Imran |
| 5,279,299 A | 1/1994 | Imran |
| 5,281,213 A | 1/1994 | Milder et al. |
| 5,281,218 A | 1/1994 | Imran |
| 5,309,910 A | 5/1994 | Edwards et al. |
| 5,313,943 A | 5/1994 | Houser et al. |
| 5,318,525 A | 6/1994 | West et al. |
| 5,324,284 A | 6/1994 | Imran |
| 5,327,889 A | 7/1994 | Imran |
| 5,330,466 A | 7/1994 | Imran |
| 5,334,193 A | 8/1994 | Nardella |
| 5,342,295 A | 8/1994 | Imran |
| 5,342,357 A | 8/1994 | Nardella |
| 5,345,936 A | 9/1994 | Pomeranz et al. |
| 5,348,554 A | 9/1994 | Imran et al. |
| D351,652 S | 10/1994 | Thompson et al. |
| 5,364,352 A | 11/1994 | Cimino et al. |
| 5,365,926 A | 11/1994 | Desai |
| 5,370,644 A | 12/1994 | Langberg |
| 5,383,917 A | 1/1995 | Desai et al. |
| 5,391,147 A | 2/1995 | Imran et al. |
| 5,397,304 A | 3/1995 | Truckai |
| 5,397,339 A | 3/1995 | Desai |
| 5,400,783 A | 3/1995 | Pomeranz et al. |
| 5,404,638 A | 4/1995 | Imran |
| 5,406,946 A | 4/1995 | Imran |
| 5,411,025 A | 5/1995 | Webster, Jr. |
| 5,423,808 A | 6/1995 | Edwards et al. |
| 5,423,811 A | 6/1995 | Imran et al. |
| 5,433,198 A | 7/1995 | Desai |
| 5,433,739 A | 7/1995 | Sluijter et al. |
| 5,445,148 A | 8/1995 | Jaraczewski et al. |
| 5,462,521 A | 10/1995 | Brucker et al. |
| 5,462,545 A | 10/1995 | Wang et al. |
| 5,465,717 A | 11/1995 | Imran et al. |
| 5,471,982 A | 12/1995 | Edwards et al. |
| 5,487,757 A | 1/1996 | Truckai et al. |
| 5,492,119 A | 2/1996 | Abrams |
| 5,500,011 A | 3/1996 | Desai |
| 5,507,802 A | 4/1996 | Imran |
| 5,509,411 A | 4/1996 | Littmann et al. |
| 5,527,279 A | 6/1996 | Imran |
| 5,533,967 A | 7/1996 | Imran |
| 5,536,267 A | 7/1996 | Edwards et al. |
| 5,540,681 A | 7/1996 | Strul et al. |
| 5,545,161 A | 8/1996 | Imran |
| 5,545,193 A | 8/1996 | Fleischman et al. |
| 5,545,200 A | 8/1996 | West et al. |
| 5,558,073 A | 9/1996 | Pomeranz et al. |
| 5,573,533 A | 11/1996 | Strul |
| 5,575,766 A | 11/1996 | Swartz et al. |
| 5,575,810 A | 11/1996 | Swanson et al. |
| 5,578,007 A | 11/1996 | Imran |
| 5,582,609 A | 12/1996 | Swanson et al. |
| 5,584,830 A | 12/1996 | Ladd et al. |
| 5,588,432 A | 12/1996 | Crowley |
| 5,588,964 A | 12/1996 | Imran et al. |
| 5,595,183 A | 1/1997 | Swanson et al. |
| 5,596,995 A | 1/1997 | Sherman et al. |
| 5,598,848 A | 2/1997 | Swanson et al. |
| 5,601,088 A | 2/1997 | Swanson et al. |
| 5,606,974 A | 3/1997 | Castellano et al. |
| 5,607,462 A | 3/1997 | Imran |
| 5,620,481 A | 4/1997 | Desai et al. |
| 5,626,136 A | 5/1997 | Webster, Jr. |
| 5,630,425 A | 5/1997 | Panescu et al. |
| 5,630,837 A | 5/1997 | Crowley |
| 5,637,090 A | 6/1997 | McGee et al. |
| D381,076 S | 7/1997 | Thornton et al. |
| 5,645,064 A | 7/1997 | Littmann et al. |
| 5,645,082 A | 7/1997 | Sung et al. |
| 5,656,029 A | 8/1997 | Imran et al. |
| 5,657,755 A | 8/1997 | Desai |
| 5,658,278 A | 8/1997 | Imran et al. |
| 5,662,606 A | 9/1997 | Cimino et al. |
| 5,666,970 A | 9/1997 | Smith |
| 5,673,695 A | 10/1997 | McGee et al. |
| 5,680,860 A | 10/1997 | Imran |
| 5,681,280 A | 10/1997 | Rusk et al. |
| 5,682,885 A | 11/1997 | Littmann et al. |
| 5,685,322 A | 11/1997 | Sung et al. |
| 5,687,723 A | 11/1997 | Avitall |
| 5,693,078 A | 12/1997 | Desai et al. |
| 5,697,927 A | 12/1997 | Imran et al. |
| 5,697,928 A | 12/1997 | Walcott et al. |
| 5,699,796 A | 12/1997 | Littmann et al. |
| 5,702,438 A | 12/1997 | Avitall |
| 5,704,791 A | 1/1998 | Gillio |
| 5,706,809 A | 1/1998 | Littmann et al. |
| 5,711,298 A | 1/1998 | Littmann et al. |
| 5,716,389 A | 2/1998 | Walinsky et al. |
| 5,722,400 A * | 3/1998 | Ockuly et al. ................ 600/374 |
| 5,722,401 A | 3/1998 | Pietroski et al. |
| 5,722,975 A | 3/1998 | Edwards et al. |
| 5,724,985 A | 3/1998 | Snell et al. |
| 5,733,323 A | 3/1998 | Buck et al. |
| 5,735,280 A | 4/1998 | Sherman et al. |
| 5,741,320 A | 4/1998 | Thornton et al. |
| 5,766,152 A | 6/1998 | Morley et al. |
| 5,769,791 A | 6/1998 | Benaron et al. |
| 5,769,847 A | 6/1998 | Panescu et al. |
| 5,772,590 A | 6/1998 | Webster, Jr. |
| 5,775,327 A | 7/1998 | Randolph et al. |
| 5,782,239 A | 7/1998 | Webster, Jr. |
| 5,782,760 A | 7/1998 | Schaer |
| 5,782,828 A | 7/1998 | Chen et al. |
| 5,782,899 A | 7/1998 | Imran |
| 5,792,140 A | 8/1998 | Tu et al. |
| 5,800,482 A | 9/1998 | Pomeranz et al. |
| 5,810,740 A | 9/1998 | Paisner |
| 5,820,568 A | 10/1998 | Willis |
| 5,827,272 A | 10/1998 | Breining et al. |
| 5,837,001 A | 11/1998 | Mackey |
| 5,849,028 A | 12/1998 | Chen |
| 5,857,464 A | 1/1999 | Desai |
| 5,857,997 A | 1/1999 | Cimino et al. |
| 5,860,920 A | 1/1999 | McGee et al. |
| 5,863,291 A | 1/1999 | Schaer |
| 5,871,523 A | 2/1999 | Fleischman et al. |
| 5,873,865 A | 2/1999 | Horzewski et al. |
| 5,876,399 A | 3/1999 | Chia et al. |
| 5,881,732 A | 3/1999 | Sung et al. |
| 5,882,333 A | 3/1999 | Schaer et al. |
| 5,885,278 A | 3/1999 | Fleischman |
| 5,891,027 A | 4/1999 | Tu et al. |
| 5,891,135 A | 4/1999 | Jackson et al. |
| 5,891,137 A | 4/1999 | Chia et al. |
| 5,891,138 A | 4/1999 | Tu et al. |
| 5,893,847 A | 4/1999 | Kordis |
| 5,893,884 A | 4/1999 | Tu |

(56) References Cited

U.S. PATENT DOCUMENTS

| | | | |
|---|---|---|---|
| 5,893,885 A | 4/1999 | Webster, Jr. |
| 5,895,355 A | 4/1999 | Schaer |
| 5,895,417 A | 4/1999 | Pomeranz et al. |
| 5,897,554 A | 4/1999 | Chia et al. |
| 5,904,680 A | 5/1999 | Kordis et al. |
| 5,906,605 A | 5/1999 | Coxum |
| 5,910,129 A | 6/1999 | Koblish et al. |
| 5,911,720 A | 6/1999 | Bourne et al. |
| 5,913,854 A | 6/1999 | Maguire et al. |
| 5,916,213 A * | 6/1999 | Haissaguerre et al. ......... 606/41 |
| 5,916,214 A | 6/1999 | Cosio et al. |
| 5,928,191 A | 7/1999 | Houser et al. |
| 5,931,835 A | 8/1999 | Mackey |
| 5,935,063 A | 8/1999 | Nguyen |
| 5,938,694 A | 8/1999 | Jaraczewski et al. |
| 5,941,845 A | 8/1999 | Tu et al. |
| 5,951,471 A | 9/1999 | de la Rama et al. |
| 5,954,719 A | 9/1999 | Chen et al. |
| 5,957,842 A | 9/1999 | Littmann et al. |
| 5,960,796 A | 10/1999 | Sung et al. |
| 5,967,978 A | 10/1999 | Littmann et al. |
| 5,968,040 A | 10/1999 | Swanson et al. |
| 5,971,980 A | 10/1999 | Sherman |
| 5,992,418 A | 11/1999 | de la Rama et al. |
| 5,997,532 A | 12/1999 | McLaughlin et al. |
| 6,001,093 A | 12/1999 | Swanson et al. |
| 6,001,095 A | 12/1999 | de la Rama et al. |
| 6,002,956 A | 12/1999 | Schaer |
| 6,004,269 A | 12/1999 | Crowley et al. |
| 6,012,457 A * | 1/2000 | Lesh ............................ 128/898 |
| 6,014,581 A | 1/2000 | Whayne et al. |
| 6,021,340 A | 2/2000 | Randolph et al. |
| 6,023,638 A | 2/2000 | Swanson |
| 6,029,091 A | 2/2000 | de la Rama et al. |
| 6,032,674 A | 3/2000 | Eggers et al. |
| 6,033,403 A | 3/2000 | Tu et al. |
| 6,042,580 A | 3/2000 | Simpson |
| 6,045,550 A | 4/2000 | Simpson et al. |
| 6,048,329 A | 4/2000 | Thompson et al. |
| 6,049,737 A | 4/2000 | Simpson et al. |
| 6,050,994 A | 4/2000 | Sherman |
| 6,052,612 A | 4/2000 | Desai |
| 6,053,937 A | 4/2000 | Edwards et al. |
| 6,056,744 A | 5/2000 | Edwards |
| 6,059,778 A | 5/2000 | Sherman |
| 6,063,077 A | 5/2000 | Schaer |
| 6,063,082 A | 5/2000 | DeVore et al. |
| 6,064,902 A | 5/2000 | Haissaguerre et al. |
| 6,068,629 A | 5/2000 | Haissaguerre et al. |
| 6,070,094 A | 5/2000 | Swanson et al. |
| 6,071,274 A | 6/2000 | Thompson et al. |
| 6,071,279 A | 6/2000 | Whayne et al. |
| 6,071,281 A | 6/2000 | Burnside et al. |
| 6,071,282 A | 6/2000 | Fleischman |
| 6,074,351 A | 6/2000 | Houser |
| 6,086,581 A | 7/2000 | Reynolds et al. |
| 6,088,610 A | 7/2000 | Littmann et al. |
| 6,096,036 A | 8/2000 | Bowe et al. |
| 6,099,524 A | 8/2000 | Lipson et al. |
| 6,106,522 A | 8/2000 | Fleischman et al. |
| 6,107,699 A | 8/2000 | Swanson |
| 6,115,626 A | 9/2000 | Whayne et al. |
| 6,119,041 A | 9/2000 | Pomeranz et al. |
| 6,120,476 A | 9/2000 | Fung et al. |
| 6,129,724 A | 10/2000 | Fleischman et al. |
| 6,141,576 A | 10/2000 | Littmann et al. |
| 6,146,379 A | 11/2000 | Fleischman et al. |
| 6,146,381 A | 11/2000 | Bowe et al. |
| 6,165,169 A | 12/2000 | Panescu et al. |
| 6,167,291 A | 12/2000 | Barajas et al. |
| 6,171,305 B1 | 1/2001 | Sherman |
| 6,171,306 B1 | 1/2001 | Swanson et al. |
| 6,179,833 B1 | 1/2001 | Taylor |
| 6,200,314 B1 | 3/2001 | Sherman |
| 6,212,426 B1 | 4/2001 | Swanson |
| 6,214,002 B1 | 4/2001 | Fleischman et al. |
| 6,216,043 B1 | 4/2001 | Swanson et al. |
| 6,216,044 B1 | 4/2001 | Kordis |
| 6,217,573 B1 | 4/2001 | Webster |
| 6,217,576 B1 | 4/2001 | Tu et al. |
| 6,226,542 B1 | 5/2001 | Reisfeld |
| 6,231,570 B1 | 5/2001 | Tu et al. |
| 6,238,390 B1 | 5/2001 | Tu et al. |
| 6,241,666 B1 | 6/2001 | Pomeranz et al. |
| 6,241,724 B1 | 6/2001 | Fleischman et al. |
| 6,241,725 B1 | 6/2001 | Cosman |
| 6,241,726 B1 | 6/2001 | Raymond et al. |
| 6,241,727 B1 | 6/2001 | Tu et al. |
| 6,241,728 B1 | 6/2001 | Gaiser et al. |
| 6,241,754 B1 | 6/2001 | Swanson et al. |
| 6,245,067 B1 | 6/2001 | Tu et al. |
| 6,245,089 B1 | 6/2001 | Daniel et al. |
| 6,251,107 B1 | 6/2001 | Schaer |
| 6,256,540 B1 | 7/2001 | Panescu et al. |
| 6,264,664 B1 | 7/2001 | Avellanet |
| 6,267,746 B1 | 7/2001 | Bumbalough |
| 6,290,697 B1 | 9/2001 | Tu et al. |
| 6,293,943 B1 | 9/2001 | Panescu et al. |
| 6,302,880 B1 | 10/2001 | Schaer |
| 6,309,385 B1 | 10/2001 | Simpson |
| 6,312,425 B1 | 11/2001 | Simpson et al. |
| 6,319,251 B1 | 11/2001 | Tu et al. |
| 6,325,797 B1 | 12/2001 | Stewart et al. |
| 6,332,880 B1 | 12/2001 | Yang et al. |
| 6,332,881 B1 | 12/2001 | Carner et al. |
| 6,346,104 B2 | 2/2002 | Daly et al. |
| 6,353,751 B1 | 3/2002 | Swanson |
| 6,360,128 B2 | 3/2002 | Kordis et al. |
| 6,370,435 B2 | 4/2002 | Panescu et al. |
| 6,371,955 B1 | 4/2002 | Fuimaono et al. |
| 6,379,352 B1 | 4/2002 | Reynolds et al. |
| 6,389,311 B1 | 5/2002 | Whayne et al. |
| 6,391,024 B1 | 5/2002 | Sun et al. |
| 6,425,894 B1 | 7/2002 | Brucker et al. |
| 6,428,536 B2 | 8/2002 | Panescu et al. |
| 6,428,537 B1 | 8/2002 | Swanson et al. |
| 6,440,129 B1 | 8/2002 | Simpson |
| 6,447,506 B1 | 9/2002 | Swanson et al. |
| 6,451,015 B1 | 9/2002 | Rittman, III et al. |
| 6,454,758 B1 | 9/2002 | Thompson et al. |
| 6,456,864 B1 | 9/2002 | Swanson et al. |
| 6,460,545 B2 | 10/2002 | Kordis |
| 6,471,693 B1 | 10/2002 | Carroll et al. |
| 6,471,699 B1 | 10/2002 | Fleischman et al. |
| 6,475,213 B1 | 11/2002 | Whayne et al. |
| 6,475,214 B1 | 11/2002 | Moaddeb |
| 6,477,396 B1 | 11/2002 | Mest et al. |
| 6,478,793 B1 | 11/2002 | Cosman et al. |
| 6,485,487 B1 | 11/2002 | Sherman |
| 6,487,441 B1 | 11/2002 | Swanson et al. |
| 6,488,678 B2 | 12/2002 | Sherman |
| 6,490,468 B2 | 12/2002 | Panescu et al. |
| 6,493,586 B1 | 12/2002 | Stahmann et al. |
| 6,500,167 B1 | 12/2002 | Webster, Jr. |
| 6,500,172 B1 | 12/2002 | Panescu et al. |
| 6,514,246 B1 | 2/2003 | Swanson et al. |
| 6,517,536 B2 | 2/2003 | Hooven et al. |
| 6,522,905 B2 | 2/2003 | Desai |
| 6,529,756 B1 | 3/2003 | Phan et al. |
| 6,540,744 B2 | 4/2003 | Hassett et al. |
| 6,542,773 B2 | 4/2003 | Dupree et al. |
| 6,544,262 B2 | 4/2003 | Fleischman |
| 6,551,271 B2 | 4/2003 | Nguyen |
| 6,554,794 B1 | 4/2003 | Mueller et al. |
| 6,558,378 B2 | 5/2003 | Sherman et al. |
| 6,565,511 B2 | 5/2003 | Panescu et al. |
| 6,569,114 B2 | 5/2003 | Ponzi et al. |
| 6,569,162 B2 | 5/2003 | He |
| 6,569,163 B2 | 5/2003 | Hata et al. |
| 6,572,612 B2 | 6/2003 | Stewart et al. |
| 6,574,492 B1 | 6/2003 | Ben-Haim et al. |
| 6,575,997 B1 | 6/2003 | Palmer et al. |
| 6,583,796 B2 | 6/2003 | Jamar et al. |
| 6,597,955 B2 | 7/2003 | Panescu et al. |

(56) References Cited

U.S. PATENT DOCUMENTS

| | | |
|---|---|---|
| 6,602,242 B1 | 8/2003 | Fung et al. |
| 6,605,087 B2 | 8/2003 | Swartz et al. |
| 6,607,505 B1 | 8/2003 | Thompson et al. |
| 6,607,520 B2 | 8/2003 | Keane |
| 6,616,657 B2 | 9/2003 | Simpson et al. |
| 6,625,482 B1 | 9/2003 | Panescu et al. |
| 6,628,976 B1 | 9/2003 | Fuimaono et al. |
| 6,632,223 B1 | 10/2003 | Keane |
| 6,635,056 B2 | 10/2003 | Kadhiresan et al. |
| 6,638,223 B2 | 10/2003 | Lifshitz et al. |
| 6,638,275 B1 | 10/2003 | McGaffigan et al. |
| 6,640,120 B1 | 10/2003 | Swanson et al. |
| 6,652,513 B2 | 11/2003 | Panescu et al. |
| 6,652,517 B1 | 11/2003 | Hall et al. |
| 6,658,279 B2 | 12/2003 | Swanson et al. |
| 6,669,692 B1 | 12/2003 | Nelson et al. |
| 6,669,693 B2 | 12/2003 | Friedman |
| 6,671,533 B2 | 12/2003 | Chen et al. |
| 6,690,972 B2 | 2/2004 | Conley et al. |
| 6,701,180 B1 | 3/2004 | Desai |
| 6,702,811 B2 | 3/2004 | Stewart et al. |
| 6,711,428 B2 | 3/2004 | Fuimaono et al. |
| 6,730,078 B2 | 5/2004 | Simpson et al. |
| 6,738,673 B2 | 5/2004 | Desai |
| 6,740,080 B2 | 5/2004 | Jain et al. |
| 6,743,225 B2 | 6/2004 | Sanchez et al. |
| 6,746,446 B1 | 6/2004 | Hill, III et al. |
| 6,752,804 B2 | 6/2004 | Simpson et al. |
| 6,761,716 B2 | 7/2004 | Kadhiresan et al. |
| 6,771,996 B2 * | 8/2004 | Bowe et al. ............... 600/374 |
| 6,805,131 B2 | 10/2004 | Kordis |
| 6,813,520 B2 | 11/2004 | Truckai et al. |
| 6,814,732 B2 | 11/2004 | Schaer |
| 6,830,576 B2 | 12/2004 | Fleischman et al. |
| 6,866,662 B2 | 3/2005 | Fuimaono et al. |
| 6,893,438 B2 | 5/2005 | Hall et al. |
| 6,893,439 B2 | 5/2005 | Fleischman |
| 6,893,442 B2 | 5/2005 | Whayne |
| 6,916,306 B1 | 7/2005 | Jenkins et al. |
| 6,936,047 B2 | 8/2005 | Nasab et al. |
| 6,939,349 B2 | 9/2005 | Fleischman et al. |
| 6,952,615 B2 | 10/2005 | Satake |
| 6,955,173 B2 | 10/2005 | Lesh |
| 6,960,206 B2 | 11/2005 | Keane |
| 6,961,602 B2 | 11/2005 | Fuimaono et al. |
| 6,964,660 B2 | 11/2005 | Maguire et al. |
| 6,966,908 B2 | 11/2005 | Maguire et al. |
| 6,972,016 B2 | 12/2005 | Hill, III et al. |
| 6,973,339 B2 | 12/2005 | Govari |
| 6,987,995 B2 | 1/2006 | Drysen |
| 7,001,336 B2 | 2/2006 | Mandrusov et al. |
| 7,025,766 B2 | 4/2006 | Whayne et al. |
| 7,029,470 B2 | 4/2006 | Francischelli et al. |
| 7,029,471 B2 | 4/2006 | Thompson et al. |
| 7,044,135 B2 | 5/2006 | Lesh |
| 7,047,068 B2 | 5/2006 | Haissaguerre |
| 7,048,734 B1 | 5/2006 | Fleischman et al. |
| 7,048,756 B2 | 5/2006 | Eggers et al. |
| 7,077,823 B2 | 7/2006 | McDaniel |
| 7,094,235 B2 | 8/2006 | Francischelli |
| 7,099,711 B2 | 8/2006 | Fuimaono et al. |
| 7,099,712 B2 | 8/2006 | Fuimaono et al. |
| 7,113,831 B2 | 9/2006 | Hooven |
| 7,115,122 B1 | 10/2006 | Swanson et al. |
| 7,118,568 B2 | 10/2006 | Hassett et al. |
| 7,122,031 B2 | 10/2006 | Edwards et al. |
| 7,151,964 B2 | 12/2006 | Desai et al. |
| 7,155,270 B2 | 12/2006 | Solis et al. |
| 7,156,843 B2 | 1/2007 | Skarda |
| 7,163,537 B2 | 1/2007 | Lee et al. |
| 2001/0029366 A1 | 10/2001 | Swanson et al. |
| 2001/0039415 A1 | 11/2001 | Francischelli et al. |
| 2001/0044625 A1 | 11/2001 | Hata et al. |
| 2001/0051803 A1 | 12/2001 | Desai et al. |
| 2002/0065465 A1 | 5/2002 | Panescu et al. |
| 2002/0120263 A1 | 8/2002 | Brown et al. |
| 2002/0126036 A1 | 9/2002 | Flaherty et al. |
| 2002/0161422 A1 | 10/2002 | Swanson et al. |
| 2003/0018330 A1 | 1/2003 | Swanson et al. |
| 2003/0093069 A1 | 5/2003 | Panescu et al. |
| 2003/0125730 A1 | 7/2003 | Berube et al. |
| 2003/0181819 A1 | 9/2003 | Desai |
| 2003/0195407 A1 | 10/2003 | Fuimaono et al. |
| 2003/0195501 A1 | 10/2003 | Sherman et al. |
| 2003/0199746 A1 | 10/2003 | Fuimaono et al. |
| 2003/0204185 A1 | 10/2003 | Sherman et al. |
| 2003/0204186 A1 | 10/2003 | Geistert |
| 2004/0015164 A1 | 1/2004 | Fuimaono et al. |
| 2004/0082947 A1 | 4/2004 | Oral et al. |
| 2004/0116921 A1 | 6/2004 | Sherman et al. |
| 2004/0133154 A1 | 7/2004 | Flaherty et al. |
| 2004/0138545 A1 | 7/2004 | Chen et al. |
| 2004/0143256 A1 | 7/2004 | Bednarek |
| 2004/0152980 A1 | 8/2004 | Desai |
| 2004/0158141 A1 | 8/2004 | Scheib |
| 2004/0181139 A1 | 9/2004 | Falwell et al. |
| 2004/0181249 A1 | 9/2004 | Torrance et al. |
| 2004/0182384 A1 | 9/2004 | Alfery |
| 2004/0236324 A1 | 11/2004 | Muller et al. |
| 2004/0247164 A1 | 12/2004 | Furnish |
| 2005/0010095 A1 | 1/2005 | Stewart et al. |
| 2005/0015084 A1 | 1/2005 | Hill et al. |
| 2005/0033137 A1 | 2/2005 | Oral et al. |
| 2005/0065512 A1 | 3/2005 | Schaer |
| 2005/0096644 A1 | 5/2005 | Hall et al. |
| 2005/0101946 A1 | 5/2005 | Govari et al. |
| 2005/0119651 A1 | 6/2005 | Fuimaono et al. |
| 2005/0148892 A1 | 7/2005 | Desai |
| 2005/0177146 A1 | 8/2005 | Sherman |
| 2005/0187545 A1 | 8/2005 | Hooven et al. |
| 2005/0234444 A1 | 10/2005 | Hooven |
| 2005/0240176 A1 | 10/2005 | Oral et al. |
| 2005/0251132 A1 | 11/2005 | Oral et al. |
| 2005/0256521 A1 | 11/2005 | Kozel |
| 2006/0030844 A1 | 2/2006 | Knight et al. |
| 2006/0084966 A1 | 4/2006 | Maguire et al. |
| 2006/0089637 A1 | 4/2006 | Werneth et al. |
| 2006/0095030 A1 | 5/2006 | Avitall et al. |
| 2006/0106375 A1 | 5/2006 | Werneth et al. |
| 2006/0111700 A1 | 5/2006 | Kunis et al. |
| 2006/0111701 A1 | 5/2006 | Oral et al. |
| 2006/0111702 A1 | 5/2006 | Oral et al. |
| 2006/0111703 A1 | 5/2006 | Kunis et al. |
| 2006/0111708 A1 | 5/2006 | Vanney et al. |
| 2006/0122526 A1 | 6/2006 | Berenfeld et al. |
| 2006/0142753 A1 | 6/2006 | Francischelli et al. |
| 2006/0189975 A1 | 8/2006 | Whayne et al. |
| 2006/0195082 A1 | 8/2006 | Francischelli |
| 2006/0206109 A1 | 9/2006 | Swanson |
| 2006/0241366 A1 | 10/2006 | Falwell et al. |
| 2007/0027448 A1 | 2/2007 | Paul et al. |
| 2007/0049816 A1 | 3/2007 | Damiano, Jr. et al. |
| 2007/0083193 A1 | 4/2007 | Werneth et al. |
| 2007/0083194 A1 | 4/2007 | Kunis et al. |
| 2007/0083195 A1 | 4/2007 | Werneth et al. |
| 2007/0106293 A1 | 5/2007 | Oral et al. |

FOREIGN PATENT DOCUMENTS

| | | |
|---|---|---|
| CA | 2327518 | 11/1999 |
| CA | 2328064 | 11/1999 |
| CA | 2328070 | 11/1999 |
| CA | 2371935 | 12/2000 |
| CA | 2222617 C | 7/2002 |
| CA | 2437140 | 6/2004 |
| CA | 2492283 | 7/2005 |
| CA | 2194061 C | 4/2006 |
| CA | 2276755 C | 5/2006 |
| CA | 2251041 C | 6/2006 |
| EP | 428812 B1 | 3/1995 |
| EP | 779059 A | 6/1997 |
| EP | 598742 B1 | 8/1999 |
| EP | 879016 B1 | 10/2003 |
| EP | 1360938 A1 | 11/2003 |

(56) References Cited

FOREIGN PATENT DOCUMENTS

| | | |
|---|---|---|
| EP | 1364677 A2 | 11/2003 |
| EP | 1554986 A1 | 7/2005 |
| EP | 823843 B1 | 10/2005 |
| EP | 1384445 B1 | 2/2006 |
| EP | 1169976 B1 | 4/2006 |
| EP | 1415680 B1 | 4/2006 |
| EP | 1011437 B1 | 5/2006 |
| EP | 1210021 B1 | 5/2006 |
| EP | 1658818 A1 | 5/2006 |
| EP | 1125549 B1 | 6/2006 |
| EP | 1182980 B1 | 6/2006 |
| EP | 1207798 B1 | 6/2006 |
| EP | 1321166 B1 | 7/2006 |
| EP | 1343427 B1 | 7/2006 |
| EP | 1690564 A1 | 8/2006 |
| EP | 828451 B1 | 9/2006 |
| EP | 1070480 B1 | 9/2006 |
| EP | 1014874 B1 | 12/2006 |
| EP | 1383437 B1 | 12/2006 |
| EP | 1455667 B1 | 1/2007 |
| EP | 1750215 A1 | 2/2007 |
| EP | 957794 B1 | 7/2007 |
| JP | 2004188179 A | 7/2004 |
| SU | 1512622 A1 | 10/1989 |
| SU | 1544396 A1 | 2/1990 |
| SU | 1690786 A1 | 11/1991 |
| WO | WO90/06079 A1 | 6/1990 |
| WO | WO93/08756 A1 | 5/1993 |
| WO | WO93/25273 A1 | 12/1993 |
| WO | WO94/12098 A1 | 6/1994 |
| WO | WO96/10961 A1 | 4/1996 |
| WO | WO96/32885 A1 | 10/1996 |
| WO | WO96/32897 A1 | 10/1996 |
| WO | WO96/34558 A1 | 11/1996 |
| WO | WO96/34559 A1 | 11/1996 |
| WO | WO96/34560 A1 | 11/1996 |
| WO | WO96/34567 A1 | 11/1996 |
| WO | WO96/34569 A1 | 11/1996 |
| WO | WO96/34570 A1 | 11/1996 |
| WO | WO96/34650 A1 | 11/1996 |
| WO | WO96/34652 A1 | 11/1996 |
| WO | WO96/34653 A1 | 11/1996 |
| WO | WO96/36860 A2 | 11/1996 |
| WO | WO96/39967 A1 | 12/1996 |
| WO | WO97/15919 A1 | 5/1997 |
| WO | WO97/17893 A1 | 5/1997 |
| WO | WO97/17904 A1 | 5/1997 |
| WO | WO97/25917 A1 | 7/1997 |
| WO | WO97/25919 A1 | 7/1997 |
| WO | WO97/32525 A1 | 9/1997 |
| WO | WO97/36541 A1 | 10/1997 |
| WO | WO97/40760 A1 | 11/1997 |
| WO | WO97/42996 A1 | 11/1997 |
| WO | WO98/18520 A2 | 5/1998 |
| WO | WO98/19611 A1 | 5/1998 |
| WO | WO98/26724 A1 | 6/1998 |
| WO | WO98/28039 A2 | 7/1998 |
| WO | WO98/38913 A1 | 9/1998 |
| WO | WO99/02096 A1 | 1/1999 |
| WO | WO99/56644 A1 | 11/1999 |
| WO | WO99/56647 A1 | 11/1999 |
| WO | WO99/56648 A1 | 11/1999 |
| WO | WO99/56649 A1 | 11/1999 |
| WO | WO00/78239 A2 | 12/2000 |
| WO | WO02/060523 A2 | 8/2002 |
| WO | WO03/041602 A2 | 5/2003 |
| WO | WO03/089997 A2 | 10/2003 |
| WO | WO2005/027765 A1 | 3/2005 |
| WO | WO2005/027766 A1 | 3/2005 |
| WO | WO2005/065562 A1 | 7/2005 |
| WO | WO2005/065563 A1 | 7/2005 |
| WO | WO2005/104972 A2 | 11/2005 |
| WO | WO2006/017517 A2 | 2/2006 |
| WO | WO2006/044794 A2 | 4/2006 |
| WO | WO2006/049970 A2 | 5/2006 |
| WO | WO2006/052651 A1 | 5/2006 |
| WO | WO2006/052905 A2 | 5/2006 |
| WO | WO2006/055654 A1 | 5/2006 |
| WO | WO2006/055658 A1 | 5/2006 |
| WO | WO2006/055733 A1 | 5/2006 |
| WO | WO2006/055741 A1 | 5/2006 |
| WO | WO2007/001981 A2 | 1/2007 |
| WO | WO2007/016123 A2 | 2/2007 |
| WO | WO2007/024785 A2 | 3/2007 |
| WO | WO2007/024983 A2 | 3/2007 |

OTHER PUBLICATIONS

Oral et al., "Segmental ostial ablation to isolate the pulmonary veins during atrial fibrillation: feasibility and mechanistic insights," Circulation, vol. 106, pp. 1256-1262, 2002.

Nademanee et al., "A new approach for catheter ablation of atrial fibrillation: mapping of the electrophysiologic substrate," JACC, vol. 43, No. 11, pp. 2044-2053, 2004.

Wittkampf et al., "Radiofrequency ablation with a cooled porous electrode catheter," (abstract) JACC, vol. 11, No. 2, pp. 17a, Feb. 1988.

Oral et al.; U.S. Appl. No. 11/932,378 entitled "Ablation catheters and methods for their use," filed Oct. 31, 2007.

Sherman et al.; U.S. Appl. No. 12/117,596 entitled RF energy delivery system and method, filed May 8, 2008.

Oral et al.; U.S. Appl. No. 12/176,115 entitled "Atrial ablation catheter adapted for treatment of septal wall arrhythmogenic foci and method of use," filed Jul. 18, 2008.

Kunis et al.; U.S. Appl. No. 12/197,425 entitled "Atrial ablation catheter and method of use," filed Aug. 25, 2008.

Werneth et al.; U.S. Appl. No. 12/245,625 entitled "Ablation catheter," filed Oct. 3, 2008.

* cited by examiner

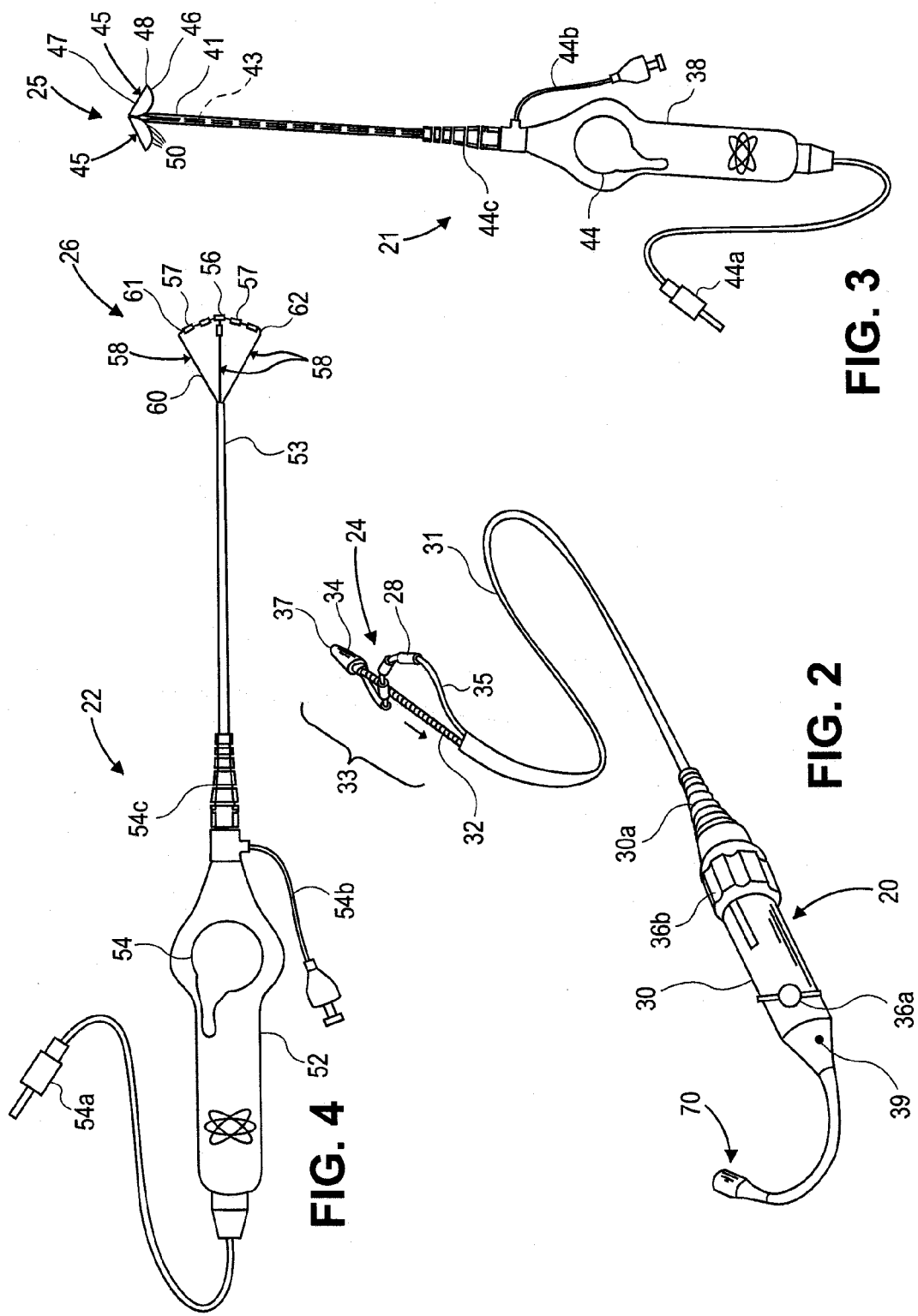

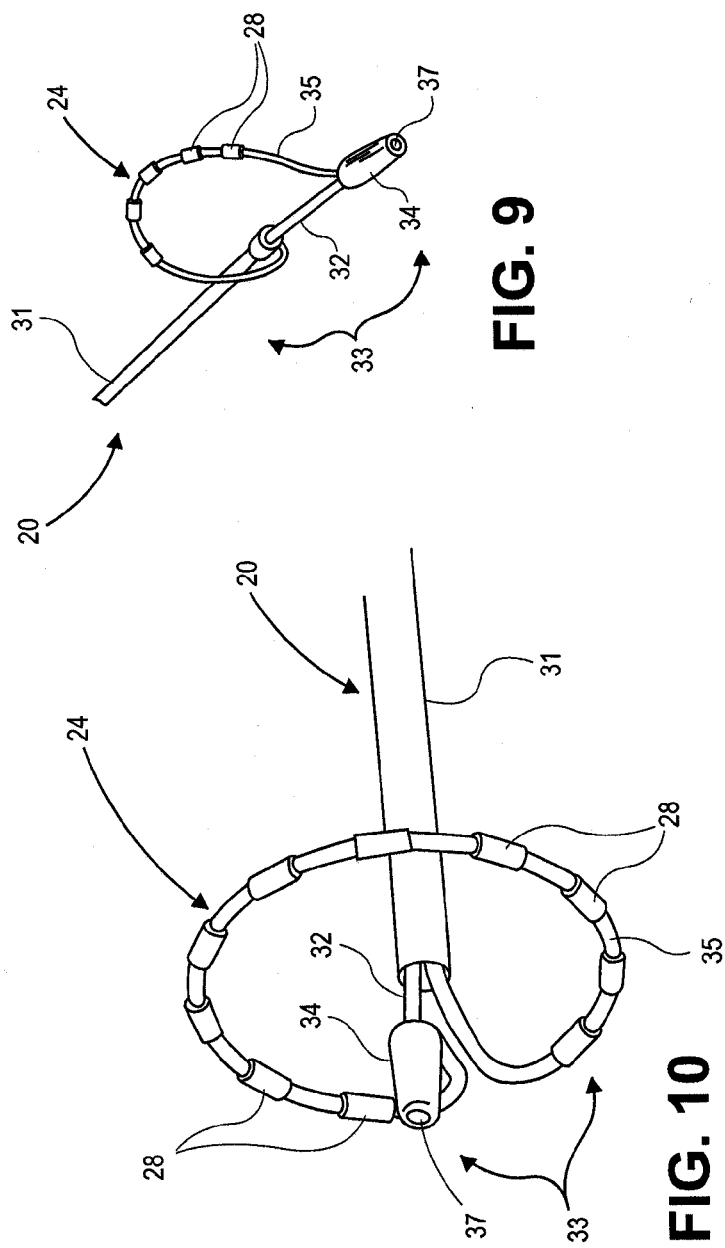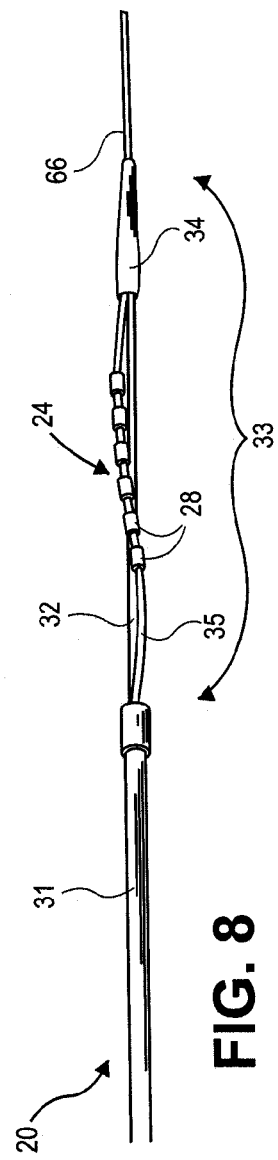

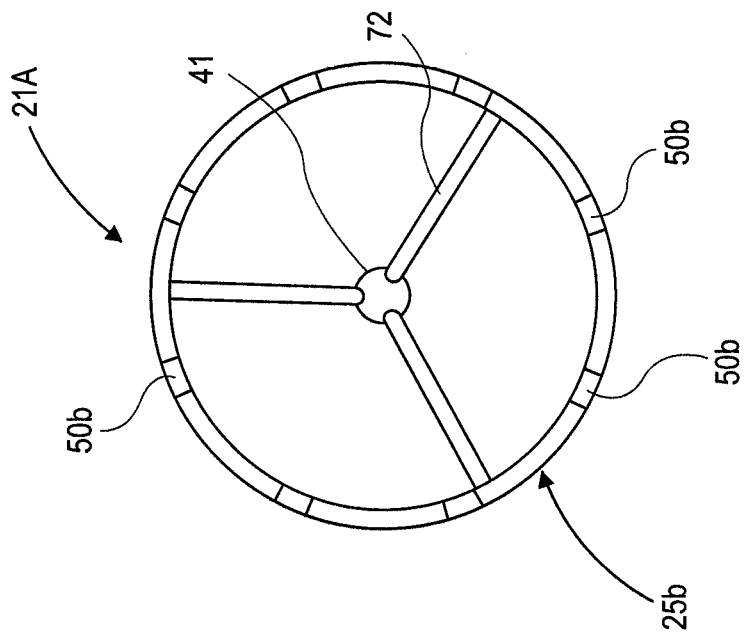
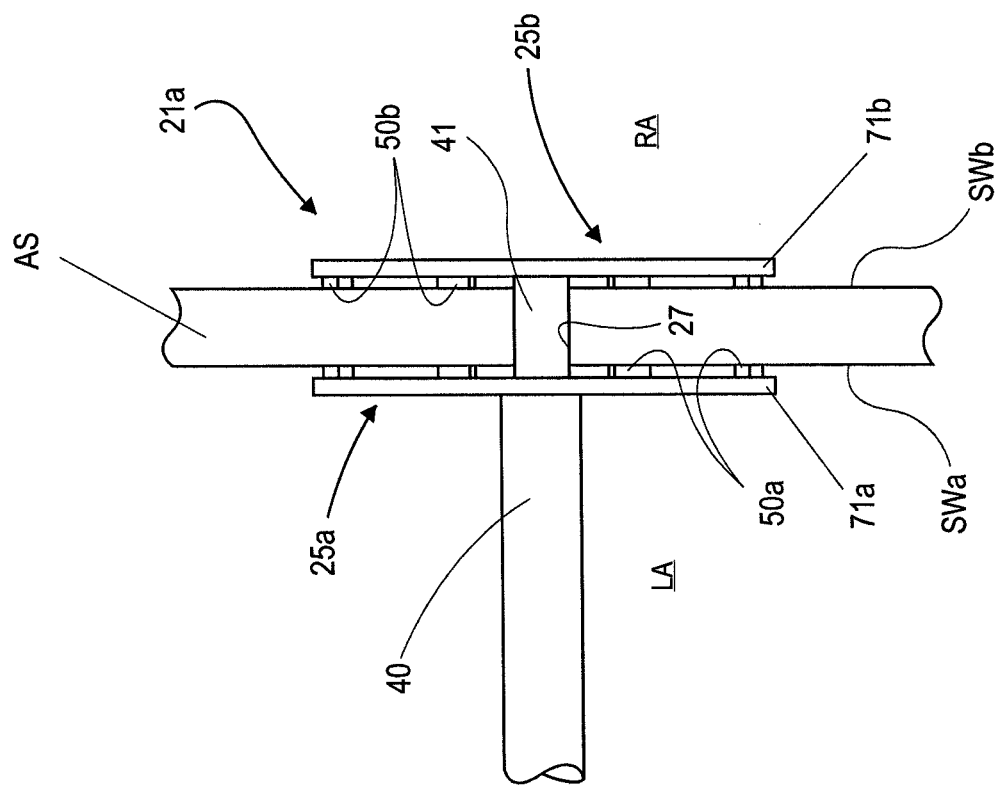

ABLATION THERAPY SYSTEM AND METHOD FOR TREATING CONTINUOUS ATRIAL FIBRILLATION

CROSS-REFERENCE TO RELATED APPLICATION

This application claims the benefit of U.S. Provisional Application No. 60/928,788 filed May 11, 2007, which is incorporated by reference herein in its entirety.

BACKGROUND OF THE INVENTION

Atrial fibrillation is a form of cardiac arrhythmia where there is disorganized electrical conduction in the atria causing rapid uncoordinated contractions that result in ineffective pumping of blood into the ventricle and a lack of synchrony. During atrial fibrillation, the atrioventricular node receives electrical impulses from numerous locations throughout the atria instead of only from the sinus node. This overwhelms the atrioventricular node into producing an irregular and rapid heartbeat. As a result, blood may pool in the atria increasing the risk for blood clot formation. The major risk factors for atrial fibrillation include age, coronary artery disease, rheumatic heart disease, hypertension, diabetes, and thyrotoxicosis. Atrial fibrillation affects 7% of the population over age 65.

Atrial fibrillation treatment options are somewhat limited. For instance, a lifestyle change only assists individuals with lifestyle related atrial fibrillation, and medication therapy assists only in the management of atrial fibrillation symptoms. In the latter, medication therapy may present side effects more dangerous than atrial fibrillation, and fail to cure atrial fibrillation. Electrical cardioversion attempts to restore sinus rhythm, even if successful acutely, often result in recurrence of atrial fibrillation. In addition, if there is a blood clot in the atria, cardioversion may cause the clot to leave the heart and travel to the brain (leading to stroke) or to some other part of the body.

One of the more recent procedures for treating cardiac arrhythmias is catheter ablation therapy. Physicians make use of specialized ablation catheters to gain access into interior regions of the body. Catheters with tip electrodes or other ablating devices are used to create ablation lesions that physiologically alter the ablated tissue without removal thereof, and thereby disrupt and/or block electrical pathways through the targeted tissue. In the treatment of cardiac arrhythmias, a specific area of cardiac tissue having aberrant electrically conductive pathways, such as atrial rotors, emitting or conducting erratic electrical impulses, is initially localized. A user (e.g., a physician) directs a catheter through a main vein or artery into the interior region of the heart that is to be treated. The ablating element or elements are next placed near the targeted cardiac tissue that is to be ablated, such as a pulmonary vein ostium or atrum.

While the currently available methods and devices for catheter ablation therapy are becoming more widely adopted, certain forms of atrial fibrillation, such as recurrent atrial fibrillation, and in particular, continuous atrial fibrillation, are considered very difficult to effectively treat applying this technique. Any patient with two or more identified episodes of atrial fibrillation is said to have recurrent atrial fibrillation.

Currently, the most common ablation catheter applied to treat continuous atrial fibrillation is a single-point tip-electrode ablation catheter that forms single-point ablation lesion. Such a catheter-based ablation therapy using single-point tip ablation catheters have shown only limited success, and proven tedious, extremely difficult to use, time-consuming, and often ineffective and impractical. There is therefore a need for improved atrial ablation products and procedures that effectively and efficiently treat continuous atrial fibrillation in a safe manner.

SUMMARY OF THE INVENTION

The present invention provides methods and intraluminal ablation therapy systems for treating continuous atrial fibrillation (which includes permanent, persistent, chronic, and any other form of non-paroxysmal atrial fibrillation). In some embodiments the ablation therapy system includes a Multi-Channel RF Ablation Generator, an ECG interface, and an assembly of at least two ablation catheters. The first catheter is preferably a pulmonary vein ablation catheter adapted to perform a pulmonary vein ablation procedure, while the second catheter is preferably a septal wall ablation catheter adapted to perform a septal wall ablation procedure. A third catheter may also be used, such as an atrial wall ablation catheter, which is adapted to perform an atrial wall ablation procedure. The therapy systems of the present invention further includes an ECG interface that operably couples and interfaces the assembly of ablation catheters to both an ECG unit and the RF Ablation Generator.

One embodiment of the invention is a systematic method of treating continuous atrial fibrillation. The method includes transseptally accessing a left atrium of a heart of a patient through a puncture in an atrial septum, ablating tissue surrounding one or more pulmonary veins to treat aberrant conductive pathways therethrough, and ablating septal tissue surrounding the puncture to treat aberrant conductive pathways therethrough. Ablating the septal tissue surrounding the puncture can occur after ablating the tissue surrounding one or more pulmonary veins.

Performing a pulmonary vein ablation procedure further includes sensing electrical signals of the pulmonary vein ostial tissue through one or more electrodes of an electrode array of a first catheter. Upon determining that the electrodes of the electrode array of the first catheter are disposed over an aberrant signal such as an arrhythmogenic focus of the pulmonary vein ostial tissue, energy is passed (into the tissue) through the electrodes of the electrode array to ablate a portion thereof. Similarly, performing an atrial septum ablation procedure includes sensing electrical signals of the left atrial septum tissue through one or more electrodes of an electrode array of a second catheter. Upon determining that the electrodes of the electrode array of the second catheter are disposed over an aberrant signal of the atrial septum tissue, energy is passed through the electrode array of the second catheter to ablate a portion thereof.

In accordance with another specific configuration, performing a pulmonary vein ablation procedure further includes advancing a first catheter along a guide wire that is selectively inserted into one of the pulmonary veins.

Yet another specific embodiment includes, after performing the left atrial septum ablation procedure, performing a subsequent endocardial pulmonary vein ablation procedure on the pulmonary vein ostial tissue surrounding one or more pulmonary veins in a manner treating aberrant re-conductive pathways therethrough.

After performing the atrial septum ablation procedure, the method can include performing a left atrial wall ablation procedure to ablate at least one of the roof wall, the posterior wall, the superior wall and the floor wall (including the mitral isthmus) of the left atrium in a manner treating aberrant conductive pathways therethrough.

Another embodiment of the invention is a systematic method for treating continuous atrial fibrillation. The method includes transseptally accessing the left atrium through a puncture in the atrial septum of the heart of a patient with a first catheter having an electrode array disposed on the distal end thereof. A pulmonary vein ablation procedure is performed on the pulmonary vein ostial tissue substantially surrounding one or more pulmonary veins by advancing the electrode array toward and into contact with the pulmonary vein ostial tissue. After ablating the ostial tissue, the method includes transseptally accessing the left atrium with a second catheter by advancing an electrode array disposed on the end of the second catheter through the septal puncture. Applying the second catheter, an atrial septum ablation procedure is performed on atrial septum tissue substantially surrounding the septal puncture by retracting the second catheter electrode array into contact with the atrial septum tissue.

The methods can be performed using a single transseptal sheath to provide access to a plurality of ablation catheters. One sheath may be used because each of the plurality of ablation catheters may be used to map tissue as well as ablate tissue, thus avoiding the need for both a mapping sheath and an ablation sheath.

Performing a pulmonary vein ablation procedure further includes selectively moving the electrode array of the first catheter to other areas of the pulmonary vein ostial tissue surrounding the one or more pulmonary veins, and repeating the sensing of electrical signals and ablating of the pulmonary vein ostial tissue. Contiguous lesions are created by rotating the electrode array about 90° about an axis of the first catheter after each repeat cycle.

In one specific embodiment, the pulmonary vein ablation procedure further includes ablating the ostial tissue surrounding the Left Superior Pulmonary Vein, the Left Inferior Pulmonary Vein, the Right Superior Pulmonary Vein, and the Right Inferior Pulmonary Vein. More specifically, the pulmonary vein ablation procedure is also performed in the order of the Left Superior Pulmonary Vein first, followed by ablating the ostial tissue surrounding at the Left Inferior Pulmonary Vein, which is then followed by the Right Superior Pulmonary vein, and finally the Right Inferior Pulmonary Vein.

In another embodiment, transseptally accessing the left atrium with a first catheter is performed by advancing the distal end of the first catheter through a lumen of a transseptal sheath that extends through the puncture of the atrial septal wall. Prior to performing a pulmonary vein ablation procedure, the method includes withdrawing the transseptal sheath proximally until the distal end thereof is removed from the left atrium of the heart. More particularly, withdrawing the transseptal sheath includes retracting the transseptal sheath proximally such that a minimal portion extends into the left atrium or until the distal end thereof is contained in the right atrium of the heart.

In another specific embodiment, prior to performing the atrial septum ablation procedure, the first catheter is retracted, in the deployed condition, toward the atrial septum such that the electrode array contacts the septal wall. From this orientation, electrical signals of the atrial septum tissue are sensed through the electrodes of the electrode array of the first catheter; and upon determining that the electrodes of the electrode array of the first catheter are disposed over an aberrant signal of the atrial septum tissue, an ablation procedure is performed using the second catheter.

In one configuration, the atrial septum ablation procedure is further performed by selectively moving the electrode array of the second catheter to other areas of the atrial septal tissue surrounding septal puncture, and repeating the sensing electrical signals and ablating of the atrial septal tissue. The selectively moving the electrode array of the second catheter includes incrementally rotating the electrode array about an axis of the second catheter after each repeat cycle. Such incremental rotation of the electrode array about the axis of the second catheter is in the range of about 5° to about 15°.

In still another embodiment, the first catheter is a PVAC device having an electrode array configured to ablate tissue in a distal facing direction, and the second catheter is a MASC device having an electrode array configured to ablate tissue in a proximal facing direction. The first catheter, in the deployed condition, is capable of increasing and decreasing the diameter of the spiral of the carrier assembly within a first range of diameters up to a first catheter maximum diameter. Moreover, the method further includes transseptally accessing the Left Atrium (LA), through the puncture in the atrial septum, with a fourth catheter having an electrode array substantially similar to that of the first catheter, but having a carrier assembly, in a deployed condition, capable of increasing and decreasing the diameter of a spiral of the carrier assembly within a second range of diameters up to a fourth catheter maximum diameter. The fourth catheter maximum diameter is selected to be either smaller or larger than the first catheter maximum diameter. The method further includes performing a pulmonary vein ablation procedure on the pulmonary vein ostial tissue substantially surrounding one or more pulmonary veins by advancing the electrode array of the third catheter toward and into contact with the pulmonary vein ostial tissue.

After performing the atrial septum ablation procedure, the method includes transseptally accessing the Left Atrium (LA) through the puncture in the atrial septum with a third catheter having an electrode array disposed on the distal end thereof. A left atrial wall ablation procedure is performed by advancing the electrode array toward and into contact with at least one of the roof wall, the posterior wall, the superior wall and the floor wall of the left atrium of the heart.

The performing the left atrial wall ablation procedure includes sensing electrical signals of the left atrial wall tissue through the electrodes of the electrode array of the third catheter. Upon determining that the electrodes of the electrode array of the third catheter are disposed over an aberrant signal of the left atrial wall tissue, energy is passed through the electrode array to ablate a portion thereof.

To perform the left atrial wall ablation procedure, the method further includes selectively moving the electrode array to other regions such as the roof wall, the posterior wall, the superior wall and the floor wall of the Left Atrium (LA), and repeating the sensing of electrical signals procedure and ablation procedure of the left atrial wall tissue. The preferred order of atrial wall ablation includes ablating the left atrial roof wall tissue first, followed by ablating the left atrial posterior wall tissue. This is then followed by ablating the left atrial superior wall tissue, and subsequently ablating the left atrial floor wall tissue In another specific embodiment, after performing the left atrial wall ablation procedure, the method includes transseptally accessing the Left Atrium (LA), through the puncture in the atrial septum, with a single point tip ablation catheter having a single electrode disposed on the distal end thereof; and performing a touch-up ablation procedure with the single point tip ablation catheter.

Yet another aspect of the present invention includes an assembly of ablation catheters provided for treating continuous atrial fibrillation through intraluminal ablation therapy. This assembly includes a Pulmonary Vein ablation Catheter formed and dimensioned to transseptally access the Left Atrium of a patient's heart. The Pulmonary Vein ablation Catheter includes an electrode array disposed on the distal end thereof configured to perform a pulmonary vein ablation procedure. A Septal wall ablation Catheter is also provided that is formed and dimensioned to transseptally access the Left Atrium of a patient's heart. The Septal wall ablation Catheter includes an electrode array disposed on the distal end thereof configured to perform an atrial septum ablation procedure. Finally, a Left Atrial Wall ablation Catheter is included that formed and dimensioned to transseptally access the Left Atrium of a patient's heart. The Left Atrial Wall ablation Catheter has an electrode array disposed on the distal end thereof configured to perform a touch-up ablation procedure on portions of the Left Atrial Wall of the patient's heart.

Still another aspect of the present invention includes an intraluminal ablation therapy system for systematically treating continuous atrial fibrillation. This system includes an assembly of ablation catheters includes a Pulmonary Vein ablation Catheter, a Septal wall ablation Catheter and an Atrial wall ablation Catheter. The Pulmonary Vein ablation Catheter includes an electrode array formed and dimensioned to facilitate the electrical isolation (hereinafter including isolation and/or elimination) of aberrant signals of the Pulmonary Veins through ablation therapy. The Septal wall ablation Catheter includes an electrode array formed and dimensioned to facilitate the electrical isolation of aberrant signals of the Septum through ablation therapy. Finally, the Atrial wall ablation Catheter includes an electrode array formed and dimensioned to facilitate the electrical isolation of aberrant signals of the Left Atrial Wall through ablation therapy.

The ablation therapy system further includes a RF Generator configured to deliver both Bipolar and Monopolar ablative energy to the catheters, and an ECG interface coupling an ECG monitoring unit and the RF generator. In one specific embodiment, the ECG interface unit is configured to isolate the RF generator from the ECG monitoring unit. In particular, the circuitry electrically isolates potentially damaging signals generated by the RF generator from the ECG unit, as well as shielding the unit from other electrical noise.

The generator is adapted to deliver energy in a bipolar mode, a monopolar mode, or the generator can deliver energy in a mode which combines bipolar and monopolar delivery. The generator is adapted to deliver a combination of bipolar and monopolar RF energy to the electrode array in bipolar to monopolar ratios of at least 4:1, 2:1, and 1:1.

In some embodiments the catheter electrode arrays are adapted to measure the temperature of atrial tissue adjacent the electrode (with, for example, a thermocouple). The generator monitors the temperature measured by the electrode. The generator then delivers energy to the electrode based on the measured temperature. A temperature feedback loop is thereby generated between the electrode and the generator. The generator can be adapted to independently monitor the temperature of atrial tissue measured by more than one electrode in the array, and the RF generator can then generate and deliver RF energy to each of the electrodes based on the independently monitored temperatures. When operating in bipolar mode, the generator can selectively limit the amount of energy being delivered to an electrode if the electrode is measuring the adjacent atrial tissue to be higher than the temperature of the tissue measured by the second electrode in the pair of electrodes.

BRIEF DESCRIPTION OF THE DRAWINGS

The assembly of the present invention has other objects and features of advantage which will be more readily apparent from the following description of the best mode of carrying out the invention and the appended claims, when taken in conjunction with the accompanying drawings, in which:

FIG. 2 is a top perspective view of one embodiment of a Pulmonary Vein Ablation Catheter of the ablation therapy system of FIG. 1.

FIG. 3 is a top perspective view of one embodiment of a Septal Wall Ablation Catheter of the ablation therapy system of FIG. 1.

FIG. 4 is a top perspective view of one embodiment of an Atrial Wall Ablation Catheter of the ablation therapy system of FIG. 1.

FIG. 8 is a fragmentary side elevation view of a distal portion the Pulmonary Vein Ablation Catheter of FIG. 2, illustrating the electrode array in a near linear transport configuration.

FIG. 9 is a fragmentary front perspective view of the distal portion the Pulmonary Vein Ablation Catheter of FIG. 2, illustrating the electrode array in a partially deployed condition.

FIG. 10 is an enlarged, fragmentary, front perspective view the distal portion the Pulmonary Vein Ablation Catheter of FIG. 2, illustrating the electrode array in a fully deployed condition.

FIG. 19 is an enlarged, fragmentary, side elevation view, in partial cross-section, of a distal portion of an alternative embodiment Atrial Wall Ablation Catheter, having opposed electrode arrays configured to simultaneously ablate the Atrial Septum from both the Right Atrium and the Left atrium.

FIG. 20 is a front plan view of the electrode array of the alternative embodiment Atrial Wall Ablation Catheter shown in FIG. 19.

DETAILED DESCRIPTION

Figure 1:
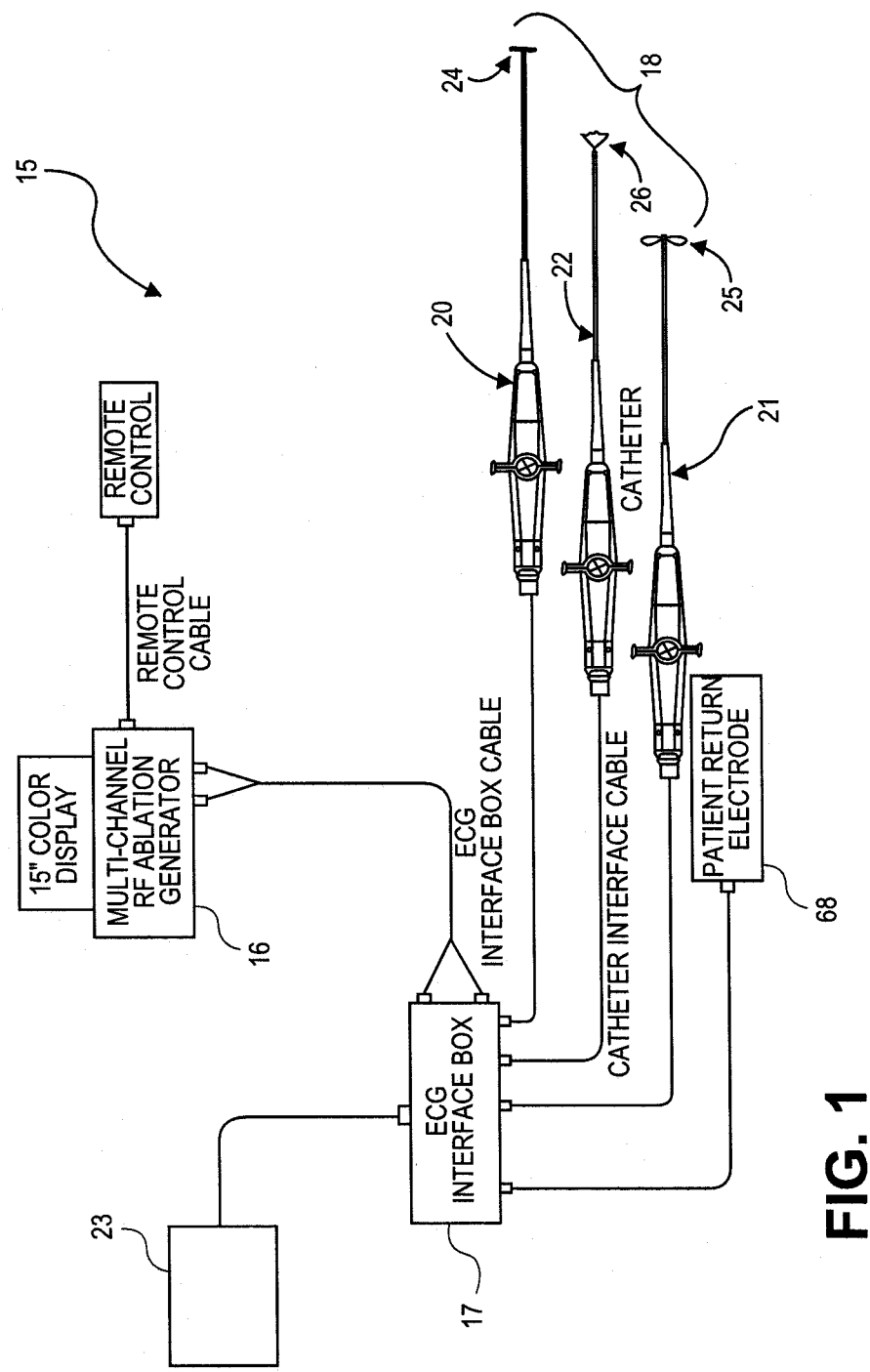
FIG. 1 is schematic diagram of an intraluminal ablation therapy system for treating Continuous Atrial Fibrillation in accordance with the present invention.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the claims. It will be noted here that for a better understanding, like components are designated by like reference numerals throughout the various figures.

Referring to FIGS. 1-7, an intraluminal ablation therapy system 15, is provided for systematically treating continuous atrial fibrillation. "Continuous atrial fibrillation" as used herein includes permanent, persistent, chronic, and any other form of non-paroxysmal atrial fibrillation.

Ablation therapy system 15 includes a Multi-Channel RF Ablation Generator 16, an ECG interface 17, and assembly 18 of three ablation catheters 20, 21 and 22 described below. While three ablation catheters are shown, the system may only have two catheters. The ECG interface 17 operably couples and interfaces assembly 18 to both ECG unit 23 and RF Ablation Generator 16. Generator 16 also includes a user-interface, such as the remote control shown in FIG. 1. As shown in FIGS. 2-4, assembly 18 of ablation catheters includes a first catheter 20 (preferably used as a Pulmonary Vein Ablation Catheter), a second catheter 21 (preferably used as a Septal wall ablation Catheter), and a third catheter 22 (which can be used as a Left Atrial Wall ablation Catheter), all of which are formed and dimensioned to intraluminally and transseptally access the Left Atrium LA of a patient's heart H. Pulmonary Vein Ablation Catheter 20 includes electrode array 24 disposed near or substantially on the distal end thereof and is configured to perform a pulmonary vein ablation procedure (i.e., ablate tissue to treat aberrant conductive pathways through tissue) at or around the ostium of the Pulmonary Veins PV (see FIG. 5). As used herein "pulmonary vein tissue" or "pulmonary tissue" includes pulmonary vein ostia as well as the antrum of a pulmonary vein. In addition, references herein to "ostium" or "ostia" of a pulmonary vein generally refer to both the ostium as well as an antrum of the pulmonary vein. Septal Wall Ablation Catheter 21 includes electrode array 25 disposed near or substantially on the distal end thereof and is configured to perform an atrial septum ablation procedure (see FIG. 6). Left Atrial Wall Ablation Catheter 22 includes electrode array 26 disposed substantially on the distal end thereof and is configured to perform a tissue ablation procedure on one or more portions of the Left Atrial Wall of the patient's heart (see FIG. 7).

The present invention also includes a method for treating continuous atrial fibrillation through a systematic application of these or similarly adapted ablation catheters. The catheters each comprise an electrode array disposed at a location in the distal region of the catheters that allows the arrays to ablate specific types of atrial tissue. The method includes transseptally accessing the Left Atrium LA of a heart H of a patient, through a puncture 27 in the Atrial Septum AS with a first catheter 20 (see FIGS. 5A-5D). At or near the distal end of first catheter 20 (shown as the pulmonary vein ablation catheter described herein) is electrode array 24 comprising two or more electrodes 28 (see FIG. 2).

Figure 5A:
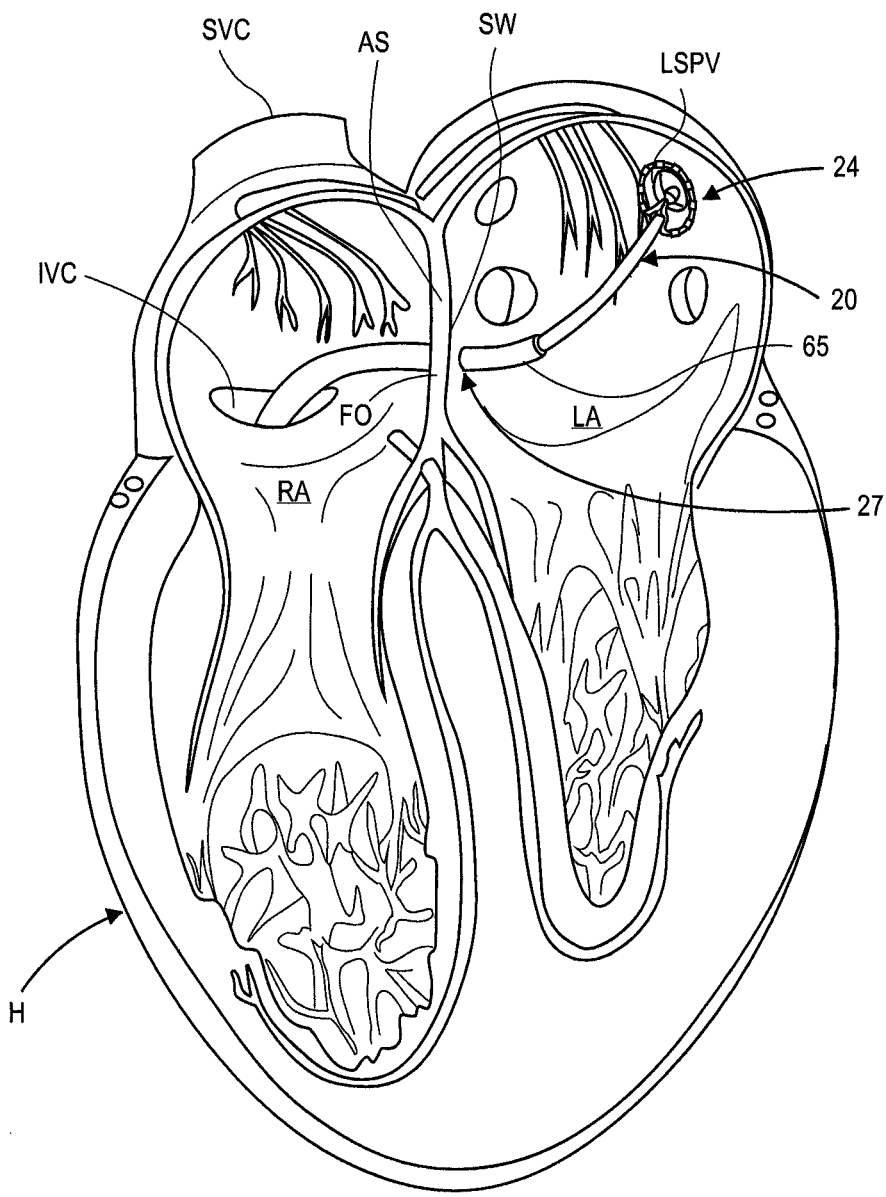
FIGS. 5A-5D is a sequence of front elevation views, in cross-section, of a patient's Heart (H) undergoing Pulmonary Vein ablation therapy, in accordance with the present invention, with the Pulmonary Vein Ablation Catheter of FIG. 2 on the Left Superior Pulmonary Vein (LSPV), the Right Superior Pulmonary Vein (RSPV), the Left Inferior Pulmonary Vein (LIPV), and finally, the Right Inferior Pulmonary Vein (RIPV).
Figure 5B:
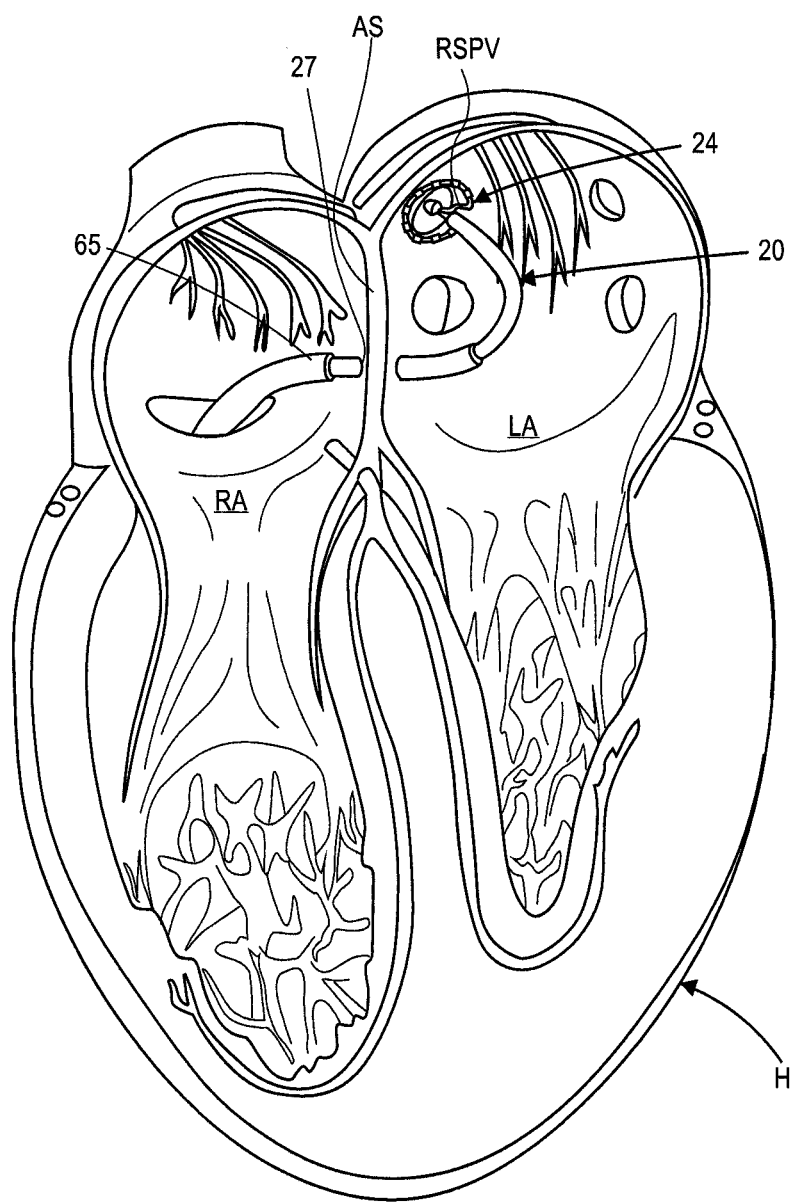
Figure 5C:
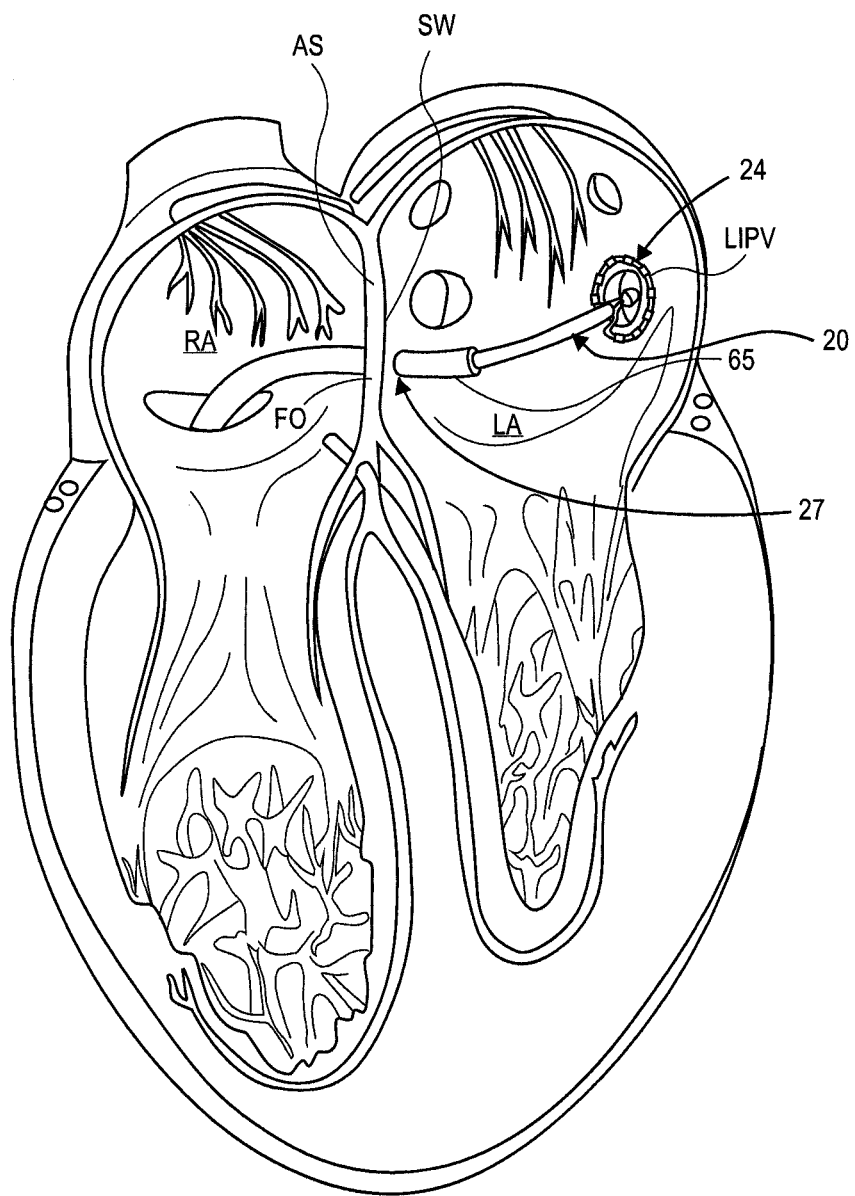
Figure 5D:
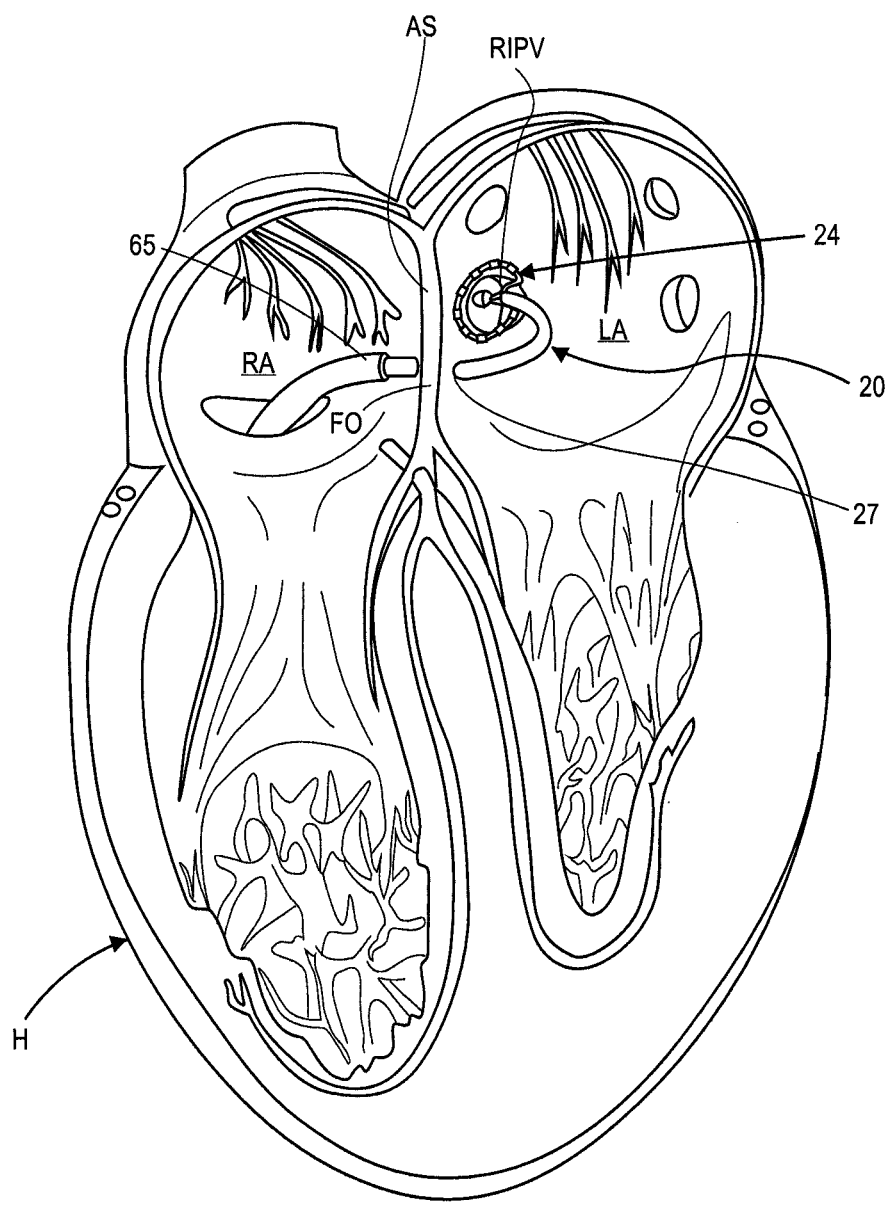

The method also includes performing a pulmonary vein ablation procedure on the pulmonary vein ostial tissue substantially surrounding one or more pulmonary veins PV (e.g., Left Superior Pulmonary Vein LSPV as shown in FIG. 5A, Right Superior Pulmonary Vein RSPV as shown in FIG. 5B, Left Inferior Pulmonary Vein LIPV as shown in FIG. 5C, and Right Inferior Pulmonary Vein RIPV as shown in FIG. 5D). The method includes ablating the tissue surrounding one or more of the pulmonary veins by advancing the electrode array distally toward and into contact with the pulmonary vein ostial tissue.

Figure 6:
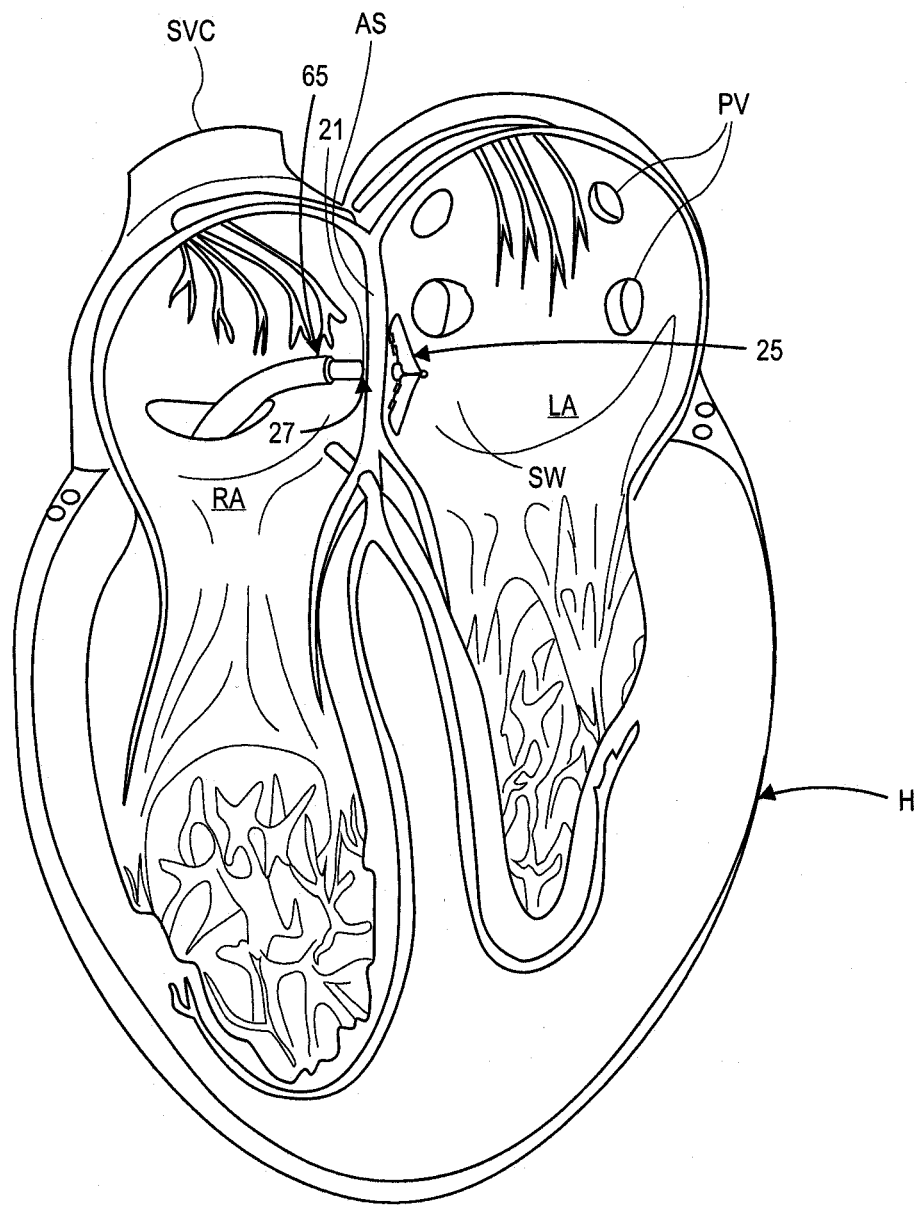
FIG. 6 is a front elevation view, in cross-section, of the patient's Heart (H) undergoing an Atrial Septum ablation procedure, in accordance with the present invention, with the Septal Wall Ablation Catheter of FIG. 3.

The method further includes transseptally accessing the Left Atrium LA with a second catheter 21 (see FIG. 6) by advancing the electrode array 25 through the puncture 27. Once properly oriented, the method includes ablating septal tissue surrounding the puncture to treat aberrant conductive pathways therethrough (i.e., performing an Atrial Septum ablation procedure on the Atrial Septum tissue substantially surrounding the puncture 27). The septal tissue is ablated by retracting the second catheter electrode array 25 proximally toward and into contact with the Atrial Septum tissue, as shown in FIG. 6.

It has been found that by initially ablating pulmonary vein tissue and septal tissue (in either order), the likelihood of a successful treatment for continuous atrial fibrillation increases. Stated alternatively, the likelihood of success for treating continuous atrial fibrillation has been found to increase when the treatment begins with the combination of treating pulmonary vein tissue and septal tissue. Additional atrial tissue may then be ablated after pulmonary vein tissue and septal tissue have been ablated. While the order of treatment may be described herein as pulmonary vein tissue ablation followed by septal tissue ablation, the invention is not limited to this specific order of ablation. It is the combination of ablating these two types of tissue, rather than a specific order, that has been found to increase the likelihood of success for the ablation treatment. Ablating pulmonary vein tissue followed by ablation of septal tissue is merely one specific embodiment of the invention.

There are a number of advantages that have been found by beginning the ablation procedure with the specific combination of ablating pulmonary vein tissue and septal tissue. For example, the specific combination has been found to increase the efficiency of the procedure itself, including a decrease in the time that is needed to treat the patient. Successful treatment of the patient includes measure of acute success, such as the patient is in substantially normal sinus rhythm, the pulmonary veins are adequately isolated, and/or there is a lack of aberrant signals found in the left atrium and left atrial septum. Successful treatment of the patient also includes chronic success, such as the patient remaining in normal sinus rhythm for longer periods of time, for example, for 6 months or more.

It has been observed that after ablating tissue surrounding one or more pulmonary veins, a condition known as Pulmonary Vein re-conduction may occur in which tissue that was not sufficiently ablated begins to re-conduct aberrant current. This re-conduction has been found to occur generally within about 20 to about 40 minutes after ablating the pulmonary vein tissue. Accordingly, by performing a Pulmonary Vein ablation procedure (also referred to as an intraluminal Pulmonary Vein isolation procedure) followed by an Left Atrial Septum ablation procedure (also referred to as an intraluminal Left Atrial Septum isolation procedure) ample time is provided to then observe any re-conduction currents of and around the Pulmonary Veins. This is one advantage to ablating the pulmonary vein tissue before the septal tissue.

A Pulmonary Vein re-mapping procedure (to check for Pulmonary Vein re-conduction) can be performed after the Left Atrial Septum ablation procedure, after a Left Atrial Wall ablation procedure, or at a subsequent step in the overall procedure. The Pulmonary Vein re-mapping procedure is preferably performed with the patient in normal sinus rhythm, usually after a Cardioversion procedure. If the re-mapping procedure confirms that Pulmonary Vein re-conduction has occurred, a second Pulmonary Vein ablation procedure is performed. Alternatively or additionally, interrogation of intercardiac electrograms to evaluate if PV potentials exist is performed by pacing (providing pacing energy) the coronary sinus of the Right Atrium (RA), such as by using a multi-electrode catheter placed in the coronary sinus. In a preferred embodiment, first catheter 20 is positioned at one of the pulmonary vein ostia during the coronary sinus pacing. Techniques which provide pacing energy to the distal coronary sinus can discriminate true PV aberrant signals (which need to be ablated) vs. far-field potentials which are often mistaken for PV potentials, and are unnecessarily ablated. This is described in more detail in Pulmonary vein-related maneuvers: Part 1, Samuel J. Asirvatham, Heart Rhythm Society, pgs 538-544.

In one specific embodiment after ablating the septal tissue (FIG. 6), the method further includes transseptally accessing the Left Atrium through the puncture 27 with either the first catheter or a catheter (not shown) preferably having an electrode array that has a geometric layout substantially similar to that of the first catheter. The electrode array may have a larger or smaller diameter than the first catheter (or have a slightly different geometric layout of electrodes such as different electrode spacing), which provides the ability to perform a slightly different ablation procedure on the Pulmonary Vein ostial tissue. Alternatively, this catheter may comprise an electrode array having a different geometric arrangement than that of the first catheter with either the same or different diameter thereof. In this specific embodiment, the method therefore also includes ablating Pulmonary Vein ostial tissue substantially surrounding one or more Pulmonary Veins after ablating the septal tissue.

In some embodiments, a patient's continuous atrial fibrillation may be successfully treated by ablating only pulmonary vein tissue and left atrial septal tissue. In other instances, however, additional ablation may be needed, such as treatment of foci, rotors or drivers of the Left Atrial Walls, or other locations in the heart. Accordingly, in one specific embodiment, after performing the Pulmonary Vein ablation procedure and the Atrial Septum ablation procedure, the method also includes transseptally accessing the Left Atrium LA, through the puncture 27 in the Atrial Septum AS, with third catheter 22 (see FIGS. 4 and 7) adapted to perform an Atrial Wall ablation procedure on regions of the Left Atrial Wall. More particularly, the Atrial Wall ablation procedure is performed on specific regions of the Left Atrial Wall that include the Roof Wall RW, the Posterior Wall PW, the Superior Wall SW, and the Floor Wall FW of the Left Atrium LA. Ablating the tissue is performed by advancing electrode array 26 of third catheter 22 toward and into contact with at least one of these Left Atrial Wall regions of the Heart H (see FIG. 7).

Accordingly, by ablating atrial tissue with ablation catheters 20-22 in the manner described above (pulmonary vein ablation and left atrial septal ablation followed by left atrial wall ablation), a complete treatment has been developed that successfully treats continuous atrial fibrillation, a condition that has not previously been effectively or efficiently treated through catheter ablation therapy. This lack of success is especially true for the conventional single tip catheters used today to treat continuous atrial fibrillation conditions (e.g. single point catheters that deliver Monopolar RF energy).

One of the advantages of ablating atrial tissue in the manner described herein is a reduction in the time required to treat the patient. Using a single tip catheter to successfully ablate atrial tissue typically requires about 4-8 hours. Ablating atrial tissue according to the inventions described herein can be performed in less than about 3 hours, and more particularly in less than about 2.5 hours.

Not only is this a significant improvement in the time required to perform such a procedure, but the therapeutic success rates have improved. A multi-center clinical trial using the system and method of the present invention has been conducted. In a cohort of patients receiving one or two of these procedures, at six months follow-up, 34 of 45 (75.6%) patients were in 100% sinus rhythm. At six months and as tested by wearing a Holter Monitor for 7 days, 37 of those 45 (82.2%) patients were free of any AF episodes of more than 60 second duration (i.e. all episodes self-resolved).

In addition, ablating tissue to create a continuous lesion around the pulmonary vein ostium is difficult to perform and visualize using a single tip catheter, and often require expensive visualization equipment to create three-dimensional imaging of the heart. The catheters described herein can overcome this difficulty and can be effectively used without the need for three-dimensional visualization.

While the specialized ablation catheters 20, 21 and 22 are particularly adapted to perform the designated atrial ablation procedures described herein, it will be appreciated that alternative, similarly configured ablation catheters may also be used to ablate tissue in the same systematic order to treat continuous atrial fibrillation, albeit perhaps not as efficiently and effective as the catheters described herein.

In one embodiment, PVAC catheter 20, MASC catheter 21 and the T-VAC catheter (as described in reference to FIGS. 22 and 23) are provided in an assembly. The preferred order of use in this embodiment is PVAC catheter 20 ablating pulmonary vein tissue, MASC catheter 21 ablating left atrial septal tissue, followed by the T-VAC catheter.

The catheters all typically include an elongated, flexible outer catheter tube. The catheters also include an array of electrodes disposed near, on, or substantially on the distal end thereof. The arrays are arranged in a resiliently biased manner and have specific geometric configurations which generally allow them to ablate specific atrial tissue. The array of electrodes of each ablation catheter essentially differentiates them from one another, and provides a support structure upon which a plurality of electrodes are arranged. Further, each electrode array is selectively movable from a stored or delivery configuration for transport and delivery (such as a radially constrained configuration) to a deployed or expanded configuration for tissue ablation.

Referring to FIGS. 2 and 8-10, first ablation catheter 20 ("PVAC") is generally the first catheter to be applied in the systematic procedure in accordance with the present invention (although it may be used after a left atrial septal tissue ablation procedure). As indicated, this ablation catheter is particularly suitable to perform Pulmonary Vein PV ablation procedures on the ostial tissue of one or more pulmonary veins. This catheter is described in more detail in U.S. patent application Ser. No. 11/471,467 (hereinafter the '467 patent application), naming Kunis et al. as inventors, filed Jun. 20, 2006, and entitled ABLATION CATHETER, and is incorporated by reference herein in its entirety.

The PVAC includes a handle portion 30 and an elongated, flexible outer catheter tube 31 that defines a lumen that slideably receives a control shaft 32 therethrough. The outer catheter tube 31 is formed and dimensioned to provide sufficient column and torsional strength to support standard interventional procedures such as those which access the vasculature from a femoral vein or artery and further access the patient's heart. As shown in FIG. 2, a capture device 30a is friction fit over the distal end portion of the handle portion 30. This device 30a is configured to be detached therefrom and slide in a distal direction over the catheter tube 31 until the electrode array 24 is received therein, in the stored or confined configuration. As will be described, the capture device 30a is applied over the electrode array 24 for constraint and protection thereof during delivery through a hemostasis valve of a transseptal sheath or a vascular introducer. In this manner, the array may be introduced safely (e.g. without damage) into the patient's vasculature (e.g., a femoral vein). After introduction of electrode array 24 through the hemostasis valve, capture device 30a is moved proximally over catheter tube 31 and reattached to the distal end portion of the handle portion 30 to function as a strain relief.

At the distal region of the PVAC 20 is a carrier assembly 33 that supports the electrode array 24 thereon. The carrier assembly 33 includes a flexible carrier arm 35 having one end coupled to the end of the outer catheter tube 31 and an opposite end coupled to the central control shaft 32. By sliding and rotating the control shaft 32, such as rotating control knob 36a on the handle portion 30, the carrier assembly can be manipulated to control the geometry of the electrode array 24. For example, the control shaft 32 can be retracted to transition the carrier arm from a near linear configuration (FIG. 8) to a partial circumferential (less than 360°) loop (i.e., a partial helical or spiral shape, as shown in FIG. 9). Advancement and/or retraction of the control shaft 32 adjust the geometry of the loop, such as increasing/decreasing the diameter of the single carrier arm 35. The preferred range of usable diameters of the carrier assembly 33 is typically about 15 mm to a maximum diameter of about 35 mm, to accommodate the varied anatomical contours neighboring pulmonary vein ostia (including non-circular ostia). On the other hand, full sliding advancement of the control shaft distally causes the near-linear configuration of FIG. 8, suitable intraluminal transport therethrough. Another control knob (such as rotating knob 36b) can be provided on the handle portion 30 to allow single or bi-directional steering, as will be described.

FIGS. 8 and 10 illustrate that the flexible carrier arm 35 includes the plurality of electrodes 28 along its length. These electrodes 28 are mounted to detect electrical signals between any pair of electrodes (bi-pole) for mapping of electrical activity, and/or for performing other functions such as pacing of the heart. Moreover, these electrodes deliver ablation energy across an electrode pair or from independent electrodes when delivering uni-polar energy, using one of the Ablation Frontiers pre-programmed settings. Preferably, four (4) to sixteen (16) electrodes 28, and more preferably eight (8) to twelve (12), are positioned a long the carrier arm 35 with symmetric or asymmetric spacing. Each electrode 28 has an integral thermocouple (not shown) located on or near the tissue side of the electrode to monitor the temperature at each ablation site before and during ablation. The electrodes 28 of the PVAC 20 are preferably made of platinum, and are typically about 3 mm long and separated by about 1 mm to about 4 mm.

At the very distal end of the carrier assembly 33 is an atraumatic tip 34 that defines a through-hole 37 into a guidewire lumen extending proximally through the control shaft 32 and terminating at a guidewire exit 39 at the handle portion 30. This enables the carrier assembly 33 and flexible outer catheter tube to be percutaneously advanced over a guidewire, such as a guidewire which has had its distal end inserted into a pulmonary vein of the patient.

To facilitate single or bi-directional steering and control of the electrode array 24, a single full length pull wire 29 (or double pull wires such as in the case with bi-directional steering, neither of which is shown) is secured to the a distal portion of the end of the control shaft 32. The pull wire 29 runs proximally to the steering control knob 36b, shown in FIG. 2. Rotation of the knob pulls the wire 29 that in turn controls the plane in which the electrodes contact tissue.

Referring now to FIGS. 3 and 11-13, the second ablation catheter 21 applied in the systematic procedure is illustrated which is particularly suitable to perform an Atrial Septum ablation procedure (i.e., ablating septal tissue). Additional features of this catheter are described in copending U.S. patent applications Ser. No. 11/107,190 (hereinafter the '190 patent application), filed Apr. 15, 2005, and Ser. No. 10/997,713 (hereinafter the '713 patent application), filed Nov. 24, 2004, both to Oral et al., and both entitled ATRIAL ABLATION CATHETER ADAPTED FOR TREATMENT OF SEPTAL WALL ARRHYMOGENIC FOCI AND METHOD OF USE, and both of which are incorporated by reference herein in their entirety.

Multi-Array Septal Catheter 21 ("MASC") includes the electrode array 25 distally mounted to an elongated, flexible outer catheter tube 41 similar to that of the PVAC 20. This catheter also includes a handle portion 38, mounted to a proximal end of the outer catheter tube 41, with a deployment knob 44, an electrical connector 44a and a side-arm connector 44b (FIG. 3). A capture device 44c is friction fit over the distal end portion of the handle portion 38, and is configured for sliding axially along outer catheter tube 41 such as to capture electrode array 25 for introduction into a hemostasis valve.

Figure 13:
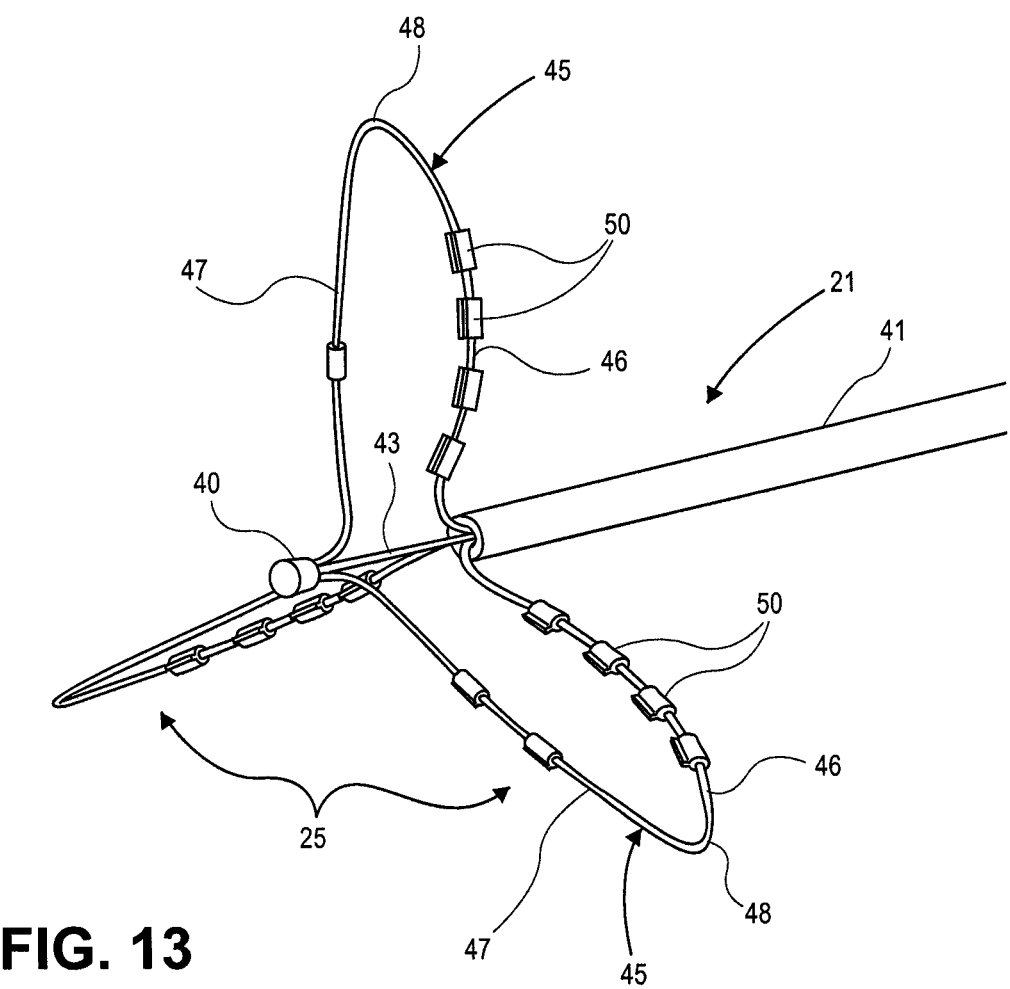
FIG. 13 is an enlarged, fragmentary, front perspective view the distal portion Septal Wall Ablation Catheter of FIG. 3, illustrating the electrode array in the deployed condition.

In one specific embodiment, as shown in FIGS. 3 and 13, the MASC 21 includes a central control shaft 43 slideably received in a lumen of the outer catheter tube 41. One end of the control shaft 43 is mounted to a central hub 40 at a distal portion of the electrode array 25, while an opposite end is operably mounted to the deployment knob 44 that controls the axial displacement of the control shaft relative to the outer catheter tube 41. Accordingly, a proximal portion of the electrode array 25 is mounted to the outer catheter tube 41 while a distal portion of the array is affixed the control shaft 43, via central hub 40.

Figure 11:
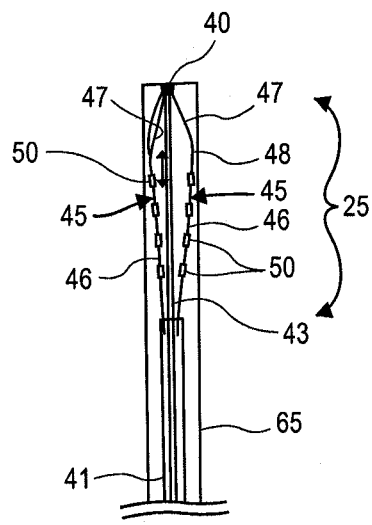
FIG. 11 is a fragmentary, side elevation view of a distal portion the Septal Wall Ablation Catheter of FIG. 3, illustrating the electrode array in a generally linear transport configuration.
Figure 12:
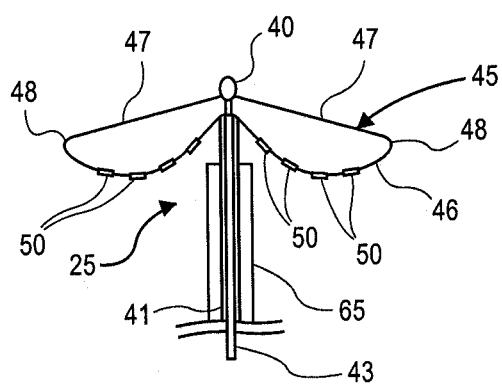
FIG. 12 is a fragmentary, side elevation view of a distal portion the Septal Wall Ablation Catheter of FIG. 3, illustrating the electrode array in a deployed configuration.

More particularly, this electrode array 25 includes at least two or more resiliently biased support arms 45 that are selectively movable from a generally linear transport configuration (e.g., internally constrained by the interior walls of a transseptal sheath 65, as shown FIG. 11 and as will be described) to a deployed configuration (FIGS. 12 and 13). More particularly, the MASC electrode array 25 includes at least three support arms 45 equally spaced apart (about 120°), relative to one another, about the substantially coaxial longitudinal axes of the distal portions of the outer catheter tube 41 and the control shaft 43. Each support arm includes a proximal arm segment 46 and a distal arm segment 47, each having opposed ends affixed together through a flexible bend section 48 thereof. The proximal end of each support arm 45 is coupled to the distal section of the outer catheter tube 41, while the opposed distal ends thereof are coupled to the central hub 40 disposed on the distal end of the control shaft 43. When deployed, as shown in one specific embodiment of FIG. 12, the deployed support arms 45 are biased to extend radially outward to form a radially asymmetric or oblique arrangement with lopsided proximal lobes.

FIG. 13 illustrates that the proximal arm segment 46 of each arm 45 supports two or more electrodes 50 spaced-apart there along. Accordingly, unlike the PVAC 20, the electrode array 25 is configured to ablate tissue in a proximally facing direction, requiring retraction of the electrode array 25 (i.e., a tensile force) to engage any atrial septal tissue. These electrodes 50 may be operated for delivery of ablation energy, mapping of electrical activity, and/or for performing other functions such as pacing of the heart. Again, each electrode 50 is preferably paired with one or more other electrodes, and includes an integral thermocouple (not shown) located on or near the tissue side of the electrode to monitor the temperature at each ablation site before and during ablation.

As indicated above, the electrode array 25 of the MASC 21 can comprise any number of resiliently biased support arms 45. The three arm array, however, is well suited for the septal wall ablation therapy. In one specific embodiment, an asymmetric arrangement of electrodes 50, is provided, wherein, each electrode is 2 mm long, and is fixed to the array arm with a 2 mm gap between adjacent electrodes, although the inner most electrode of each set is radially spaced different distances from the longitudinal axis of the outer catheter tube 41 and the control shaft 43. With the electrodes arranged in this asymmetric pattern on each of the otherwise symmetrical array arms, rotation of the array after ablation in one position will be less likely to result in seating the electrodes directly on a previously ablated section of the septal wall. In one specific embodiment, the electrodes 50 are preferably platinum, and about 1 to 2 mm wide and about 2 to 3 mm long.

During vascular transport or advancement of the MASC electrode array 25 to a target site, the resilient support arms 45 of the array, which are biased toward the deployed condition, are positioned in the generally linear transport configuration of FIG. 11. Such generally linear configuration of the support arms enables the electrode array 25 to be contained within the lumen of the sheath, an orientation necessary to be intraluminally advanced through the vasculature of the patient. Moreover, once the MASC electrode array 25 is positioned in the lumen of the transseptal sheath 65, the lumen walls themselves are relied upon to constrain the array and maintain the support arms in the generally linear transport configuration during advancement therethrough.

To initially position the array in this transport configuration, the control shaft 43 may be advanced distally from the lumen of the outer catheter tube 41 (e.g., via rotating knob 44 of handle portion 38), forcing the central hub 40 distally away from the distal end of the outer catheter tube, and collapsing the resilient support arms toward their respective generally linear configuration. More preferably, the capture device 44c is slid distally along the outer catheter tube 41 and over the electrode array 25, causing the support arms 45 to move to the generally linear transport configuration. Once the capture device 44c is inserted into the hemostasis valve of transseptal sheath 65, the electrode array can then be safely transferred (e.g. without damaging the electrode array) into the lumen of the sheath, already in the transport configuration. As will be described in greater detail below, the electrode array 25 of the MASC 21 can then be deployed by advancing the array, in the generally linear configuration, beyond and out of the distal end of the sheath. The resiliently biased arms deploy radially outward from the longitudinal axis of the electrode array 25 to the deployed configuration of FIG. 12 once the radial constraint exerted by the lumen walls of the sheath 65 is removed.

A third catheter is shown in FIGS. 4 and 14-16 which is adapted to perform an Atrial Wall ablation procedure (i.e., to ablate atrial wall tissue). Features of this catheter are described in catheter copending U.S. patent application Ser. No. 10/997,172 (hereinafter the '172 patent application), naming Kunis et al. as inventors, filed Nov. 24, 2004, and entitled ATRIAL ABLATION CATHETER AND METHOD OF USE, U.S. patent application Ser. No. 11/107,191 (hereinafter the '191 patent application), naming Kunis et al. as inventors, filed Apr. 15, 2005, and entitled ATRIAL ABLATION CATHETER AND METHOD OF USE, both of which are incorporated by reference herein in their entirety.

Similar to the first and second catheters 20 and 21, this Multi-Arm Ablation Catheter 22 ("MAAC") includes the electrode array 26 distally mounted to an elongated, flexible outer catheter tube 53. This catheter also includes a handle portion 52 with a control or steering knob 54, an electrical connector 54a and a side-arm connector 54b. Similar to both the PVAC and MASC, as shown in FIG. 4, the MAAC 22 includes a capture device 54c that is friction fit over the distal end portion of the handle portion 52, and is configured for sliding axially along the outer catheter tube 53 in order to capture electrode array 26 for introduction into a hemostasis valve. Mounted to the distal end of outer tube 53 is the electrode array 26 with forward facing electrodes 57. A steering pull wire 59 (not shown) is secured near the distal end of the outer tube 53. The pull wire runs proximally to the steering control knob 54. Rotation of the knob pulls the wire 59 to effect steering of the distal end of the catheter.

Figure 14:
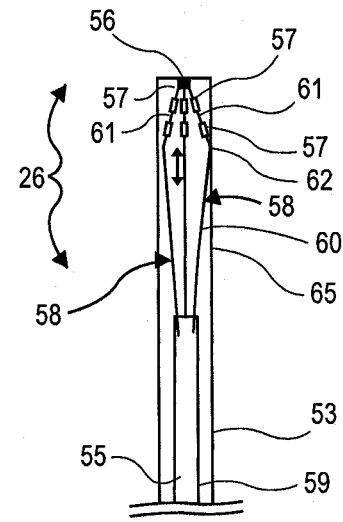
FIG. 14 is a fragmentary, side elevation view of a distal portion the Atrial Wall Ablation Catheter of FIG. 4, illustrating the electrode array in a generally linear transport configuration.
Figure 15:
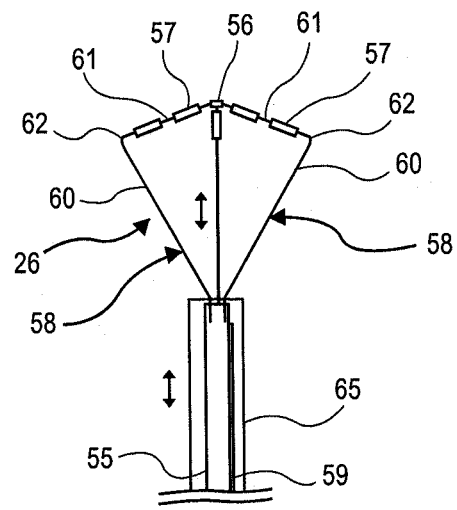
FIG. 15 is a fragmentary, side elevation view of a distal portion the Atrial Wall Ablation Catheter of FIG. 4, illustrating the electrode array in a deployed configuration.
Figure 16:
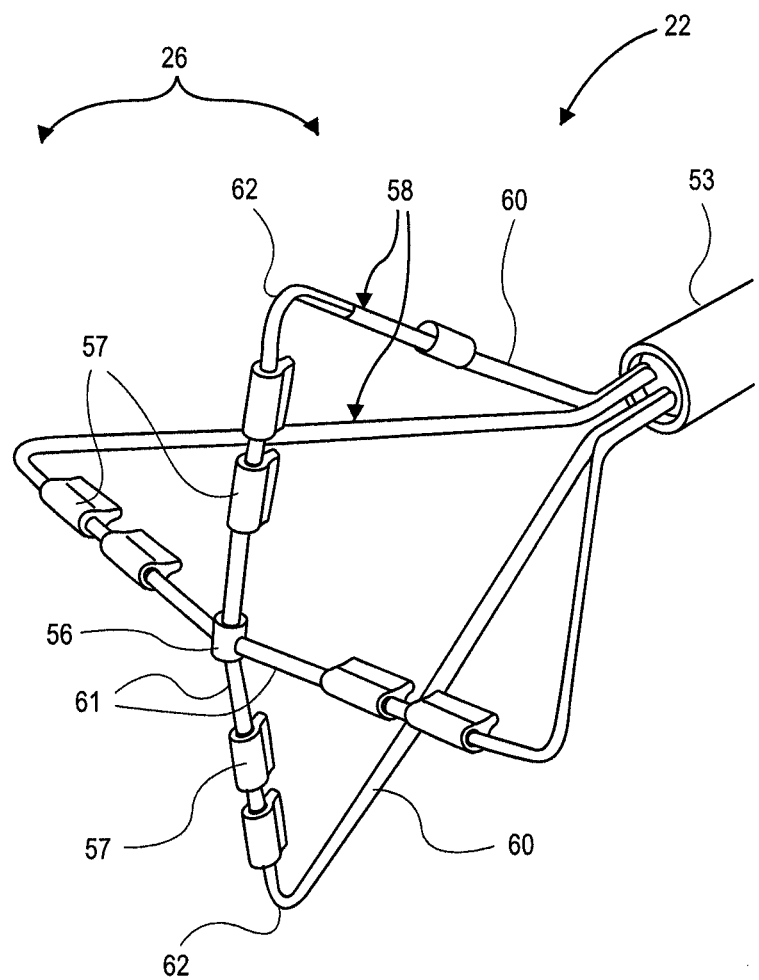
FIG. 16 is an enlarged, fragmentary, front perspective view of the distal portion Atrial Wall Ablation Catheter of FIG. 4, illustrating the electrode array in the deployed condition.

The electrode array 26 includes at least two or more resiliently biased support arms 58 that are selectively movable from a generally linear transport configuration (FIG. 14) to a deployed configuration (FIGS. 15 and 16). More preferably, the MAAC electrode array 26 includes at least four support arms 58 equally spaced apart (about 90°), relative one another, about a longitudinal axis of a distal portion of the outer tube 53. Each arm 58 includes a proximal arm segment 60 and a distal arm segment 61, each having opposed ends affixed together through a flexible bend section 62 thereof. The proximal arm segment 60 of each respective support arm 58 is coupled to the outer catheter tube 53, while the opposed distal arm segment 61 is coupled to a central hub 56. When deployed, in one specific embodiment, the respective support arms 58 are biased radially outward to form a triangular segment or arrangement where the distal arm segments 61 are oriented to extend in a direction distally from a plane intersecting the flexible bend sections 62, as shown in FIG. 15.

FIGS. 15 and 16 illustrate that the distal arm segment of each arm supports two or more electrodes 57 spaced-apart therealong. Unlike the MASC, but similar to the PVAC, the electrode array 26 is configured to be advanced distally to make contact with tissue (and ablate the tissue)

As mentioned, the electrode array 26 can comprise any number of resiliently biased support arms 58, though the four support arms array is well suited for the Atrial Wall ablation procedure. Further, each arm 58 can carry any number of electrodes 57, which may be operable to not only deliver ablation energy, by also energy for mapping of electrical activity, and/or for performing other functions such as pacing of the heart. Again, each electrode 57 is preferably paired with one or more other electrodes, and includes an integral thermocouple (not shown) located on the tissue side of the electrode to monitor the temperature at each ablation site before and during ablation. In one specific embodiment, the electrodes 57 are preferably platinum, about 1 to 2 mm wide and about 2 to 3 mm long, and can be symmetrically or asymmetrically spaced.

During transportation of the electrode array 26 through the vasculature, the multitude of support arms 58 are placed in a generally linear configuration, preferably via the capture device 54c, which is subsequently inserted into a lumen of the sheath (FIG. 14). Similar to the vascular transport of the MASC, the constraint of the lumen walls of the sheath are relied upon to maintain the support arms, and thus the array 26, in the generally linear transport configuration during advancement therethrough. As mentioned, this configuration enables intraluminal advancement through the vasculature of the patient. To deploy the electrode array 26 of the MAAC 22, the array, in the generally linear configuration, is initially advanced beyond and out of the lumen of the sheath. The resiliently biased arms deploy radially outward from the longitudinal axis of the outer tube 53 to the deployed configuration of FIG. 15. Each arm is then deployed in a generally triangular configuration with each proximal arm segment forming an acute angle with the longitudinal axis of the outer tube 53, while each distal arm segment 61 extends generally in a direction distally from a plane that contain the flexible bend sections 62 and that perpendicularly intersects the longitudinal axis the outer tube 53.

Figure 7:
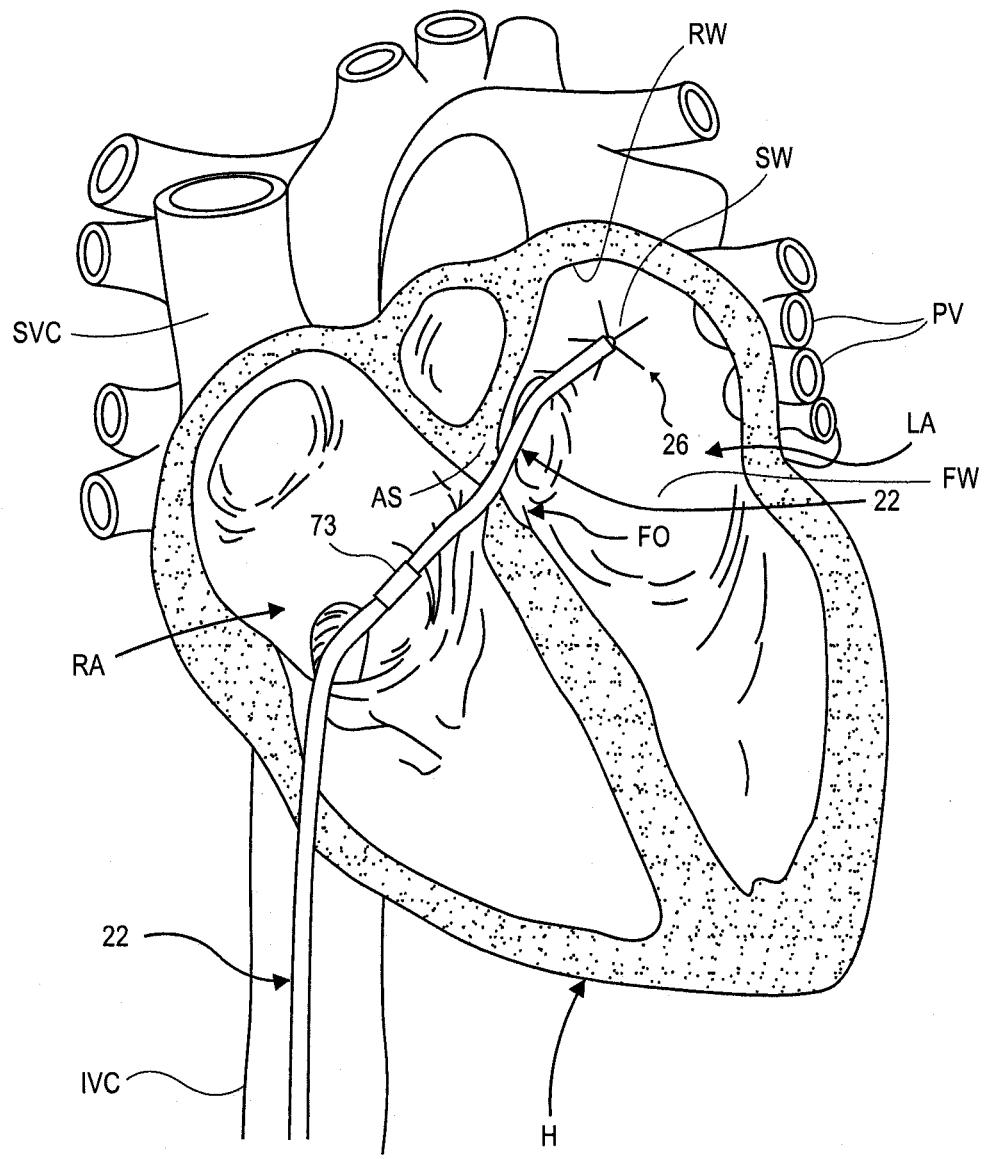
FIG. 7 is a front elevation view, in cross-section, of the patient's Heart (H) undergoing an Atrial Wall ablation procedure, in accordance with the present invention, with the Atrial Wall Ablation Catheter of FIG. 4.

Turning now to FIGS. 5-7, an exemplary method for treating continuous atrial fibrillation will be described. While in some embodiments the method includes ablating pulmonary vein and septal tissue (particularly with the PVAC and the MASC), in some methods the MAAC will also be used to treat atrial wall tissue. The T-VAC catheter (described below in reference to FIGS. 22 and 23) may also be used with any or all of the other catheters) during the procedure.

Referring to FIG. 5A, a cutaway view of a human Heart H is illustrated, showing the major structures of the heart including the Right Atrium (RA), the Left Atrium (LA), the Right Ventricle (RV), and the Left Ventricle (LV). The Atrial Septum (AS) separates the left and right atria, and includes the Fossa Ovalis (FO), a small depression in the Atrial Septum which is easily punctured (e.g. to enter the Left Atrium LA) and easily heals (e.g. after the completion of a transseptal procedure). Thus, this region is suitable for use as an access pathway from the Right Atrium (RA) to the Left Atrium (LA).

For patients suffering from continuous atrial fibrillation, aberrant electrically conductive tissue, such as arrhythmogenic foci, drivers or rotors that cause or sustain atrial fibrillation may be present in multiple locations of the Left Atrium (LA). These regions include the ostia of the Pulmonary Veins (PV), the Atrial Septum (AS) and/or Left Atrial Wall tissue. In a subset of continuous AF patients, aberrant signals are also present in the Right Atrium (RA) or Coronary Sinus (CS) and may need to be ablated as well (by the catheters of the present invention and/or additional ablation devices). It has been found that the systematic approach for the treatment of continuous atrial fibrillation, in accordance with the present invention, has been very effective, especially when employing the above mentioned assembly of ablation catheters.

Initially, using conventional transseptal access techniques, a transseptal sheath 65 is inserted through a transseptal wall puncture 27 in the Septal Wall (SW) from the Right Atrium (RA) into the Left Atrium (LA), preferably at the Fossa Ovalis (FO) (FIG. 5A). When passing into the Left Atrium (LA), the transseptal sheath 65 passes through or penetrates the fossa ovalis, such as over a guidewire 66 (see FIG. 17) which may have been placed by a transseptal puncture device (not shown). Briefly, such Right Atrium (RA) access is preferably performed through the Femoral Vein (FV) and the Inferior Vena Cava (IVC), although access may be alternatively performed through a jugular vein and the Superior Vena Cava (SVC). This access technique, and associated transseptal sheath devices are well known in the field and will not be described in detail.

It will be appreciated that while the application of a transseptal sheath is desired, this use is not necessary to successfully perform the systematic ablation procedure of the present invention. Moreover, it will be appreciated that while this systematic procedure is shown and as described specifically applying the PVAC 20, the MASC 21 and the MAAC 22 ablation instruments, other ablation catheters (e.g. tip ablation catheters) and devices may be applied that are capable of treating the same or different cardiac tissue regions to eliminate aberrant electrical pathways therethrough.

In this embodiment, the first catheter 20 is applied to address the aberrant electrical pathways around the pulmonary vein ostia. The preferred first catheter, as mentioned, is the PVAC 20, or a catheter similarly adapted to perform such a Pulmonary Vein ablation procedure.

Referring to FIG. 2, the PVAC includes a handle portion 30 with a deployment control knob 36a and a steering control knob 36b, and an electrical connector or plug 67. One or more internal push/pull wires (not shown) are provided, having one end affixed to the outer catheter tube and an opposite end coupled to the steering control knob 36b to enable steering thereof. An elongated flexible outer catheter tube 31 is mounted on the end of the handle portion 30, and houses the carrier assembly 33 on a distal end thereof. The carrier assembly, with the single carrier arm 35 that supports the plurality of electrodes 28 thereon, is adapted to be deformable such that pressing the carrier assembly into pulmonary vein ostia will cause one or more, and preferably all of electrodes 28 to make sufficient contact with tissue to be analyzed and/or ablated.

Each of the electrodes 28 is attached via connecting wires and one or more connectors, such as plug 67, to an RF Ablation Generator 16 (FIGS. 1 and 2). This RF Ablation Generator is also attached to a patch electrode, such as a conductive pad attached to the back of the patient, to enable the delivery of Monopolar ablation energy. One particular suitable RF Ablation Generator is that described in our U.S. Provisional patent Application Ser. No. 60/928,788 (hereinafter the '788 patent application), naming Sherman et al. as inventors, filed May 11, 2007, and entitled RF ENERGY DELIVERY SYSTEM AND METHOD, the entirety of which is incorporated by reference, and which is described in more detail below.

While Monopolar and Bipolar RF ablation energy are the preferred forms of energy to pass through the electrodes of the ablation catheters, it will be appreciated that other forms of ablation energy that may be additionally or alternatively emitted from the electrodes or other ablation elements include electrical energy, magnetic energy, microwave energy, thermal energy (including heat and cryogenic energy) and combinations thereof. Moreover, other forms of ablation energy that may be applied that are emitted from the array include acoustic energy, sound energy, chemical energy, photonic energy, mechanical energy, physical energy, radiation energy and a combination thereof.

During commencement of the application of the PVAC, the distal portion thereof is advanced through the patient's vasculature, via the femoral vein. The distal portion of the PVAC 20 is then advanced into the Right Atrium (RA), preferably through the Inferior Vena Cava (IVC), via a lumen of the trans-septal sheath 65. The outer catheter tube 31 of the PVAC 20 is sized for this advancement through the patient's vasculature, such as where the inserted (shaft) diameter is approximately 9 Fr, the shaft working length is approximately 115 cm and the overall length is typically 158 cm. The PVAC 20 is inserted over guidewire 66, through the lumen of the trans-septal sheath 65, and into the Left Atrium (LA).

In order to advance the carrier assembly 33 through the vasculature and into the Left Atrium (LA), the PVAC 20 is oriented in the substantially linear transport configuration (FIG. 8) by advancing control shaft 32 distally, such as by manipulating a deployment control (e.g., knob 36a) on the handle portion 30 of the PVAC 20. In turn the flexible carrier arm 35 is urged toward the linear configuration. In this linear orientation, the carrier assembly is maximally compact in a transverse dimension, and can be easily advanced through the transseptal sheath 65.

The capture device 30a may then be detached from the distal end portion of the handle portion 30, and slid in a distal direction over the catheter tube 31 all the way up to the electrode array 24. While holding the capture device against the electrode array 24, the deployment control knob 36a may be operated incrementally to advance the array distally and assure that the tip of the electrode array is distal to the capture to prevent kinking thereof. The electrode array may then be captured in, or received within the capture device 30a, in the stored or confined configuration.

The tip of the capture device 30a can then be inserted into a hemostasis valve or the like of the sheath 65 until the capture device is seated against the inner surface of a hub of the sheath, enabling the electrode array to be safely transferred into the lumen of the sheath, already in the transport configuration. The array and outer catheter tube 31 are advanced into the lumen of the transseptal sheath about five to eight inches. The capture device 30a may be detached or otherwise moved away from the hub, and reattached to the distal end of the handle portion 30, functioning as a strain relief (similar for the MASC and MAAC).

Once the distal portion of the carrier assembly 33 is advanced along the guidewire 66 and past the distal end of the transseptal sheath 65, using conventional fluoroscopy techniques, it enters the Left Atrium (LA). When it is determined that the carrier assembly is sufficiently past the sheath 65, using conventional fluoroscopy techniques, deployment of the carrier assembly may commence. In one particular embodiment, for instance, deployment of the electrode array 24 may begin when a particular electrode 28 along the single arm 35, such as the third or fourth electrode, is advanced out of and past the end of the sheath 65.

To deploy the carrier assembly 33 (i.e., in the deployed condition of FIGS. 9 and 10), as previously mentioned, the control shaft 32 is retracted relative to the distal end of the outer catheter tube 31, via manipulation of the handle control knob 36a. Thus, while the longitudinal length of the carrier assembly is decreasing, the radial dimension of the deploying electrode array is increasing. The carrier assembly 33, thus, can be further advanced into the Left Atrium (LA) while simultaneously retracting the control shaft 32 to deploy the electrode array until it is fully beyond the end of the transseptal sheath.

The resiliently biased carrier arm 35 of the carrier assembly 33 extends radially into a partial helical or spiral configuration illustrated in FIG. 9. As previously indicated, by adjusting the retraction/extension and rotation of the control shaft 32 about its longitudinal axis, the shape and diameter of the loop can be adjusted. This permits accommodation of the various anatomical contours neighboring the pulmonary vein ostia (including non-circular ostia), as well as enabling the operator to adjust the size and shape of the array to best suit the particular patient's pulmonary vein ostia. In one specific embodiment, the operational diameter of the carrier assembly 33 of the PVAC can be diametrically configured between about 15 mm to a maximum of about 35 mm, while in other embodiments; the diametric range is on the order of 10 mm to about 50 mm.

In some instances, to fully deploy and/or deflect the distal segment of the PVAC 20, the transseptal sheath 65 may be withdrawn proximally until the distal end thereof is removed from the Left Atrium (LA) of the Heart (H) (FIGS. 5B and 5D). Such removal of the sheath from the Left Atrium (LA) not only allows full deflection of the electrode array 24, but also provides the carrier assembly 33 with greater lateral agility within the Left Atrium (LA) to enable steering and repositioning therein, via the steering mechanism In one embodiment, it may only be required to retract the distal tip of the sheath 65 from the Left Atrium (LA) but not fully withdraw it from contact with the septal puncture 27 (e.g. to a location where a minimal portion of the distal end of the sheath remains in the Left Atrium), in order to provide the necessary added agility, etc. to steer and/or fully deploy the carrier assembly 33. In another configuration, as already illustrated in FIGS. 5B and 5D, the distal end of the sheath is retracted or withdrawn fully from the septal puncture 27, and into the Right Atrium (RA), although preferably not into the Inferior Vena Cava.

Once the carrier assembly 33 is oriented in the deployed condition, the guidewire 66 is retracted until the distal end thereof is positioned proximate to or flush with the distal end of the PVAC 20 (FIGS. 8 and 10). As indicated above, the distal end of control shaft 32 is covered with the atraumatic tip 34, defining the exit hole 37 in communication with the internal guidewire lumen and upon which the distal end of the guidewire 66 becomes generally flush with.

In one preferred embodiment of the present invention it has been found that systematically treating the Pulmonary Vein ostia first, followed by treating the Septal Wall (SW) has yielded the best overall results, leading to the least amount of subsequent touch-up or other ablation (such as using the MAAC catheter and/or a single point tip catheter, as will be described) thereafter.

Within the Pulmonary Vein ablation procedure, however, it has also been found that the most efficient and successful results have been found by following a preferred order of treatment of the vein tissue. Specifically, it has been found that the most successful treatments first treat the Left Superior Pulmonary Vein (LSPV) (FIG. 5A), then the Left Inferior Pulmonary Vein (LIPV) (FIG. 5C), then the Right Superior Pulmonary Vein (RSPV) (FIG. 5B), and finally the Right Inferior Pulmonary Vein (RIPV) (FIG. 5D), if accessible. To treat the Left and/or Right Superior Pulmonary Veins, the catheter electrode array is in the top portion of the Left Atrium, so navigation between Right and Left Pulmonary Veins is more efficient. Likewise, when treating the Left and/or Right Inferior Pulmonary Veins, the catheter electrode array is in the bottom portion of the Left Atrium, so navigation between Right and Left Pulmonary Veins is also more efficient. In an alternative embodiment, the Left Superior and Left Inferior Pulmonary Veins are treated sequentially, and subsequently the Right Superior and Right Inferior are treated sequentially.

Figure 17:
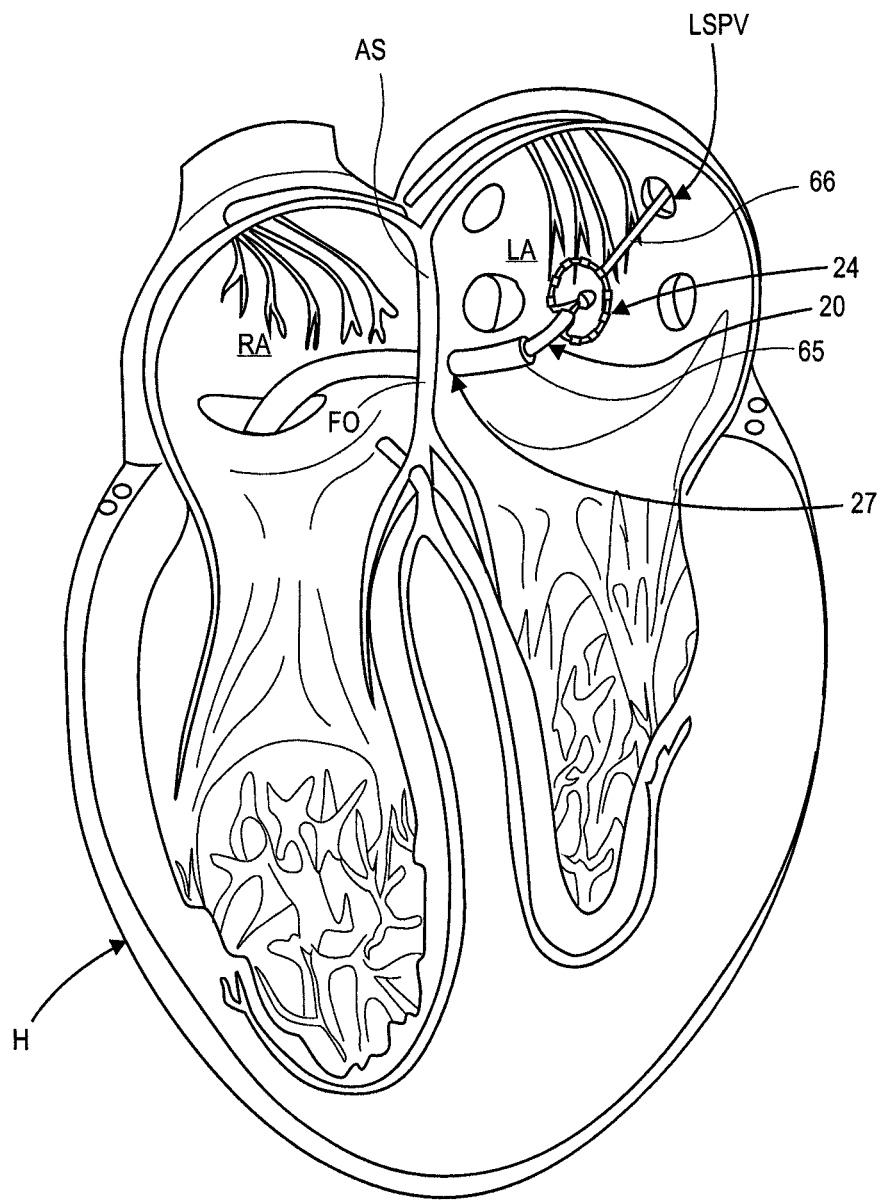
FIG. 17 is a front elevation view, in cross-section, of the patient's Heart (H) illustrating the deployed electrode array of the PVAC prior to ablative contact with the Left Superior Pulmonary Vein ostial tissue.

Accordingly, using the steering mechanism of the PVAC 20 (e.g., the steering control knob 36b and the internal pull wire or wires 29), the atraumatic tip 34 is deflected and directed toward the Left Superior Pulmonary Vein (LSPV), where the guidewire 66 is then advanced into the lumen thereof (FIG. 17). For example, the one or two internal pull wires may be pulled proximally to deflect the distal end of the carrier assembly in one or more directions. Using the pull wires, the operator can steer the array as needed to contact the ostial tissue of different Pulmonary Veins (PV) via the operation of the steering control knob 36b on the handle portion of the PVAC. Referring back to FIGS. 9 and 10, once the electrode array has been deployed or nearly deployed, the carrier assembly 33 of the PVAC 20 is advanced along the guidewire 66 to the antrum of the LSPV. At this juncture, the plane or shape of the electrode array 24 (i.e., carrier assembly 33) can be adjusted to achieve optimal contact with the surrounding targeted tissue. By way of example, adjusting the deployment control knob 36a in the counterclockwise direction increases the electrode array 24 diameter, while adjusting the control knob 36a in the clockwise direction decreases the electrode array 24 diameter.

After proper deployment of the substantially helical or spiral carrier assembly, and after proper orientation and location of the electrodes relative to the targeted Pulmonary Vein (PV) tissue, the carrier assembly 33 is advanced distally, as a unit, along the guidewire 66 until sufficient contact with the ostial tissue surrounding the Left Superior Pulmonary Vein (LSPV) is determined. The carrier assembly 33, as mentioned, is adapted to be deformable such that pressing carrier assembly into Pulmonary Vein ostium will cause one or more, and preferably a majority of electrodes 28 to make sufficient contact with tissue to be analyzed and/or ablated. In one specific embodiment, as best shown in FIG. 5A, the transseptal sheath 65 may be advanced forwardly, positioning the distal end thereof closer to the Left Superior Pulmonary Vein (LSPV). In this manner, the transseptal sheath may provide additional lateral support to the carrier assembly 33 during compressive engagement against the ostial tissue of the Left Superior Pulmonary Vein (LSPV). For example, by advancing the distal end of the sheath 65 along the guidewire 66, and to a position about 5-10 mm from the antrum of the Left Superior Pulmonary Vein (LSPV), a greater amount of compressive force can be exerted against the ostial tissue by the deployed electrode array 24, via the PVAC outer catheter tube 31, with less concern for bowing the outer tube. In addition, the distal end of sheath 65 may also be deflectable and used in combination with the deflection of the PVAC 20.

Conventional marking elements (e.g. radiopaque markers) may be included in the carrier assemblies or other components of the ablation catheters, such as to determine the relative location of the carrier assembly and/or the deployment condition of the carrier assembly, as well as confirm contact with tissue. For instance, using fluoroscopy, sufficient contact with tissue may be determined when the carrier assembly transitions to a convex shape. Applying another technique, the location and tissue contact can be confirmed using the electrodes 28 of the PVAC 20, which are coupled to the ECG unit 23, in addition to the RF Ablation Generator 16, via ECG interface 17. For example, an electrophysiologist can map about the Left Superior Pulmonary Vein (LSPV) ostium to not only determine whether or not to ablate any tissue, but to also confirm tissue contact which is identified in the mapping procedure. If conditions are determined to be inadequate, an operator may adjust the shape of carrier assembly 33 (e.g. through advancement or retraction of control shaft 32) and/or the operator may reposition carrier assembly 33 against tissue through various manipulations performed at the proximal end of PVAC 20. Moreover, it will be appreciated that other conventional mapping catheters can be applied to map signals, such as a standard electrophysiology lasso catheter.

Once sufficient tissue contact has been established, and the mapping procedure has confirmed the presence of aberrant conductive pathways, ablation energy may be passed through the relatively low power (high efficiency) output electrodes 28 (i.e., 5-10 Watts) of the electrode array 24. In a preferred embodiment, the electrode array 24 of the PVAC 20 and the RF Ablation Generator 16 cooperate to deliver RF energy in Monopolar, Bipolar or combination Monopolar-Bipolar energy delivery modes, simultaneously or sequentially, with or without "off," or no energy delivered time durations.

Accordingly, depending upon a number of primary factors, such as the geometry and location of targeted region of the Heart (H), the quality of the electrode/tissue contact, the selected magnitude of the RF energy delivered to the electrodes, the type of RF energy applied (i.e., Monopolar, Bipolar or combination Monopolar-Bipolar energy), as well as the duration of the ablation, lesion formation can be estimated that is sufficient to eliminate aberrant conductive pathways therethrough. In accordance with the present invention, given the above factors, a target temperature of the ablated tissue is about 60° C. is desired, with a lower limit of about 55° C. and an upper limit of about 65° C. In general, an electrode temperature measurement in the range of at least 55° C. is necessary to ensure the tissue is at a sufficient ablation temperature.

Figure 22:
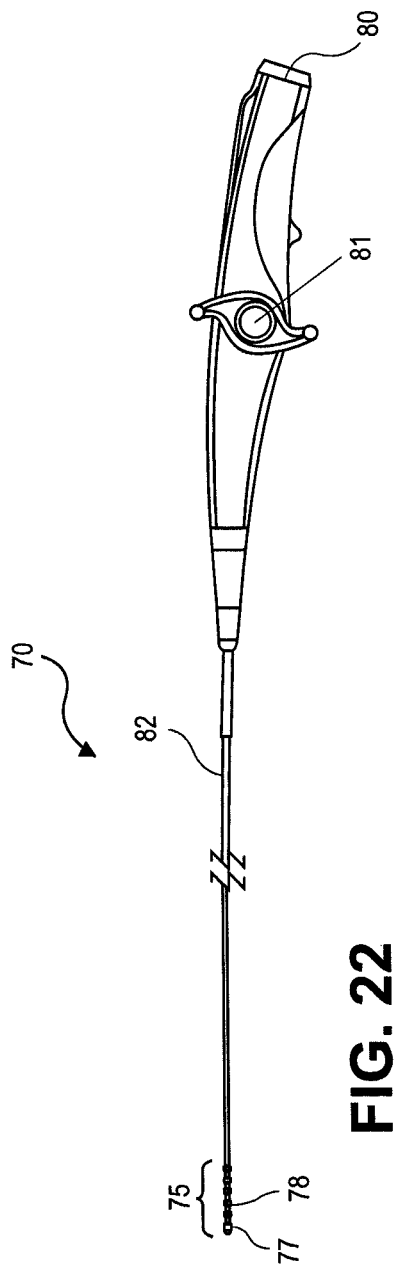
FIG. 22 is a side elevation view of a Tip-Versatile Ablation Catheter with a single tip ablation element.

In another preferred embodiment, the RF Ablation Generator 16 is configured to accept a signal from one or more sensors integral to PVAC 20, not shown, such that the energy delivered can be modified via an algorithm which processes the information received from the one or more sensors. This will be described in greater detail below with reference to the RF Generator settings, and also applies in general to the MASC 21, the MAAC 22 and the Tip-Versatile Ablation Catheter 70 (TVAC), to be described below, and as shown in FIG. 22. In a preferred embodiment, temperature sensors such as thermocouples are included with each electrode.

As mentioned, the combination of our PVAC 20, as set forth in '467 patent application, and our RF Generator, as set forth in '788 patent application, enables both Monopolar and Bipolar ablation applications, and any combination thereof. Depending upon the application and situation, these power schemes can be combined for optimal performance, as detailed in TABLE I below.

Applying the PVAC 20 for this procedure, by way of example, an optimal power ratio has been found to be 4:1 (80% Bipolar: 20% Monopolar, having a max power of about 8 W) to about 2:1 (66% Bipolar: 33% Monopolar, having a max power of about 10 W). The lowest power setting, using the PVAC 20, would involve a pure Bipolar application with each electrode outputting about 6 W, while the highest power setting would involve a pure Monopolar application with each electrode outputting about 10 W. For most applications, however, the upper limit would involve an optimal power ratio of 1:1 (50% Bipolar: 50% Monopolar, having a max power of about 10 W).

TABLE I

| PVAC | Target/Preferred | Applicable Lower Limit | Applicable Upper Limit |
|---|---|---|---|
| Optimal Power Ratio | 4:1 (80% Bipolar:20% Monopolar) 2:1 for "stubborn" fascicles | 4:1 | 1:1 |
| Max Power | 10 Watts (Mono, 1:1 & 2:1) 8 Watts (4:1) 6 Watts (Bipolar) | | |
| Optimal Power Range | 5 Watts-10 Watts | | |
| Target Temp | 60° C. | 55° C. | 65° C. |
| Target Time | 60 seconds | 45 seconds | 90 seconds |
| Target Placement Location | Antrum/Ostium of each Pulmonary Vein | Ostium | Antrum |
| Secondary Power Ratio | 2:1 | | |

Applying the above-mentioned range of parameters, it has been determined that a targeted time for continuous ablative contact with the array of electrodes for the PVAC is in the range of at least about 45 seconds to no more than about 90 seconds. Optimally, in most instances, about 60 seconds of ablative contact is required to achieve adequate energy penetration into the tissue to ensure the necessary tissue ablation. Lower power settings may require ablation durations that are greater than 60 seconds, while higher power settings may result in sufficient ablation durations that are less than 60 seconds. Moreover, other prominent factors that may affect the quality and penetration of the ablations include the geometry of the targeted tissue, its type, thickness and/or density, as well as the targeted tissue's proximity to other organs or sensitive areas (i.e. locations where deep penetration of heat would cause an undesired risk).

As an example, the initial power ratio setting may be selected at a 4:1 setting at about 8 Watts, and applied to a targeted duration of about 60 seconds. In the event that any aberrant conductive pathways are still detected, the ablation may be reapplied for 15-30 seconds, for instance. Should any aberrant conductive pathways still be detected in the Left Superior Pulmonary Vein (LSPV) ostial tissue, and for particularly "stubborn" fascicles, the power ratio may be adjusted to a 2:1 setting, at about 8 Watts-10 Watts, and applied for a targeted duration of about 60 seconds. In another example, for tissue close to a sensitive area such as the esophagus, the amount of Monopolar energy delivered may be limited (e.g. Bipolar only or higher ratios such as 4:1 or higher), such as to limit the depth of energy penetration delivered by the catheters of the present invention. In order to determine the relative location of the esophagus, the patient may be given barium paste to swallow and a venogram may be performed.

In some embodiments the generator comprises a user interface, such as the remote control shown in FIG. 1. The user interface allows a user to select parameters for the ablation treatment. The user interface preferably will allow the user to select an energy delivery mode for the treatment. For example, the user interface can allow the user to select that the generator deliver only monopolar energy, only bipolar energy, or a combination of the two. The user interface will also preferably allow the user to select a power ratio, such as 1:1, 2:1, or 4:1, when in combination mode. The generator can be manufactured to include specific alternative power ratios (e.g., 1:1, 2:1, 4:1), such that the user can select one of the established ratios, and/or the user interface can allow the user to enter a different power ratio. The user interface preferably also allows the user to change the energy mode when the catheter is changed, or when the same catheter is moved to a different location in order to ablate different tissue. For example, after pulmonary tissue is ablated, a second catheter may be used with the RF generator to ablate septal tissue. The user can select a different (or the same) energy mode for the septal ablation procedure.

The user interface can also include an input which allows the user to select the time for RF delivery (e.g., about 45 seconds to about 90 seconds).

It will be appreciated that the small electrodes provided are particularly suitable for the purpose of determining whether or not sufficient contact with the targeted tissue has been established by measuring the power setting in combination with the measured electrode temperature. If an electrode does not have sufficient tissue contact, these small electrodes quickly dissipate heat and return to their equilibrium temperature when the ablative power is removed. An inadequate tissue contact condition can be identified when an electrode fails to reach a target temperature (e.g. a temperature measured by a thermocouple integral to or otherwise in contact with the electrode), such as a temperature set by an operator or a temperature based on the amount of power delivered. In other words, a large proportion of the ablation energy is dissipated through conduction by increased contact with the blood flow, as opposed to a greater proportion of insulative contact with the targeted tissue. The position of the electrode can be adjusted, and the ablation procedure and electrode temperature measurement repeated. In a preferred embodiment, the position of the electrode is adjusted by incrementally moving the carrier assembly further into the tissue (forwardly or distally for the PVAC and the MAAC, or rearwardly or proximally for the MASC).

On the other hand, when a relatively higher than expected electrode temperature (e.g., greater than about 65° C. with a relatively low power setting of 3-5 W and a 4:1 power ratio) is measured, this is generally a good indication that the electrodes may be embedded too deep within the cardiac tissue. Consequently, the temperature is higher due to the greater insulative nature of the surrounding tissue as compared to that of blood. In this situation, the carrier assembly should be repositioned. In a preferred embodiment, the carrier assembly is incrementally moved away from the tissue (retracted proximally for the PVAC and the MAAC, or distally for the MASC), reducing contact with the atrial tissue, after which the procedure is repeated to determine whether the electrode temperature is within satisfactory tolerances.

Due to the geometry of the array of electrodes for the PVAC 20, a non-linear (e.g., spiral, helical, etc.) lesion is formed which is particularly suitable for a Pulmonary Vein-type ablation procedures. It will be appreciated that these non-linear lesions include generally circular, helical or spiral-shaped lesion formation, as well, depending upon the 3-Dimensional anatomy of the Pulmonary Vein ostium targeted. Generally, the electrode array 24 may be capable of forming continuous circular lesions (at least about 2-3 mm wide), having an angular degree, in the range of about 20° to about 320°, depending upon the topography of the targeted ostial tissue and the quality of the contact. Moreover, any combination of electrodes 28 and/or electrode pairs (channels) can be powered, maximizing or minimizing the arc length and/or depth of the non-linear lesions. To ensure isolation of the aberrant signals of the Pulmonary Veins (PV) from the atrium, however, all channel pairs of electrodes 28 are typically energized to maximize the length and area of lesion formation, while avoiding the lumen of the Pulmonary Vein such as to prevent Pulmonary Vein stenosis. Moreover, multiple lesions are created about each Pulmonary Vein (PV) ostium in more or less a clover leaf (e.g. Olympic ring) type pattern.

After formation of the initial non-linear lesion about the Left Superior Pulmonary Vein (LSPV), the PVAC 20 is repositioned, with or without changing the geometry of carrier assembly 33. Subsequently, a similar mapping and ablation step is performed to form another overlapping generally circular, helical or spiral-shaped lesion. Briefly, the steerability of the distal portion of device or the carrier assembly 33 is operated, via a control on handle portion 30, and is an important function in this repositioning process. For each pulmonary vein ostium, this repositioning will typically occur three to four times creating generally circular, helical or spiral-shaped lesions that preferably overlap. By way of example, the carrier assembly 33 may be repositioned about 90° in either direction, and the steps to perform the ablation procedure, as mentioned above, are repeated. This sequence may be performed one or two more times to ensure encircling of the LSPV ostium with four overlapping circular, helical or spiral-shaped ablation lesions.

Once a circumferential lesion set has been formed, individual fascicles can be targeted. Applying conventional mapping techniques, using the array of electrodes, the electrophysiologist can further map about the LSPV ostium, and apply energy through the catheter to ablate any aberrant electrical signals which are identified in the mapping procedure. This procedure may be repeated as necessary until there are no more aberrant traces detected.

In one specific embodiment of the present invention, mapping may be performed within the Left Superior Pulmonary Vein (LSPV) in a manner to detect any aberrant conductive pathways therethrough, and/or determine the quality of the Left Superior Pulmonary Vein (LSPV) isolation from the Left Atrium (LA). To map within the veins, the carrier assembly 33 of the PVAC 20 is first retracted from the antrum of the LSPV, and the control knob 36 on the handle portion 30 of the catheter is adjusted to elongate the deployed spiral into a helical shape, while simultaneously reducing the diameter of the deployed electrode array 24, in order to be passed into the PV lumen (e.g. while simultaneously rotating the catheter during advancement into the lumen of the PV). The carrier assembly 33 of the PVAC 20 is then advanced into the Left Superior Pulmonary Vein (LSPV), engaging the electrodes 28 of the electrode array against the inner walls of the LSPV. The control knob can be retracted slightly to obtain optimal apposition against the inside of the vein for mapping purposes. This will enable safe delivery of the electrodes to the inside of the PV. The Physician then can determine whether there are any signals that need to be verified, but are being blocked (isolated) from the atrium when mapping on the outside of the PV's.

After ablation therapy has been satisfactorily performed on the Left Superior Pulmonary Vein (LSPV), the clinician may typically perform ablations in the remaining Pulmonary Veins (PV), preferably in the remaining sequential order of the Left Inferior Pulmonary Vein (LIPV) (FIG. 5C), the Right Superior Pulmonary Vein (RSPV) (FIG. 5B) and then the Right Inferior Pulmonary Vein (RIPV) (FIG. 5D). Accordingly, the carrier assembly 33 is retracted proximally, repositioning the electrodes out of contact with the LSPV cardiac tissue and orienting the electrode array 24 generally centrally within the Left Atrium (LA). Subsequently, the distal tip of the guidewire 66 is also retracted from the LSPV, and into and generally flush with the distal tip of the PVAC's guidewire lumen. Once flush, the carrier assembly 33 is fully deployed, positioning the electrode array within a relatively single plane. As mentioned, this may be performed by the operator, via controls on the PVAC handle.

As above-mentioned, the transseptal sheath 65 may be utilized in some applications to provide additional lateral support to the carrier assembly 33 of the PVAC 20 during ablation of the LSPV. In these applications, the transseptal sheath 65 should be retracted proximally, slightly withdrawing the distal tip of the sheath 65 from the Left Atrium (LA) by a length sufficient to ensure exposure of the steering section outside of the sheath (e.g. when a non-steering sheath is used). This enables proper operation of the steering section to steer the PVAC straight toward the Right Superior Pulmonary Vein (RSPV), the next such Pulmonary Vein (PV) in the preferred ablation order above-indicated.

Once the distal tip of the catheter is properly aligned with the Right Superior Pulmonary Vein (RSPV), the tip of the guidewire 66 is advanced within the respective antrum thereof. The above-mentioned ablation, mapping and steering procedures are then repeated for each remaining PV.

In other applications, as mentioned when describing deployment of the carrier assembly 33, the transseptal sheath 65 may be withdrawn proximally until the distal end thereof is removed from the Left Atrium (LA) of the Heart (H). Such removal of the sheath from the Left Atrium (LA) provides the physician additional maneuverability of the steering mechanism to guide the tip of the PVAC 20 toward the targeted Pulmonary Vein, such as the Right Inferior PV. In one embodiment, it may only be required to remove the distal tip of the sheath 65 from the Left Atrium (LA) and not fully withdraw it from contact with the septal puncture 27, in order to provide the necessary added agility, etc. to steer and/or fully deploy the carrier assembly 33. In another configuration, the distal end of the sheath is retracted or withdrawn fully from the septal puncture 27, and into the Right Atrium (RA), although not into the Inferior Vena Cava.

When accessing a patient's Heart (H) with a Left Atrium (LA) that is smaller than average, it may be necessary to navigate the tip of the PVAC 20 back up to 180° in order to access the lumen of the Right Inferior Pulmonary Vein (RIPV). Due to space limitations within the Left Atrium (LA), the proper ablation of the ostial tissue surrounding the RIPV may be unachievable using the PVAC 20 that is currently deployed. In these instances, a PVAC catheter that can be deployed in a smaller diameter may be utilized.

In a preferred embodiment, first catheter 20 is advanced over a guidewire while electrode array 24 is advanced distally toward and into contact with pulmonary vein ostial tissue. About 30% of patients undergoing atrial fibrillation treatment have a large diameter and/or common pulmonary vein ostia (as used herein "large diameter ostium" can refer to either a large diameter ostium or common pulmonary vein ostia. The advancement of first catheter 20 over a guidewire stabilizes the rotational axis around which the spiral array 24 of electrodes is rotated. In a preferred embodiment, the center axis of array 24, which includes a guidewire thru-lumen at its distal end, is offset from the center axis of the catheter shaft. The offset design enables off-center positioning of array 24 relative to the ostium of a pulmonary vein. In patients with large or common PV ostia, the guidewire is first placed into a superior branch of a large common vein (such as via deflection of the distal end of the catheter toward the superior branch). The guidewire is sufficiently inserted into this superior branch to achieve significant stabilization of the guidewire. Array 24 of first catheter 20 is then pivoted around the guidewire seated in the superior branch to perform multiple, sequential ablations of the superior portion of the large or common PV ostia. The guidewire is then retracted from the superior branch, the distal end of the guidewire positioned proximate the tip of the catheter. The catheter tip is directed (e.g. with single or bi-directional steering control) toward an inferior branch. The guidewire is then sufficiently inserted into the inferior branch to achieve significant stabilization of the guidewire. Array 24 is then pivoted around the guidewire seated in the inferior branch to perform multiple sequential ablations to treat the inferior portion of the large or common PV ostia. First catheter 20 preferably includes bi-directional steering of its distal portion. This steering eases proper orientation of array 24 to achieve sufficient contact of array 24 electrodes with the superior and inferior tissue portions of the PV ostia. In addition to the ablation steps, the above use of the guidewire also provides a stabilization for mapping procedures also requiring ability to achieve good electrode contact while mapping both the superior and inferior tissue portions of large and common PV ostia.

In this embodiment, once the Pulmonary Veins have been treated, ablation therapy is applied to the left atrial Septal Wall (SW). In one specific embodiment, before the carrier assembly 33 of the PVAC 20 is retracted and withdrawn from the Left Atrium (LA) and transseptal sheath 65, the electrode array 24 thereof may be applied to perform an initial mapping procedure of the Septal Wall (SW). In this manner, the carrier assembly 33 of the PVAC is already deployed within the Left Atrium (LA), and incorporates an electrode array 24 suitable to perform an initial map of the Septal Wall (SW) in order to sense any aberrant conductive pathways therethrough. Accordingly, should no aberrant conductive pathways be sensed while mapping the Septal Wall (SW), it is possible that ablation therapy of the Atrial Septum (AS) may then be avoided.

Figure 18:
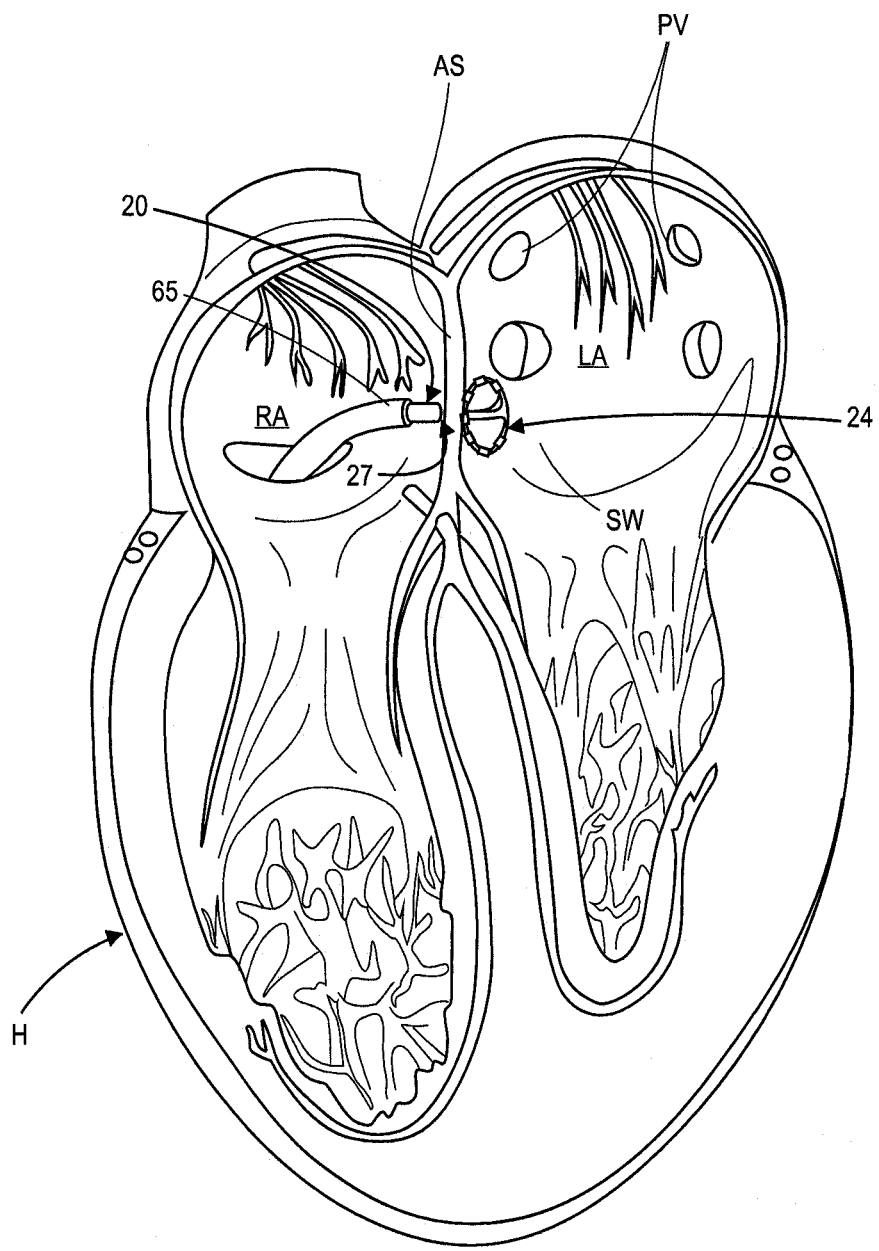
FIG. 18 is a front elevation view, in cross-section, of the patient's Heart (H) illustrating the application of the PVAC to map signals on the Septal Wall.

To perform a mapping procedure of the Septal Wall (SW), using the deployed electrode array of the PVAC 20, the distal tip of the transseptal sheath 65 is withdrawn from the Left Atrium (LA), albeit not necessarily from the septal puncture 27, if this withdrawal has not already been performed. Preferably, the carrier assembly 33 is initially oriented in fully deployed condition, where the electrode array 24 substantially contained in a plane, and is maximized in diameter. Subsequently, the outer catheter tube 31 of the PVAC 20 is retracted or pulled back proximally, tensioning the deployed electrode array 24 against the atrial Septal Wall (SW) and to initiate contact the electrodes against the tissue thereof (FIG. 18).

A conventional mapping procedure is then performed on the atrial Septal Wall (SW) using the electrodes of the PVAC to detect fractionation or other aberrant conductive pathways. The electrode array 24 can further be rotated about its longitudinal axis numerous times for repositioning and additional mapping of the Atrial Septum (AS).

Once this mapping procedure is completed, the transseptal sheath 65 may then be reinserted through the septal puncture 27 using the guidewire 66 and/or the PVAC outer catheter tube 31 as a guide. After reinsertion of the transseptal sheath 65, the control knobs on the handle portion 30 of the PVAC are operated, moving the carrier assembly 33 and electrode array 24 from the deployed configuration to the generally linear transport configuration (FIG. 8). In this linear configuration, the carrier assembly 33 of the PVAC can be withdrawn through the lumen of the transseptal sheath, and out of the Left Atrium (LA) of the Heart (H).

In another specific application, the PVAC 20 may also be employed in the Right Atrium (RA) to map and ablate the ostial tissue surrounding the Superior Vena Cava (SVC) or Inferior Vena Cava (IVC). Similar to the treatment of the Pulmonary Vein Ostia, with tip of the guidewire 66 generally flush with that of the distal end of the carrier assembly 33, the steering device can be operated to point the nested distal ends toward the lumen of the Superior Vena Cava (SVC). The tip of the guidewire 66 is advanced into the Superior Vena Cava (SVC). Once the carrier assembly 33 of the PVAC is deployed in the Right Atrium (RA) using the technique above-discussed, the deployed electrode array may be advanced into contact with the ostial tissue surrounding the Superior Vena Cava (SVC). Using a repositioning and ablation procedure similar to the ablation of one Pulmonary Vein, as noted above, the Superior Vena Cava (SVC) can be isolated. A similar procedure can be performed for isolating the Inferior Vena Cava (IVC).

In this embodiment, a second ablation catheter (e.g., the MASC 21), suitable for ablating the atrial Septal Wall (SW), is advanced through the lumen of the transseptal sheath 65. While other transluminal ablation catheters can be employed that are suitable to perform transluminal atrial septal wall ablation therapy, the Multi-Array Septal Catheter 21 (MASC) is one preferred example of a catheter adapted to perform this procedure.

Similar to the PVAC 20, to facilitate such passage through the vasculature and into the Left Atrium (LA), as mentioned above, the array is initially oriented in the substantially linear transport configuration (FIG. 11). Once the MASC electrode array 25 is received in the capture device 44c using the technique already described for the PVAC, the tip thereof can then be inserted into a hemostasis valve or the like. Again, using a similar technique, the electrode array can be safely transferred into the lumen of the sheath 65, already in the transport configuration (e.g., FIG. 11).

As the electrode array emerges from the constraining walls of the sheath lumen at the distal end of the transseptal sheath 65 and passes into the Left Atrium (LA) (FIG. 21), the resiliently biased support arms 45 are urged radially outward toward the deployed condition of FIG. 12. The control shaft 43 is, or can be, retracted proximally, via deployment know 44, into the lumen of the outer catheter tube 41. Once the distal end of the outer catheter tube 41 passes beyond the transseptal sheath 65, the complete exposure of the support arms 45 permits them to resiliently expand in the Left Atrium (LA) to the configuration in which the proximal arm segments 46 are generally perpendicular or slightly reflexed relative to the longitudinal axis of the control shaft 43 (i.e., generally deploying from the generally linear transport configuration to the deployed configuration).

To fully deploy the electrode array 25 of the MASC 21 and enable the electrodes 50 of the resilient arms 45 to obtain apposition along the Septal Wall (SW) of the Left Atrium (LA), the distal tip of the transseptal sheath 65 is again retracted or removed from the Left Atrium (LA).

As best illustrated in FIG. 6, the electrode array 25 is retracted proximally into contact with the atrial Septal Wall (SW), by pulling proximally on the outer catheter tube 40. This movement forces the distal arm segments 47 to splay distally, while at the same time resiliently biasing the proximal arm segments 46 and the electrodes 50 against and in contact with the atrial tissue of the Septal Wall (SW) of the Left Atrium (LA). The electrode array can also be manipulated by advancing/retracting control shaft 43, via deployment control knob 44.

In the event that sufficient tissue contact has not been achieved or established for the radially outermost pair of electrodes 50 on each resilient arm 45, the control shaft 43 may be incrementally advanced and/or retracted, such as via control knob 44 on the handle portion 38. In effect, the desired result is to lower the tip or bend section 48 of each resilient arm 45 toward the septal tissue in order to increase the probability of engagement of these outer most electrodes 50 with septal tissue. Subsequently, the mapping procedure may be performed to assess the quality of the contact.

Once contact has been established between the Septal Wall (SW) and the electrode array 25, the operator will perform a mapping procedure. The detected electrical signals by the electrodes can be analyzed to determine if the electrode array has been placed over an aberrant signal such as an arrhythmogenic focus.

Similar to the ablation therapy applied to the Pulmonary Vein ostia, a number of primary factors may be considered when determining the necessary power settings and duration of the ablative contact between the electrodes 50 and the targeted septal tissue. Such factors include the geometry and location of targeted region of the Heart (H) (including proximity to sensitive areas such as the esophagus), the quality of the electrode/tissue contact, the type, thickness and/or density of the targeted tissue, the selected magnitude of the RF energy delivered to the electrodes, the type of RF energy applied (i.e., Monopolar, Bipolar or combination Monopolar-Bipolar energy), as well as the duration of the ablation.

In general, the same RF Ablation Generator 16 is configured to deliver RF energy in Monopolar, Bipolar or combination Monopolar-Bipolar energy delivery modes, simultaneously or sequentially, with or without "off" or no energy delivered time durations. Any of the electrodes may be energized, as appropriate, to ablate tissue with aberrant signals, such as an arrhythmogenic focus. Bipolar RF energy may be applied between pairs of the electrodes, or Monopolar energy may be applied to any of the electrodes (grounded to the surface electrode or a return electrode located proximally on the catheter body). Again, the electrode temperature should be in the range of about 55° C., at the lower limit to about 65° C., at the upper limit thereof, with a target electrode temperature of at least 60° C. to assure a sufficient ablation.

The combination of the MASC 21 and our RF Generator, as set forth in '788 patent application, enables either Monopolar and Bipolar ablation applications, or any combination thereof. Depending upon the application and situation, these power schemes can be combined for optimal performance, again similar to the power and ratio settings set forth in TABLE I above. Preferably, it has been found that a power ratio of 1:1 (50% Bipolar: 50% Monopolar, having a max power of about 10 W) is most beneficial when initially performing septal ablation therapy with the MASC 21. In this manner, the tissue of the fossa ovalis and surrounding areas are not close to more temperature sensitive areas, allowing the application of a greater percentage of Monopolar energy.

Applying the above-mentioned range of parameters, it has been determined that a targeted time for ablative contact with the array of electrodes for the MASC, applying a 1:1 power ratio to the tissue of the Atrial Septum (AS), is in the range of at least about 45 seconds to no more than about 90 seconds. Optimally, in this instance, about 60 seconds of ablative contact is required to achieve adequate energy penetration into the tissue to ensure the necessary tissue ablation. Again, lower power settings may require ablation durations that are greater than 60 seconds, while higher power settings may result in ablation durations that are less than 60 seconds.

Similar to the PVAC 20, when a relatively lower than expected electrode temperature is measured at the electrodes (e.g. when a relatively higher power setting is applied), this is generally a good indication that the electrodes are not in good contact with the targeted tissue. In this situation, the electrode array should be repositioned, preferably incrementally retracted proximally in order to increase contact with the Atrial Septum tissue. On the other hand, when a relatively higher than expected electrode temperature is measured at the electrodes (e.g. when a lower power setting is applied), this is generally a good indication that the electrodes may be embedded too deep within the septal tissue. Consequently, the electrode array 25 should be repositioned, preferably incrementally advanced distally, reducing contact with this septal tissue. The procedure may then be repeated to determine whether the achieved electrode temperature is within satisfactory tolerances.

Generally, each single proximal arm segment 46 will form a generally linear lesion (e.g., about 3 mm×20 mm), applying the electrode pairs operating in Bipolar mode and/or a combination of Bipolar and Monopolar modes. Other therapeutic lesion shapes, however, may be created using electrodes pairs established between the electrodes of one arm and the electrodes of another arm, operating such pairs in Bipolar mode, and/or operating electrodes in conjunction with return electrodes in a Monopolar mode. Due to the preferred geometry of the array of electrodes 50 for MASC 21, as shown in FIG. 13, three substantially linear lesions are formed, each lesion extending radially outward from a center thereof corresponding to the septal puncture 27, and each equally spaced apart from an adjacent lesion by about 120°.

To fully circumferentially treat the septum using the array of electrodes 50 of the MASC 21, it will be necessary to advance the electrode array 25 distally, moving the array out of contact with the septal tissue, incrementally rotate the array about the longitudinal axis of the array, and then reseat the array against the septal wall by retracting it proximally as above mentioned. Subsequently, the mapping and ablation procedures mentioned above are repeated until the circular area surrounding the fossa ovalis is sufficiently and adequately covered.

In one specific application, for instance, the deployment control knob 44 on the operating handle portion 38 is then operated to advance the control shaft 43 distally, slighting raising the tips of bend sections 48 of each resilient arm more radially outward. The MASC device is unitarily advanced slightly forward moving the electrodes 50 of the electrode array out of contact with the septal tissue. The array of electrodes is than rotated about the longitudinal axis of the carrier assembly about 5°-10°. The electrode array 25 is then retracted proximally back into contact with the septal tissue of the Atrial Septum (AS). Once the mapping procedure confirms proper contact and/or presence of aberrant signals, the ablation procedure is repeated as noted above. In accordance with the present invention, this rotation about the septal puncture 27 in these 5°-10° increments is preferably repeated until the electrode array has been rotated at least 360°. Essentially, each region is overlapped about three times, forming a circular lesion that is preferably about 40 mm in diameter. This rotation sequence is especially significant since the electrodes of the proximal arm segment 46 of each resilient arm 45 are spaced asymmetrically to obtain an asymmetric reach along the septal wall for efficient and effective mapping and ablation.

It will be appreciated that in some instances, an aberrant signal detected on one side of the Atrial Septum (AS) may be addressed by ablating the septal wall from the other side of the septum. For example, the electrode array 25 of the MASC 21, deployed in the Left Atrium (LA), could the apply ablation energy to the Septal Wall (SW) from the Left Atrium (LA) side of the Atrial Septum (AS), to ablate an aberrant signal present on the Right Atrium (RA) side, such as by transferring heat through the tissue from one side to the other. In this situation, the selected power ratio, the maximum power applied and the duration must be sufficient to penetrate the Atrial Septum and disrupt the septal tissue in the Right Atrium (RA). For example, the power ratio may be selected as a 1:1 setting at 10 Watts for about 75 seconds of ablative contact to achieve adequate energy penetration into the tissue.

This approach is advantageous in that since an already deployed MASC 21, in the Left Atrium (LA), is being applied to address aberrant signal detected on the Septal Wall (SW) from the Right Atrium (RA) side, a catheter exchange and/or use of another ablation catheter may be eliminated. Alternatively an ablation device with forward facing electrodes (e.g. the MAAC catheter), deployed in the Right Atrium (RA), could apply ablation energy to the Right Atrium (RA) side of the Atrial Septum (AS), to ablate an aberrant signal on the Left Atrium (LA) side of the Atrial Septum (AS).

In yet another alternative embodiment, as shown in FIGS. 19 and 20, an alternative Septal Wall Ablation Catheter 21A is provided having a pair of opposed electrode arrays 25a and 25b that are configured to simultaneously contact and cooperatively ablate the Atrial Septum (AS) from the opposed Septal Walls (SWa and SWb) thereof. The opposed electrode arrays 25a and 25b each include a deployable carrier arm 71a and 71b carrying a plurality of associated electrodes 50a and 50b, cooperatively aligned in an ablation alignment as shown in FIG. 19. Once the opposed electrode arrays 25a and 25b are deployed, and oriented in a manner sandwiching the Atrial Septum (AS) therebetween, Bipolar RF energy can be delivered between the corresponding pairs of aligned electrodes 50a and 50b, or any other electrode pair, to effect ablation of the Septal Walls (SW). In this configuration, aberrant signals detected on either side of the Atrial Septum (AS) can be ablated (as well as any undetected signals within the Septal Wall).

In the embodiment illustrated, the respective carrier arm 71a, 71b of each the proximal and electrode array 25a, 25b is generally circular-shaped, similar to the deployed configuration of the electrode array of the PVAC 20. Each matched carrier arm 71a and 71b has substantially similar deployed diameters, and each supports a plurality of corresponding electrodes radially spaced therealong. The distal electrode array 25b, of course, incorporates proximally facing electrodes to ablate the Left Atrium side Septal Wall (SWb), while the proximal electrode array 25b incorporates distally facing electrodes to ablate the Right Atrium side Septal Wall (SWa). As mentioned, these opposed electrodes 50a and 50b, which are sized and function similarly to that of the PVAC, MASC and MAAC, are paired and aligned with one another when oriented in the ablative configuration (FIG. 19).

Briefly, it will be appreciated that while the proximal and distal electrode arrays 25a and 25b, in the deployed condition, are illustrated having a shape similar to that of the PVAC 20, albeit distally facing and proximally facing, the geometry of the electrode arrays may be similar to that of the MASC 21 and the MAAC 22 as well. That is, the proximal electrode array 25a may have two or more distal arm segments carrying the electrodes 50a and extending radially outward from the longitudinal axis thereof, while the distal electrode array 25b may have two or more proximal arm segments carrying the electrodes 50b and also extending radially outward from the longitudinal axis thereof. Such arm segments (i.e., the distal and proximal arm segments, are opposed and aligned with one another. Moreover, it is important that the opposed electrodes of the proximal electrode array be paired and aligned with those of the distal electrode array, in this embodiment as well.

Referring back to the embodiment of FIG. 19, the proximal electrode array 25a cooperates with the outer catheter shaft 40, and is configured to be deployed in the Right Atrium (RA), while the distal electrode array 25b cooperates with the inner catheter shaft 41, and is configured to be deployed in the Left Atrium (LA). As shown in FIG. 20, two or more radial support arms 72 movable affix the distal carrier arm 71b to the inner catheter shaft 41. Although not illustrated, both electrode arrays 25a and 25b are movable from a generally linear transport configuration, similar to that of the MASC 21 and MAAC 22, to the deployed configuration shown in FIGS. 19 and 20.

In the generally linear transport configuration, at least the inner catheter tube 41, along with the distal electrode array 25b, can be advanced into the Left Atrium (LA), via the transseptal sheath 65 (not shown in FIG. 19) extending through the septal puncture 27. During the penetration of the distal electrode array 25b into the Left Atrium (LA), the proximal electrode array 25a is retained in the Right Atrium (RA). Once both proximal electrode array 25a and the distal electrode array 25b are sufficiently clear of the respective Septal Wall (SWa and SWb), they can be moved to the deployed condition of FIG. 19, although out of contact with the either Septal Wall.

Subsequently, the outer catheter tube 40 can be advanced distally, while the inner catheter tube 41 can be retracted proximally until the respective electrode arrays 25a and 25b contact the respective Septal Walls (SWa and SWb), in the ablation alignment of FIG. 19. Hence, the proximal electrode array is positioned in compressive contact with the Right Atrium (RA) side Septal Wall (SWa), while the distal electrode array is positioned in tensile contact with the Left Atrium (LA) side Septal Wall (SWb), sandwiching the Atrial Septum (AS) therebetween.

As previously mentioned, in the ablation condition, the respective corresponding electrodes 50a and 50b are aligned with one another on opposed sides of the Atrial Septum (AS). Such alignment may be performed through a conventional key mechanism or the like (not shown). In an alternative embodiment, the corresponding electrodes are intentionally mis-aligned or off-set such as to transfer Bipolar energy at an acute angle across the tissue.

Applying conventional fluoroscopy techniques, and/or conventional mapping techniques, via the respective electrodes 50a and 50b, contact with the respective Septal Walls (SWa and SWb) can be confirmed. Once ablative contact is establish and confirmed, lesion formation can commence. In this particular embodiment, strictly Bipolar energy is delivered across the paired electrodes 50a and 50b. The power and timing settings, however, may be similar to that above-mentioned for the MASC 21. With the geometry and orientation of the electrodes of the corresponding arrays, a generally circular lesion may be formed, although perhaps not continuous, that extends across the Atrial Septum (AS) from one side of the Septal Wall (SWa) to the opposite side Septal Wall (SWb).

Once the initial lesion formation is completed, the proximal electrode array 25a can be retracted proximally and/or the distal electrode array 25b can be advanced distally, positioning one or both arrays out of contact with the respective Septal Wall (SWa and SWb). Similar to ablative procedure of the MASC, one or both the proximal electrode array 25a and the distal electrode array 25b can be rotated about a longitudinal axis thereof, as a unit, about 5°-10°. The outer catheter tube 40 can be advanced distally, while the inner catheter tube 41 can be retracted proximally until the respective electrode arrays 25a and 25b contact the respective Septal Walls (SWa and SWb). Once the mapping procedure confirms proper contact, the ablation procedure is repeated as noted above, collectively isolating the Atrial Septum AS.

As previously mentioned, once the intraluminal Atrial Septum ablation procedure has been completed, ample time should have passed since the completion of the initial PV ablation procedure to observe any Pulmonary Vein re-conduction that may occur. This time lag is one of the benefits of ablating the pulmonary veins before the septal tissue. Accordingly, in one specific embodiment, after the subsequent Atrial Septum ablation procedure, a DC Cardioversion procedure may be performed on the patient's Heart (H) to return the heartbeat to a normal sinus rhythm. Once normal sinus rhythm has returned, the Pulmonary Veins (PV) can be re-checked to determine whether any undesired re-conduction has occurred.

To determine and address whether re-conduction has occurred, the same PVAC 20 may be reinserted through the transseptal sheath 65, via the femoral vein, and into the Left Atrium (LA) where the carrier assembly is redeployed. Using the procedures set forth above, the ostial tissue surrounding each Pulmonary Vein (PV) can be remapped to locate any aberrant signals possibly resulting from re-conduction. Should any aberrant electrical activity be detected, the operator may energize the electrodes of the PVAC 20 through the RF Ablation Generator 16, using the procedures mentioned above.

Although the same PVAC 20 may be re-deployed in the second Pulmonary Vein ablation procedure, in an alternative embodiment, another PVAC device can be employed having an electrode array geometry proportionately similar, although either dimensionally smaller or larger, to that of the first PVAC 20. In this manner, the range of diametric deployment of the corresponding electrode arrays may differ, providing versatility to access and/or accommodate ostial tissue that might not have otherwise been efficiently accessible.

Alternatively, after the atrial septum ablation procedure, a third catheter 22 (e.g., the MAAC 22) can be employed to ablate any foci, rotors, drivers or other aberrant signals on the Left Atrial Walls. As previously mentioned, while other transluminal ablation catheter options are available to perform transluminal atrial wall ablation therapy, the MAAC is one example of a catheter that is adapted to perform this procedure.

These strategically placed ablation lesions that are created on the left Atrial Walls may prevent the propagation of any aberrant electrical activity that originates in the Pulmonary Veins, in other regions of the Atrial Wall, or on the Septal Wall itself. In accordance with the present invention, should any aberrant electrical activity be detected in the Left Atrial Walls, four strategic regions of the Left Atrial Walls are targeted (i.e., the Roof Wall (RW), the Posterior Wall (PW), the Superior Wall (SW), and the Floor Wall (FW) of the Left Atrium (LA)). Moreover, it has been observed that this procedure if performed more efficiently and effectively when the Left Atrial Roof Wall (RW) is initially targeted for ablation therapy followed by the Posterior Wall (PW); the Superior Wall (SW) and then the Floor Wall (FW).

Figure 21:
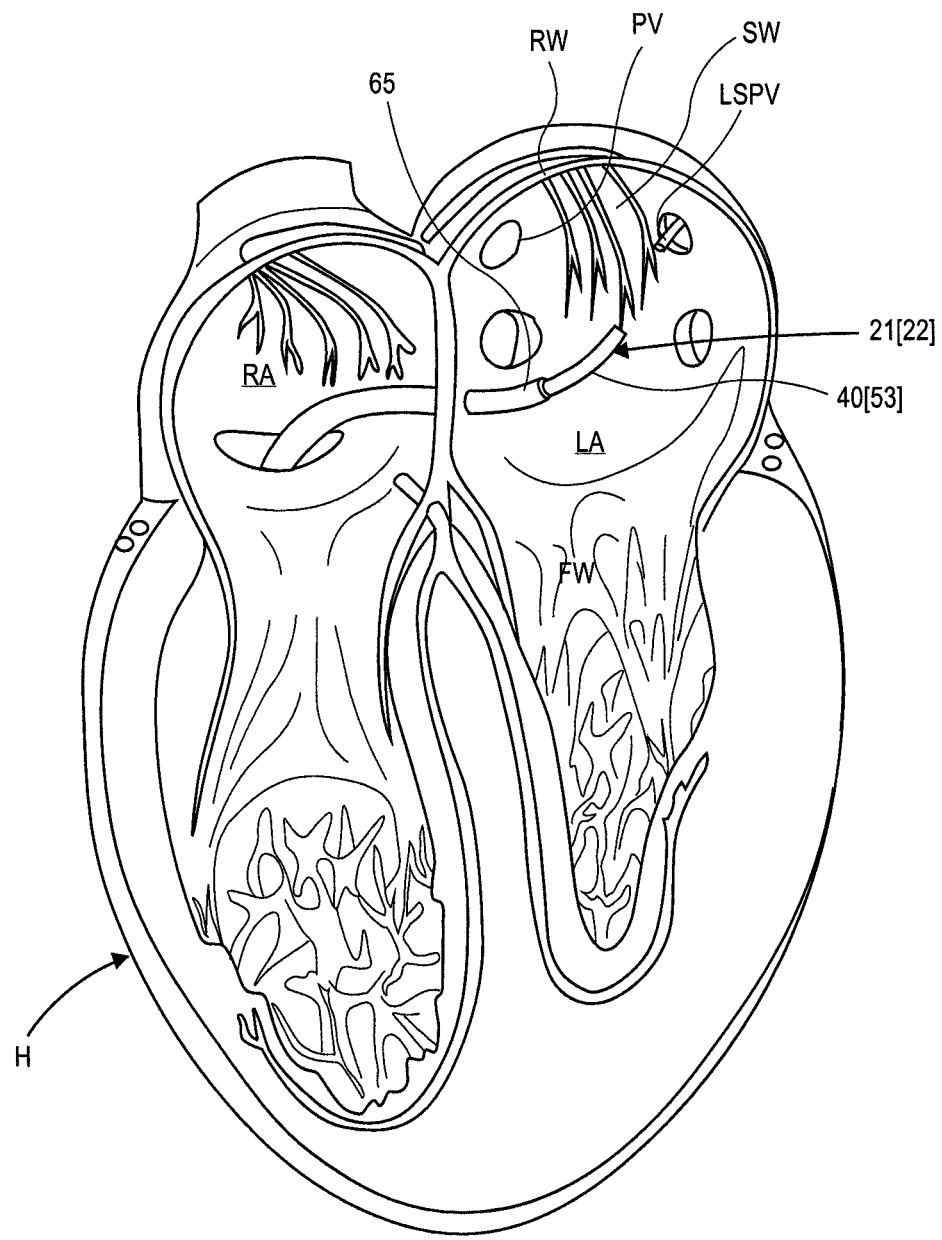
FIG. 21 is a front elevation view, in cross-section, of the patient's Heart (H) illustrating the advancement of a non-deployed electrode array of either a MASC or a MAAC into the Left Atrium (LA).

Turning now to FIG. 21, the MAAC electrode array 26 is oriented in the substantially linear transport configuration (FIG. 14) to facilitate advancement through the transseptal sheath, and thus, the vasculature. As mentioned, contact of the electrode array 26 with the capture device 54c itself, during sliding receipt within the lumen of the capture device causes the movement of the array from the biased deployed condition (FIG. 15 to the substantially linear transport condition (FIG. 14). Again, this is easily performed by holding the handle portion of outer catheter tube in one hand, and continued sliding of the capture device 54c against the electrode array 26 with the other hand. The electrode array may then be captured in, or received within the capture device 54c, in the stored or combined configuration.

The tip of the capture device 54c can then be inserted into the hemostasis valve or the like on the proximal portion of the sheath 65. Again using the technique above-mentioned, the electrode array 26 can then be safely transferred into the lumen of the sheath 65, already in the transport configuration (e.g., FIG. 14).

Similar to the MASC 21, the electrode array 26 and the outer catheter tube 53 of the MAAC 22 are advanced through the lumen of the transseptal sheath 65 until the distal end of the MAAC enters the Left Atrium (LA), via the sheath. Once the distal portion of the MAAC 22 is advanced into the Left Atrium (LA), past the distal end of the sheath 65, the electrode array 26 is be deployed. As the electrode array 26 of the MAAC emerges from the constraining walls of the sheath lumen, the resiliently biased support arms 58 are urged radially outward toward the deployed condition of FIG. 15.

Similar to the ablation procedure with the MASC 21, the distal tip of the transseptal sheath 65 can be retracted until the distal end thereof is removed from the Left Atrium (LA). Such removal will enable full deflection (e.g. bi-directional deflection) of the distal arm segments 61 of the resilient arms 58 of the MAAC. Such complete exposure allows these arms 58 to fully expand in the Left Atrium (LA) to the deployed configuration, creating a plurality of substantially triangular segments equally spaced, radially, about the longitudinal axis of the distal portion of the outer catheter tube 55. Each proximal arm segment 60 resiliently bends radially outwardly from the proximal connection with the outer catheter tube 55, while each distal arm segment 61 bends and extends radially inwardly and distally from the corresponding bend section 62 toward the central hub 56 oriented substantially at the longitudinally axis of the distal portion of the outer catheter tube. Accordingly, when the four support arms 58 are fully deployed (i.e., generally deploying from the generally linear transport configuration of FIG. 14 to the deployed configuration of FIGS. 15 and 16), the respective deployed support arms 58 form triangular segments where the distal arm segments 61 are oriented to extend in a direction distally from a plane intersecting the flexible bend sections 62.

Through manipulation of the pull wire 59, secured to the distal end of the inner catheter tube 55, the electrode array 26 may be directed toward the targeted atrial tissue to be ablated. This is performed by pulling the wire 59 proximally to deflect the distal end of the inner catheter tube. Using the pull wire 59, the operator can steer the array as needed to contact different areas of the Left Atrial Wall via the operation of the control knob 54 on the handle portion of the MAAC.

For anatomical locations that are often difficult to access, such as the Atrial Floor Wall (FW), the transseptal sheath 65 can be advanced distally towards the deployed electrode array. Through contact with the outer sheath 65, the transseptal sheath provides lateral support and/or compound curves (e.g. via deflection of the sheath as well) as the array is advanced forwardly, and into contact with the targeted tissue.

Once the array has been steered to face the targeted atrial tissue within the Left Atrium (LA) such as the Roof Wall (RW), the operator can advance the electrode array distally, pressing the deployed distal face of the array into contact with the Atrium Wall. Initially, this may cause the distal face of the electrode array to deform, resiliently, to a substantially flat configuration as shown. Given the concave curvature of the atrium chamber, the array is configured to deform to obtain distal arm segments with slightly convex curvature.

After contact has been established between the Atrium Wall and the electrode array 26, an electrophysiologist can map regions of the Atrial Walls and analyze electrical signals detected by the electrodes. If any arrhythmogenic foci or other aberrant signals are identified in the mapping procedure, the operator may energize any of the electrodes 57, as appropriate, to ablate the targeted tissue.

Again, similar to the above-mentioned ablation procedures for the Septum and Pulmonary Veins, a number of primary factors may be considered when determining the necessary energy ratios and timing settings to apply to the electrodes 57 in order to sufficiently and effectively form a proper ablation lesion in the Atrial Wall tissue. Such factors include the geometry and location of targeted region of the Heart (H) (including proximity to sensitive areas such as the esophagus), quality of the electrode/tissue contact, the type, thickness and/or density of the targeted tissue, the selected magnitude of the RF energy delivered to the electrodes, the type of RF energy applied (i.e., Monopolar, Bipolar or combination Monopolar-Bipolar energy), as well as the duration of the ablation. Bipolar RF energy may be applied between selected pairs of the electrodes 57, or Monopolar energy may be applied to any of the electrodes and a surface electrode mounted on the patient's body (typically on the back). A return electrode 73 may also be provided on the MAAC catheter 22, proximal to the electrode array 26, as shown in FIG. 7. The electrode temperature should be in the range of about 55° C., at the lower limit to about 65° C., at the upper limit thereof, with a target electrode temperature of at least 60° C. to assure a sufficient ablation.

Again, the combination of the MAAC 22, a few specific embodiments of which are disclosed in the '172 patent application, and RF Ablation Generator 16, as set forth in the '788 patent application, enables either Monopolar and Bipolar ablation applications, or any combination thereof. Depending upon the application and considered factors identified above, the settings can be matched for optimal performance. Preferably, it has been found that with the MAAC catheter, an initial power ratio setting of 1:1 (50% Bipolar 50% Monopolar, having a max power of about 10 W) is most beneficial when commencing the Atrial Wall ablation therapy procedure (initially about the Left Atrial Roof Wall).

Applying the above-mentioned range of parameters, a targeted duration for ablative contact between the Atrial Wall tissue and the electrodes of the MAAC array is in the range of at least about 45 seconds to no more than about 90 seconds. Optimally, in this instance, about 60 seconds of ablative contact is required to achieve adequate energy penetration into the tissue to ensure the necessary tissue ablation.

When a relatively lower than expected electrode temperature is measured at the electrodes (e.g. when a higher power setting is applied), this is generally a good indication that the electrodes are not in sufficient contact with the targeted tissue. In this situation, similar to the PVAC 20, the electrode array should be repositioned, preferably incrementally advanced distally to promote further contact with the atrial tissue. On the other hand, when a relatively higher than expected electrode temperature is measured at the electrodes (e.g. when a lower power setting is applied), this is generally a good indication that the electrodes may be embedded too deep within the cardiac tissue. Consequently, the electrode array 26 should be repositioned, preferably incrementally retracted proximally, reducing contact with the atrial tissue. The procedure may then be repeated to determine whether the electrode temperature is within satisfactory tolerances.

Similar to the MASC 21, albeit from the respective distal arm segments 61 of the resilient arms 58, a plurality of substantially linear lesions may be created using the electrodes 57 along each distal arm segment 61, operating the electrodes 57 in Bipolar mode. Due to the preferred geometry of the array of electrodes 57 for MAAC 22, as shown in FIG. 16, four substantially linear lesions can be formed each extending radially outward from a center thereof corresponding to the longitudinal axis of the electrode array 26, each equally spaced apart from an adjacent lesion by about 90°. In other applications, other therapeutic ablation lesions may be created using the electrodes pairs established between the electrodes of one arm and the electrodes of another arm, operating such pairs in Bipolar mode, and/or operating electrodes in conjunction with return electrodes in a Monopolar mode.

Regardless, in most instances, it may be necessary to perform multiple ablations in each of the four strategic Atrial Wall regions to satisfactorily address any detected aberrant signals. Once the initial ablation procedure has been completed, the entire electrode array 26 of the MAAC 22 can be slightly retracted proximally, moving the array out of contact with the targeted Atrial Wall tissue of the Roof Wall (RW). By operating the pull wire to slightly reposition the deployed electrode array and/or operating the control knobs 54 on the handle portion 52 (or applying torque to the outer catheter tube 40, the array may be incrementally rotated about its longitudinal axis of the array 26. Once repositioned, the array may be advanced distally to reseat the array against the Atrial Wall tissue of the Roof Wall (RW). After performing and repeating several mapping and ablation procedures, as mentioned above, satisfactory ablation of the Roof Wall (RW) is performed.

While an initial power ratio of 1:1 is applied when performing ablation therapy on the Atrial Wall tissue of the Roof Wall (RW), it will be appreciated that a power ratio of about 4:1 (80% Bipolar: 20% Monopolar) is preferred when ablating regions of the Atrial Wall considered to be more sensitive areas, such as the Posterior Wall (PW) (due to the proximity to the esophagus) and the ostia of the Pulmonary Veins (to avoid potential PV stenosis).

Once the ablation therapy has been satisfactorily and systematically completed for one or more of the Atrial Wall regions of the Roof Wall (RW), the Posterior Wall (PW), Superior Wall (SW), and the Floor Wall (FW), the electrode array 26 of the MAAC may be recaptured within the transseptal sheath and withdrawn. As the MAAC is withdrawn into the transseptal sheath 65, contact with the proximal arm segments 60 compress them radially inwardly, initially near the respective proximal ends. In turn, the bend section 62 forces the corresponding distal electrode arms 58 distally and inwardly. This initially splays the distal arm segments 61 toward a perpendicular relationship with the catheter axis. As the catheter is further withdrawn into the sheath, the distal arm segments become further splayed, such that they are significantly more distal to the proximal arms segments 60. Subsequently, the electrode array 26 can be captured within and withdrawn proximally through the transseptal sheath.

In some instances, before the electrode array of the MAAC 22 is entirely withdrawn, it may be deployed in the Right Atrium (RA) to ablate tissue in the Right Atrium (RA). Briefly, although not illustrated, the transseptal sheath 65 can be further withdrawn from the Right Atrium (RA), the distal end of which perhaps is withdrawn into the Inferior Vena Cava (IVC). This enables the electrode array 26 of the MAAC 22 to be fully deployed and deflected to perform the right atrial ablation.

In still another alternative embodiment, a single-tip ablation catheter may be employed to address any re-conduction that has occurred after the initial Pulmonary Vein ablation.

Alternatively or additionally, a single-tip ablation catheter can be employed, via the transseptal sheath 65, to perform any "touch-up" procedure (aberrant signal ablation) that may be necessary (e.g. in the left or right atria). The application of such single-tip catheters at this stage may be beneficial and/or necessary to remove all the necessary aberrant signals. Due to its linear geometry (i.e. does not include one or more carrier arms creating a two or three dimensional array of electrodes), Left Atrial tissue regions that are difficult to access via the PVAC, MASC and/or MAAC may be more accessible by a linear single-tip ablation catheters. Accordingly, such "touch-up" or other ablations can be more easily performed. An exemplary tip ablation catheter that can be used is the Tip-Versatile Ablation Catheter 70 ("TVAC") shown in FIGS. 22 and 23. This catheter includes a distal electrode array 75 comprised of a flexible carrier arm 76 having a single tip electrode 77 on a distal end thereof. Further, a plurality of ring-shaped electrodes 78 are spaced-apart along the carrier arm 76 and extending proximally from the tip electrode 77. On the opposite end of the TVAC 70 is a handle portion 80 with a control or steering knob 81 and an electrical connector (not shown). An elongated, flexible, outer catheter shaft 82 operably mounts the electrode array 75 to handle portion for operation and manipulation thereof. This exemplary catheter is more fully described in copending U.S. Provisional Patent Ser. No. 61/007,016 (hereinafter the '016 patent application), naming ROMAN et al. as inventors, filed Dec. 10, 2007, and entitled RF ENERGY DELIVERY SYSTEM AND METHOD, which is incorporated by reference herein in its entirety.

Similar to the PVAC, MASC and MAAC, the electrode array 75 of the TVAC 70 and the RF Ablation Generator 16 cooperate to deliver RF energy in Monopolar, Bipolar or combination Monopolar-Bipolar energy delivery modes, simultaneously or sequentially, with or without "off" or no energy delivered time durations. Accordingly, not only is single point ablation lesion formation possible from the single tip electrode 77, but linear and non-linear lesion formation is also available applying Monopolar, Bipolar or combination Monopolar-Bipolar energy delivery through the tip electrode 77 and one or more ring electrodes 78.

Figure 23:
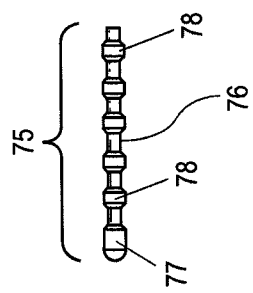
FIG. 23 is an enlarged side elevation view of a distal portion the Tip-Versatile Ablation Catheter of FIG. 22.

For example, referring now to FIG. 23, the electrode array 75 is shown as being substantially linear in a rested or natural position. It will be appreciated, however, that this flexible tip portion can be deflected to form a non-linear ablation lesion. One or more internal push/pull wires (not shown) may be provided, having one end internally affixed to the carrier arm 76 and an opposite end coupled to the steering control knob to enable steering and tip deflection thereof.

Depending upon the application and situation, the power ratios and other settings can be combined and adjusted for optimal performance. In a preferred embodiment, the below targets and ranges of parameters are used.

TABLE II

| T-VAC | Target/Preferred | Applicable | |
|---|---|---|---|
| | | Lower Limit | Upper Limit |
| Optimal Power Ratio | 1:1 (50% Bipolar:50% Monopolar) 4:1 for concern about collateral damage | 4:1 | Monopolar |
| Max Power | 45 Watts Tip 20 Watts Bands | | |
| Optimal Power Range | 20 Watts-35 Watts Tip 10 Watts-20 Watts Bands | | |

TABLE II-continued

| T-VAC | Target/Preferred | Applicable | |
|---|---|---|---|
| | | Lower Limit | Upper Limit |
| Target Temp | 65° C. | 60° C. | 70° C. |
| Target Time | 90 seconds | 45 seconds | 120 seconds |
| Target Placement Location | R-Sided Flutter - Isthmus VT - Ventricle AF - L-Atrium | | |
| Secondary Power Ratio | Monopolar | | |

An additional advantage to the ablation procedures described herein is the use of a single transseptal sheath can be used throughout the entire ablation procedure. Known ablation treatments require two transseptal sheaths to be placed in the patient simultaneously. One sheath provides access to the heart for a mapping catheter, while the second sheath provides access for an ablation catheter. The catheters described herein are capable of both mapping and ablating using the same electrodes, or with combinations of mapping and ablating electrodes. This dual functionality of each catheter avoids the need for both a mapping catheter and an ablation catheter to be used, and thus allows for the use a single transseptal sheath. This is advantageous because using two sheaths requires two transseptal punctures. In addition to the procedure time and cost increases, multiple transseptal sheaths result in additional trauma to the septum which may result in increased pain as well as increased risk of improper septal healing (e.g. leaking).

Referring again to FIG. 1, and in accordance with the present invention, the intraluminal ablation therapy system 15 for systematically treating continuous atrial fibrillation generally includes the Multi-Channel RF Ablation Generator 16, an ECG interface 17, and an assembly 18 of cardiac ablation catheters 20, 21 and 22 (while only two catheters may also be used). These ablation catheters are selectively serially connected to a single RF Ablation Generator, via the ECG interface 17, enabling selective operation of any one of the ablation catheters one at a time. Effectively, the RF generator 16, the Cardiac Ablation Catheters 20-22 and ECG Interface unit 17 are designed to be operated in the same manner as other commercially available electrophysiology ablation and mapping catheters.

Briefly, the RF Ablation Generator unit 16 functions to generate the ablative RF energy, as supplied to selected catheter electrodes or between selected pairs of electrodes for each respective electrode array, necessary to ablate cardiac tissue. The ECG monitoring unit 24, on the other hand, is provided to monitor and map signals detected by selected electrode pairs of same electrode of each electrode array. These two units (i.e., the RF Generator unit 16 the ECG Monitoring unit 24) are interfaced in parallel, via the ECG interface 17, to the assembly 18 of ablation catheters 20-22. The ECG interface unit 17 electrically isolates the ECG monitoring unit 24 from any damaging signals generated by the RF Generator 16. Any RF energy signals reaching the ECG monitoring unit, especially signals of the magnitude generated by the RF Generator, would likely damage the monitor unit's amplifiers. ECG interface unit 17 preferably is also configured to isolate the ECG monitoring unit from electrical noise generated by the delivery of the RF energy.

More specifically, the Multi-Channel RF Ablation Generator 16 is configured to generate and control the delivery of RF energy based on temperature feedback from the respective thermocouple of each electrode. Each electrode, thus, can be independently monitored, and be delivered temperature-controlled RF energy. Energy delivery is further automatically duty-cycled in order to maximize the delivery of RF energy to the electrode, based on the measured tissue temperature. Hence, as the tissue temperature increases due to delivery of RF energy (resistive heating), the electrodes in turn increase in temperature, as monitored by the corresponding thermocouple. The temperature measurements, for the most part, are performed between RF duty cycles (off-cycles) to minimize interference and to optimize accuracy of temperature readings.

Proprietary electrodes, such as those in the electrode array of the PVAC 20, the MASC 21 and the MAAC 22, are designed and optimized to efficiently remove the heat from the tissues resistive heating, while the duty-cycle is optimized to match the thermal heat transfer properties of the electrode to allow rapid electrode cooling. By delivering energy to the tissue in this manner, lesion growth is maximized using only the amount of RF energy necessary to create the lesion desired for that patient's condition (i.e., a tailored therapy).

The RF Generator 16 applied in accordance with the present invention is capable of delivering Bipolar energy alone, Monopolar energy alone, or a combination of both Bipolar and Monopolar RF energy. As mentioned, one particularly suitable RF Ablation Generator 16 is that described in our '788 patent application entitled RF ENERGY DELIVERY SYSTEM AND METHOD.

For Monopolar energy delivery, the RF energy is conducted from one or more selected catheters electrodes, through the targeted cardiac tissue to a ground pad, such as a conductive pad attached to the back of the patient. The high concentration of energy at the electrode site causes localized tissue ablation. In contrast, for Bipolar energy delivery, the RF energy is conducted through the targeted cardiac tissue between a selected first electrode to a paired second electrode. Bipolar energy delivery results in more precise, shallow lesions while Monopolar delivery results in deeper lesions.

When Monopolar, Bipolar and/or a combination of Bipolar:Monopolar energy delivery is available, a more tailored ablation treatment can be provided to more particularly treat a patient's continuous atrial fibrillation condition. Pre-programmed settings for energy delivery are available to the electrode array of each catheter, typically 4:1 (4 Bipolar cycles to every 1 Monopolar cycle or 80% Bipolar: 20% Monopolar); 2:1 (2 Bipolar cycles to every 1 Monopolar cycle); 1:1 (1 Bipolar cycles to every 1 Monopolar cycle); Bipolar only and Monopolar only. It will be appreciated of course that other power ratios are available.

In general, a lower power setting with a power ratio of 4:1 is initially applied, and is the default position, since it provides adequate Monopolar energy for depth and adequate Bipolar energy to bridge the lesions between the two selected electrodes. Typical power outputs are between 4 and 8 watts of power, with good tissue contact and catheter apposition. Moreover, this initial default setting is applied to targeted tissue areas considered to be more sensitive, such as the ostia of the Pulmonary Veins (PV). When performing the initial PV Ablation procedure using the PVAC 20, such lower power setting significantly reduces the potential of PV stenosis. Similarly, during the Atrial Wall Ablation Procedure by the MAAC 22, such default setting may also be applied to the Posterior Wall (PW) due to the proximity of this cardiac tissue to the esophagus. In contrast, a higher power with a ratio of 1:1 is initially applied when performing ablation therapy on the atrial wall tissue of the Roof Wall (RW), as well as the Atrial Septum Wall Ablation Procedure by the MASC 21.

The Multi-Channel RF Ablation Generator 16 is further capable of monitoring and tracking each electrode temperature independently, as mentioned. During the Bipolar phase of the energy delivery, the generator monitors the two selected electrodes that are paired to create the Bipolar loop. In a preferred embodiment, the RF Generator will then regulate and deliver RF energy based on the higher of the two measured electrodes temperatures. For instance, if the set target temperature of the electrodes is 60° C. and one of the two electrodes is monitored at 55° C., while the other electrode is monitored to be at 50° C., the generator will selectively limit energy delivery based on the needs of one electrode measured at 55° C. This prevents either electrode of the pair from ever significantly surpassing the set target temperature. In contrast, during the Monopolar phase of the energy delivery, the RF Generator will deliver RF energy to each electrode solely based on the temperature measured by its corresponding thermocouple.

In one specific embodiment, the RF Generator includes twelve channels through which RF energy can be independently delivered. More or less channels can be provided, of course, depending upon the application. Twelve channels, however, is consistent with the number of electrodes provided on the electrode array 25 of one specific embodiment of the MASC 21 in FIG. 14. In contrast, only eight channels are activated when the MAAC 22 is applied, in the one specific embodiment of FIG. 16, while ten channels are activated when the specific embodiment of the PVAC 20 of FIG. 10 is applied. For each RF energy channel, there is an independent temperature acquisition channel and an associated temperature control loop. Energy delivery is controlled by the user-selected target tissue temperature. Only the energy necessary for heating the tissue to the desired temperature is delivered.

Most commercially available ECG monitoring units can be used and connected to the intraluminal ablation therapy system 15, via ablation interface unit 17, to provide tissue mapping capabilities (via the electrodes of the ablation catheters) either before or after cardiac tissue ablation. Utilizing predetermined Electrogram Recording System settings for the ECG unit 24, together with connected pair or pairs of electrodes selected for each of the PVAC 20, the MASC 21 and the MAAC 22, an electrophysiologist can apply conventional mapping techniques to map the targeted cardiac tissue. By way of example, electrical signals detected between each pair of electrodes (bi-pole) enable mapping of tissue electrical activity.

Examples of conventional ECG monitoring units suitable for use with the present invention include, but are not limited to, the Prucka System, (e.g. model nos. 200, 4000 & 7000); the Bard System (e.g. the LabSystem Pro model); the EP Med System (e.g. the EP-WorkMate® model); and the Cardiotek System. Each particular ECG system incorporated may require system settings particular to that system. However, many electrogram recording system settings are more common between the units and have been determined to yield exceptional tissue mapping results by the electrode pairs of all ablation catheters 20-22.

In an exemplary procedure using the Prucka System, the electrogram recording system settings are as follows: Gain—(5000) or "1 level above current circular (PV) mapping catheter gain"; High Pass Filter—(100 Hz); Low Pass Filter—(500 Hz); Notch filter—(Off); Stim—(No)

For all recording systems, six bi-pole channels are provided on the recording system. As the ablation catheters are switched from the PVAC, to the MASC to the MAAC, bi-pole channels can be selectively added or removed from the recording screen. For instance, the PVAC 20 requires only five Bipolar tracings (10 electrodes), the MASC requires six Bipolar tracings (12 electrodes) and the MAAC requires only four Bipolar tracings (eight electrodes).

In accordance with the present invention, the ECG interface unit 17 is applied for interrogation of the patient's intracardiac electrograms prior to, and following, the tissue ablation cycle. It will be appreciated that this interface also provides an electrical connection (interface) between the Multi-Channel RF Ablation Generator 16, the assembly of Cardiac Ablation Catheters, and the ECG monitoring unit 24. For instance, the ECG Interface unit 17 includes a twelve channel signal splitter that allows for connection of the amplifiers located within the Prucka ECG monitoring unit to the ablation therapy system 15. In addition the patient return electrode 68 is connected to the interface unit.

Just as important, the ECG interface unit 17 of FIG. 1 electrically isolates the ECG monitoring unit 24 from any damaging signals generated by the RF Generator 16. Any RF energy signals reaching ECG monitoring unit, especially signals of the magnitude generated by the RF Generator, would certainly damage the unit's amplifiers. Hence, during an ablation cycle, while significant power signals are being delivered to electrodes of the cardiac ablation catheter, the ECG interface unit 17 also isolates these power signals from the ECG monitoring unit, as well as shielding the same from other electrical noise.

Although the present invention has been described in connection with the preferred form of practicing it and modifications thereto, those of ordinary skill in the art will understand that many other modifications can be made thereto within the scope of the claims that follow. For example, the RF Generator, the ECG Interface Unit and the ECG Monitoring Unit could be integrated into a single unit. Accordingly, it is not intended that the scope of the invention in any way be limited by the above description, but instead be determined entirely by reference to the claims that follow.

What is claimed is:

1. A systematic method of treating continuous atrial fibrillation comprising:
   (a) transseptally accessing a left atrium of a heart of a patient through a puncture in an atrial septum;
   (b) ablating tissue surrounding one or more pulmonary veins to treat aberrant conductive pathways therethrough;
   (c) ablating septal tissue surrounding the puncture to treat aberrant conductive pathways therethrough; and
   (d) ablating left atrial wall tissue,
   wherein (a), (b), and (c) are performed before (d).

2. The method of claim 1 wherein ablating the septal tissue surrounding the puncture occurs after ablating the tissue surrounding one or more pulmonary veins.

3. The method according to claim 1 wherein,
   ablating the tissue surrounding the one or more pulmonary veins comprises sensing electrical signals of the pulmonary vein ostial tissue through one or more electrodes of an electrode array of a first catheter; and
   upon determining that the electrodes of the electrode array of the first catheter are disposed over an aberrant signal of the pulmonary vein ostial tissue, passing energy through the electrode array of the first catheter to ablate a portion of the pulmonary vein ostial tissue.

4. The method according to claim 3 wherein,
   ablating septal tissue comprises sensing electrical signals of the septal tissue surrounding the puncture through one or more electrodes of an electrode array of a second catheter; and
   upon determining that the electrodes of the electrode array of the second catheter are disposed over an aberrant signal of the septal tissue, passing energy through the electrode array of the second catheter to ablate a portion of the septal tissue.

5. The method according to claim 1 wherein ablating tissue surrounding the one or more pulmonary veins and the septal tissue comprises passing energy that is selected from the group consisting of:
   magnetic energy, microwave energy, radiofrequency energy, thermal energy and a combination thereof.

6. The method according to claim 1 wherein ablating tissue surrounding the one or more pulmonary veins and the septal tissue comprises passing energy that is selected from the group consisting of acoustic energy, chemical energy, photonic energy, mechanical energy, radiation energy, and a combination thereof.

7. The method according to claim 4 wherein, passing energy through the electrode arrays of the first catheter and the second catheter includes passing monopolar radiofrequency energy between at least one electrode of the electrode arrays and a ground pad, and passing bipolar radiofrequency energy between at least two electrodes of the electrode arrays.

8. The method according to claim 3 wherein, ablating tissue surrounding one or more pulmonary veins further includes selectively moving the electrode array of the first catheter to other areas of the pulmonary vein ostial tissue surrounding the one or more pulmonary veins, and repeating the sensing electrical signals of the pulmonary vein ostial tissue and passing energy through the electrode array of the first catheter to ablate the other areas of the pulmonary vein ostial tissue.

9. The method according to claim 8 wherein, selectively moving the electrode array of the first catheter includes incrementally rotating the electrode array about an axis of the first catheter.

10. The method according to claim 9 wherein,
    incrementally rotating the electrode array about the axis of the first catheter comprises rotating the electrode array about 90.degree.

11. The method according to claim 8 wherein,
    ablating tissue surrounding one or more pulmonary veins comprises ablating pulmonary vein ostial tissue surrounding a left superior pulmonary vein;
    subsequently ablating pulmonary vein ostial tissue surrounding a right superior pulmonary vein; and
    subsequently ablating pulmonary vein ostial tissue surrounding a left inferior pulmonary vein.

12. The method of claim 8 further comprising ablating pulmonary vein ostial tissue surrounding a right inferior pulmonary vein after ablating the tissue surrounding the left inferior pulmonary vein.

13. The method according to claim 3 wherein,
    ablating tissue surrounding one or more pulmonary veins further includes advancing the first catheter along a guide wire that is selectively inserted into one of the pulmonary veins.

14. The method according to claim 4 further including:
    prior to ablating septal tissue, retracting the first catheter proximally toward the atrial septum such that the electrode array of the first catheter contacts a wall of the atrial septum;
    sensing electrical signals of the septal tissue surrounding the puncture through one or more electrodes of the electrode array of the first catheter; and upon determining that the electrodes of the electrode array of the first catheter are disposed over an aberrant signal of the septal tissue, ablating the septal tissue.

15. The method according to claim 8 wherein,
ablating septal tissue further includes selectively moving the electrode array of the second catheter to other areas of the septal tissue surrounding the puncture, and repeating the sensing electrical signals of the septal tissue surrounding the puncture and passing energy through the electrode array of the second catheter to ablate the other areas of the septal tissue.

16. The method according to claim 15 wherein,
selectively moving the electrode array of the second catheter includes incrementally rotating the electrode array about an axis of the second catheter.

17. The method according to claim 16 wherein,
incrementally rotating the electrode array about the axis of the second catheter comprises rotating the electrode array in a range of about 5.degree. to about 15.degree.

18. The method according to claim 1, further including:
after ablating septal tissue, performing a left atrial wall ablation procedure on left atrial wall tissue to ablate at least one of a roof wall, a posterior wall, a superior wall, and a floor wall of the left atrium of the heart in a manner to treat aberrant conductive pathways therethrough.

19. The method according to claim 18 wherein,
ablating tissue surrounding one or more pulmonary veins includes sensing electrical signals of the pulmonary vein ostial tissue through one or more electrodes of an electrode array of a first catheter,
upon determining that the electrodes of the electrode array of the first catheter are disposed over an aberrant signal of the pulmonary vein ostial tissue, passing energy through the electrode array of the first catheter to ablate a portion of the pulmonary vein ostial tissue; and
wherein ablating septal tissue includes sensing electrical signals of the septal tissue surrounding the puncture through one or more electrodes of an electrode array of a second catheter, and
upon determining that the electrodes of the electrode array of the second catheter are disposed over an aberrant signal of the septal tissue, passing energy through the electrode array of the second catheter to ablate a portion of the septal tissue; and
wherein performing the left atrial wall ablation procedure includes sensing electrical signals of the left atrial wall tissue through one or more electrodes of an electrode array of a third catheter,
upon determining that the electrodes of the electrode array of the third catheter are disposed over an abberant signal of the left atrial wall tissue, passing energy through the electrode array of the third catheter to ablate a portion of the left atrial wall tissue.

20. The method according to claim 19 wherein,
performing the left atrial wall ablation procedure further includes selectively moving the electrode array of the third catheter to other areas of the left atrial wall tissue, and repeating the sensing electrical signals of the left atrial wall tissue and passing energy through the electrode array of the third catheter to ablate the other areas of the left atrial wall tissue.

21. The method according to claim 20 wherein,
performing the left atrial wall ablation procedure further includes ablating the roof wall;
subsequently ablating the posterior wall;
subsequently ablating the superior wall; and
subsequently ablating the floor wall.

22. The method according to claim 19 wherein,
the electrode array of the third catheter includes two or more resilient support arms, each support arm having a proximal arm segment and a distal arm segment connected therebetween by a resilient bend point, each distal arm segment including a plurality of the electrodes of the electrode array of the third catheter disposed thereon in a spaced-apart manner; and
before performing the left atrial wall ablation procedure, deploying the two or more support arms to an expanded condition wherein each distal arm segment extends generally radially outward from a longitudinal axis of the third catheter, creating an acute angle at each bend point between the respective distal arm segment and the corresponding proximal arm segment, and such that during advancing of the electrode array of the third catheter, the plurality of electrodes disposed on the respective distal arm segments are moved into contact with the left atrial wall tissue.

23. The method of claim 19 wherein passing energy through the electrode array includes passing energy through a tip electrode included on the third catheter.

24. The method according to claim 1 further including:
after performing the atrial septum ablation procedure, performing a subsequent endocardial pulmonary vein ablation procedure on the pulmonary vein ostial tissue surrounding one or more of the pulmonary veins in a manner treating aberrant re-conductive pathways therethrough.

25. The method according to claim 1, further including:
after ablating septal tissue, performing a touch-up ablation procedure with a single point tip ablation catheter which comprises a tip electrode.

26. The method according to claim 25, wherein
performing the touch-up ablation procedure includes sensing electrical signals of the left atrial wall tissue through the tip electrode of the single point tip ablation catheter, and
upon determining that the tip electrode of the single point tip ablation catheter is disposed over an aberrant signal of the left atrial wall tissue, passing energy through the electrode to ablate a portion of the left atrial wall tissue.

27. A systematic method for treating continuous atrial fibrillation comprising:
transseptally accessing a left atrium of a heart of a patient through a puncture in an atrial septum with a first catheter comprising an electrode array disposed substantially at a distal end thereof;
ablating tissue surrounding one or more pulmonary veins to treat aberrant conductive pathways therethrough by advancing the electrode array of the first catheter into contact with the tissue surrounding the one or more pulmonary veins;
transseptally accessing the left atrium through the puncture with a second catheter comprising an electrode array disposed substantially at a distal end thereof;
ablating septal tissue surrounding the puncture to treat aberrant conductive pathways therethrough by retracting the electrode array of the second catheter into contact with the septal tissue; and
ablating left atrial wall tissue,
wherein ablating the septal tissue occurs after ablating the tissue surrounding the one or more pulmonary veins, and ablations of septal tissue and pulmonary vein tissue occur before ablation of left atrial wall tissue.

28. The method according to claim 27 wherein,
ablating tissue surrounding one or more pulmonary veins includes sensing electrical signals of the pulmonary vein ostial tissue through one or more electrodes of the electrode array of the first catheter; and
upon determining that the electrodes of the electrode array of the first catheter are disposed over an aberrant signal of the pulmonary vein ostial tissue, passing energy through the electrode array of the first catheter to ablate a portion of the pulmonary vein ostial tissue.

29. The method according to claim 28 wherein,
ablating tissue surrounding one or more pulmonary veins further includes selectively moving the electrode array of the first catheter to other areas of the pulmonary vein ostial tissue surrounding the one or more pulmonary veins, and repeating the sensing electrical signals of the pulmonary vein ostial tissue and passing energy through the electrode array of the first catheter to ablate the other areas of the pulmonary vein ostial tissue.

30. The method according to claim 29 wherein,
selectively moving the electrode array includes incrementally rotating the electrode array about an axis of the first catheter.

31. The method according to claim 30 wherein,
incrementally rotating the electrode array about the axis of the first catheter comprises rotating the electrode array about 90.degree.

32. The method according to claim 30 wherein,
ablating tissue surrounding one or more pulmonary veins further includes ablating the pulmonary vein ostial tissue surrounding at least a left superior pulmonary vein, a left inferior pulmonary vein, and a right superior pulmonary vein.

33. The method according to claim 30 wherein,
ablating tissue surrounding one or more pulmonary veins includes ablating the pulmonary vein ostial tissue surrounding the left superior pulmonary vein;
subsequently ablating the pulmonary vein ostial tissue surrounding the right superior pulmonary vein; and
subsequently ablating the pulmonary vein ostial tissue surrounding the left inferior pulmonary vein.

34. The method according to claim 33, further comprising subsequently ablating the pulmonary vein ostial tissue surrounding the right inferior pulmonary vein after ablating the pulmonary vein ostial tissue surrounding the left inferior pulmonary vein.

35. The method according to claim 27 wherein ablating tissue surrounding the one or more pulmonary veins and the septal tissue comprises passing energy that is selected from the group consisting of: magnetic energy, microwave energy, radiofrequency energy, thermal energy and a combination thereof.

36. The method according to claim 27 wherein ablating tissue surrounding the one or more pulmonary veins and the septal tissue comprises passing energy that is selected from the group consisting of acoustic energy, chemical energy, photonic energy, mechanical energy, radiation energy, and a combination thereof.

37. The method according to claim 28 wherein,
passing energy through the electrode array of the first catheter includes passing Monopolar radiofrequency energy between at least one electrode of the electrode array and a ground pad, and passing Bipolar radiofrequency energy between at least two electrodes of the electrode array.

38. The method according to claim 27 wherein,
ablating tissue surrounding one or more pulmonary veins further includes advancing the first catheter along a guide wire that is selectively inserted into one of the pulmonary veins.

39. The method according to claim 27 wherein,
the first catheter includes a flexible carrier assembly supporting a plurality of the electrodes of the electrode array in a spaced manner, and
before ablating tissue surrounding one or more pulmonary veins, deploying the carrier assembly of the first catheter to a deployed condition from a near linear geometry to a partially helical or spiral geometry.

40. The method according to claim 39 wherein, when the carrier assembly is deployed to the deployed condition and is positioned proximate to an antrum of one of the pulmonary veins, adjusting one of a plane and a shape of the carrier assembly to achieve contact of the electrode array with the pulmonary vein ostial tissue.

41. The method according to claim 40 wherein,
adjusting one of the plane and the shape of the carrier assembly includes decreasing and increasing the diameter of the spiral geometry of the carrier assembly.

42. The method according to claim 39 wherein,
ablating tissue surrounding one or more pulmonary veins includes creating a substantially continuous, non-linear lesion in the pulmonary vein ostial tissue.

43. The method according to claim 42 wherein,
ablating tissue surrounding one or more pulmonary veins includes sensing electrical signals of the pulmonary vein ostial tissue through one or more of the electrodes of the electrode array of the first catheter; and
upon determining that the electrodes of the electrode array of the first catheter are disposed over an aberrant signal of the pulmonary vein ostial tissue, passing energy through the electrode array of the first catheter to ablate a portion of the pulmonary vein ostial tissue.

44. The method according to claim 43 wherein,
ablating tissue surrounding one or more pulmonary veins further includes selectively moving the carrier assembly having the helical or spiral geometry to other areas of the pulmonary vein ostial tissue surrounding the one or more pulmonary veins, and repeating the sensing electrical signals of the pulmonary vein ostial tissue and passing energy through the electrode array of the first catheter to ablate a portion of the pulmonary vein ostial tissue.

45. The method according to claim 44 wherein,
selectively moving the carrier assembly having the helical or spiral geometry includes incrementally rotating the electrode array about an axis of the first catheter.

46. The method according to claim 27 wherein,
transseptally accessing the left atrium of the heart of the patient through the puncture in the atrial septum with the first catheter is performed by advancing the distal end of the first catheter through a lumen of a transseptal sheath that extends through the puncture; and
prior to ablating tissue surrounding one or more pulmonary veins, withdrawing the transseptal sheath proximally until a distal end of the transseptal sheath is removed from the left atrium of the heart.

47. The method according to claim 46 wherein,
withdrawing the transseptal sheath proximally includes retracting the transseptal sheath proximally at least until the distal end of the transseptal sheath is contained in a right atrium of the heart.

48. The method according to claim 27 further including:
prior to accessing the left atrium through the puncture with a second catheter, retracting the first catheter in a deployed condition toward the atrial septum such that the electrode array of the first catheter contacts a wall of the atrial septum;
sensing electrical signals of the septal tissue through one or more electrodes of the electrode array of the first catheter; and
upon determining that the electrodes of the electrode array of the first catheter are disposed over an aberrant signal of the septal tissue, accessing the left atrium through the puncture with a second catheter.

49. The method according to claim 27 wherein,
ablating septal tissue includes sensing electrical signals of the septal tissue surrounding the puncture through one or more of the electrodes of the electrode array of the second catheter; and
upon determining that the electrodes of the electrode array of the second catheter are disposed over an aberrant signal of the atrial septum tissue, passing energy through the electrode array of the second catheter to ablate a portion of the septal tissue.

50. The method according to claim 49 wherein,
ablating septal tissue further includes selectively moving the electrode array of the second catheter to other areas of the septal tissue surrounding the puncture, and repeating the sensing electrical signals of the septal tissue surrounding the puncture and passing energy through the electrode array of the second catheter to ablate the other areas of the septal tissue.

51. The method according to claim 50 wherein,
selectively moving the electrode array of the second catheter includes incrementally rotating the electrode array about an axis of the second catheter.

52. The method according to claim 51 wherein,
incrementally rotating the electrode array about the axis of the second catheter comprises rotating the array in the range of about 5.degree. to about 15.degree.

53. The method according to claim 27 wherein,
the electrode array of the second catheter includes two or more resilient support arms, each support arm having a proximal arm segment and a distal arm segment connected therebetween by a resilient bend point, each said proximal arm segment including a plurality of electrodes of the electrode array of the second catheter disposed thereon in a spaced-apart manner; and
before ablating septal tissue, deploying the two or more support arms to an expanded condition wherein each proximal arm segment and each distal arm segment extends generally radially outward from a longitudinal axis of the second catheter, creating an acute angle at each bend point between the respective distal arm segment and the corresponding proximal arm segment, and such that during retracting of the second catheter, the plurality of electrodes disposed on the respective proximal arm segments are moved into contact with the septal tissue.

54. The method according to claim 53 wherein,
ablating septal tissue includes creating a substantially continuous, substantial linear lesion corresponding to a respective proximal arm segment and extending radially outward from the puncture.

55. The method according to claim 54 wherein,
ablating septal tissue includes sensing electrical signals of the septal tissue through one or more electrodes of the electrode array of the second catheter; and upon determining that the electrodes of the electrode array of the second catheter are disposed over an aberrant signal of the septal tissue, passing energy through the electrode array of the second catheter to ablate a portion of the septal tissue.

56. The method according to claim 55 wherein, ablating septal tissue further includes selectively moving the two or more support arms of the second catheter to other areas of the septal tissue surrounding the puncture, and repeating the sensing electrical signals of the septal tissue surrounding the puncture and passing energy through the electrode array of the second catheter to ablate the other areas of the septal tissue.

57. The method according to claim 56 wherein, selectively moving the two or more support arms of the second catheter includes incrementally rotating the respective distal arm segments about an axis of the second catheter.

58. The method according to claim 27 wherein,
transseptally accessing the left atrium through the puncture with the second catheter is performed by advancing the distal end of the second catheter through a lumen of a transseptal sheath that extends through the puncture of the atrial septum; and
prior to ablating septal tissue, withdrawing the transseptal sheath proximally until a distal end of the transseptal sheath is removed from the left atrium of the heart.

59. The method according to claim 58 wherein,
withdrawing the transseptal sheath proximally includes retracting the transseptal sheath proximally at least until the distal end of the transseptal sheath is contained in a right atrium of the heart.

60. The method according to claim 27 wherein,
the first catheter includes a flexible carrier assembly supporting a plurality of the electrodes of the electrode array in a spaced manner, and before performing the pulmonary vein ablation procedure, deploying the carrier assembly of the first catheter to a deployed condition from a near linear geometry to a partially helical or spiral geometry;
the electrode array of the second catheter includes two or more resilient support arms, each support arm having a proximal arm segment and a distal arm segment connected therebetween by a resilient bend point, each said proximal arm segment including a plurality of electrodes of the electrode array of the second catheter disposed thereon in a spaced-apart manner; and
before ablating septal tissue, deploying the two or more support arms to an expanded condition wherein each proximal arm segment and each distal arm segment extends generally radially outward from a longitudinal axis of the second catheter, creating an acute angle at each bend point between the respective distal arm segment and the corresponding proximal arm segment, and such that during retracting of the second catheter, the plurality of electrodes disposed on the respective proximal arm segments are moved into contact with the septal tissue.

61. The method according to claim 60 wherein,
the first catheter is a PVAC device having the electrode array and ablates tissue in a distal facing direction, and the second catheter is a MASC device having the electrode array and ablates tissue in a proximal facing direction.

62. The method according to claim 39, wherein after ablating septal tissue, the method further includes ablating tissue surrounding one or more pulmonary veins with a third catheter having an electrode array that is at least substantially similar in electrode orientation to the electrode array of the first catheter.

63. The method of claim 62 wherein the first and third catheters are the same catheter, and wherein the flexible carrier assembly has a plurality of deployed conditions with a partially helical or spiral geometry, wherein each of the plurality of deployed conditions has a different diameter.

64. The method of claim 62 wherein the third catheter comprises a flexible carrier assembly with a deployed condition comprising a partially helical or spiral geometry, and wherein the diameter of the flexible carrier assembly of the third catheter in the deployed condition is different than a diameter of the flexible carrier assembly of the first catheter in the deployed condition.

65. The method according to claim 27, further including:
after ablating septal tissue, transseptally accessing the left atrium through the puncture with a third catheter having an electrode array disposed on the distal end of the third catheter; and
performing a left atrial wall ablation procedure on left atrial wall tissue by advancing the electrode array of the third catheter toward and into contact with the left wall atrial tissue to ablate at least one of a roof wall, a posterior wall, a superior wall, and a floor wall of the left atrium of the heart in a manner treating aberrant conductive pathways therethrough.

66. The method according to claim 65 wherein,
performing the left atrial wall ablation procedure includes sensing electrical signals of the left atrial wall tissue through one or more of the electrodes of the electrode array of the third catheter; and
upon determining that the electrodes of the electrode array of the third catheter are disposed over an aberrant signal of the left atrial wall tissue, passing energy through the electrode array of the third catheter to ablate a portion of the left atrial wall tissue.

67. The method according to claim 66 wherein,
performing the left atrial wall ablation procedure further includes selectively moving the electrode array of the third catheter to other areas of the left atrial wall tissue, and repeating the sensing of electrical signals of the left atrial wall tissue and passing energy through the electrode array of the third catheter to ablate the other areas of the left atrial wall tissue.

68. The method according to claim 67 wherein,
performing the atrial wall ablation procedure further includes ablating the roof wall;
subsequently ablating the posterior wall;
subsequently ablating the superior wall; and
subsequently ablating the floor wall.

69. The method according to claim 65 wherein,
the electrode array of the third catheter includes two or more resilient support arms, each support arm having a proximal arm segment and a distal arm segment connected therebetween by a resilient bend point, each said distal arm segment including a plurality of electrodes of the electrode array of the third catheter disposed thereon in a spaced-apart manner; and
before performing the left atrial wall ablation procedure, deploying the two or more support arms to an expanded condition wherein each distal arm segment extends generally radially outward from a longitudinal axis of the third catheter, creating an acute angle at each bend point between the respective distal arm segment and the corresponding proximal arm segment, and such that during advancing of the electrode array of the third catheter, the plurality of electrodes disposed on the respective distal arm segments are moved into contact with the left atrial wall tissue.

70. The method according to claim 69 wherein,
the first catheter includes a flexible carrier assembly supporting a plurality of the electrodes of the electrode array in a spaced manner, and before performing the pulmonary vein ablation procedure, deploying the carrier assembly of the first catheter to a deployed condition from a near linear geometry to a partially helical or spiral geometry,
the electrode array of the second catheter includes two or more resilient support arms, each support arm having a proximal arm segment and a distal arm segment connected therebetween by a resilient bend point, each said proximal arm segment including a plurality of electrodes of the electrode array of the second catheter disposed thereon in a spaced-apart manner; and
before ablating septal tissue, deploying the two or more support arms to an expanded condition wherein each proximal arm segment and each distal arm segment extends generally radially outward from a longitudinal axis of the second catheter, creating an acute angle at each bend point between the respective distal arm segment and the corresponding proximal arm segment, and such that during retracting of the second catheter, the plurality of electrodes disposed on the respective proximal arm segments are moved into contact with the septal tissue.

71. The method according to claim 70 wherein,
the first catheter is a PVAC device having the electrode array and ablates tissue in a distal facing direction;
the second catheter is a MASC device having the electrode array and ablates tissue in a proximal facing direction; and
the third catheter is a MAAC device having the electrode array and ablates tissue in a distal facing direction.

72. The method of claim 70 wherein,
the first catheter is a PVAC device having the electrode array and ablates tissue in a distal facing direction;
the second catheter is a MASC device having the electrode array and ablates tissue in a proximal facing direction; and
the third catheter is a TVAC device having the electrode array and ablates tissue in a distal facing direction.

73. The method according to claim 65 wherein,
transseptally accessing the left atrium through the puncture with a third catheter is performed by advancing the distal end of the third catheter through a lumen of a transseptal sheath that extends through the puncture; and
prior to ablating septal tissue, withdrawing the transseptal sheath proximally until a distal end of the transseptal sheath is removed from the left atrium of the heart.

74. The method according to claim 73 wherein,
withdrawing the transseptal sheath proximally includes retracting the transseptal sheath proximally at least until the distal end of the transseptal sheath is contained in the right atrium of the heart.

75. The method according to claim 70, wherein after ablating septal tissue, the method further includes ablating tissue surrounding one or more pulmonary veins with a fourth catheter having an electrode array that is at least substantially similar to the electrode array of the first catheter.

76. The method of claim 75 wherein the first and fourth catheters are the same catheter, and wherein the flexible carrier assembly has a plurality of deployed conditions each with a partially helical or spiral geometry, wherein each of the plurality of deployed conditions has a different diameter.

77. The method of claim 75 wherein the fourth catheter comprises a flexible carrier assembly with a deployed condition comprising at least one of a partially helical and spiral geometry, and wherein the diameter of the flexible carrier assembly of the fourth catheter in the deployed condition is different than a diameter of the flexible carrier assembly of the first catheter in the deployed condition.

78. The method according to claim 65, further including:
after performing the left atrial wall ablation procedure, transseptally accessing the left atrium through the puncture with a single point tip ablation catheter having a single electrode disposed on the distal end thereof; and
performing a touch-up ablation procedure with the single point tip ablation catheter.

79. The method according to claim 78, wherein performing the touch-up ablation procedure includes sensing electrical signals of the left atrial wall tissue through the tip electrode of the single point tip ablation catheter; and
upon determining that the electrode of the single point tip ablation catheter is disposed over an aberrant signal of the left atrial wall tissue, passing energy through the tip electrode to ablate a portion of the left atrial wall tissue.

80. The method of claim 27 further comprising:
monitoring the temperature of a first electrode and a second electrode of at least one of the electrode arrays of the first and second catheters when they are in contact with tissue, wherein the monitored temperature of the first electrode is higher than the monitored temperature of the second electrode, and
selectively limiting ablation energy to the first electrode based on the higher temperature.

* * * * *